United States Patent [19]

Houghton et al.

[11] Patent Number: 5,683,864
[45] Date of Patent: Nov. 4, 1997

[54] COMBINATIONS OF HEPATITIS C VIRUS (HCV) ANTIGENS FOR USE IN IMMUNOASSAYS FOR ANTI-HCV ANTIBODIES

[75] Inventors: Michael Houghton, Danville; Qui-Lim Choo, El Cerrito; George Kuo, San Francisco, all of Calif.

[73] Assignee: Chiron Corporation, Emeryville, Calif.

[21] Appl. No.: 910,760

[22] Filed: Jul. 7, 1992

Related U.S. Application Data

[63] Continuation-in-part of Ser. No. 504,352, Apr. 4, 1990, abandoned, which is a continuation-in-part of Ser. No. 355,002, May 18, 1989, abandoned, which is a continuation-in-part of Ser. No. 122,714, Nov. 18, 1987, abandoned, and Ser. No. 139,886, Dec. 30, 1987, abandoned, and Ser. No. 161,072, Feb. 26, 1988, abandoned, and Ser. No. 191,263, May 6, 1988, abandoned, and Ser. No. 263,584, Oct. 26, 1988, abandoned, and Ser. No. 271,450, Nov. 14, 1988, abandoned, and Ser. No. 325,338, filed as PCT/US88/04125, Nov. 18, 1988, abandoned, and Ser. No. 341,334, Apr. 20, 1989, abandoned, and Ser. No. 353,896, Apr. 21, 1989, abandoned.

[51] Int. Cl.$^6$ ............................................. C12Q 1/70
[52] U.S. Cl. .................. 435/5; 436/518; 436/820; 530/350
[58] Field of Search ........................... 530/350, 403, 530/806, 810, 826; 435/5; 436/518, 819, 820

[56] References Cited

U.S. PATENT DOCUMENTS

| | | | |
|---|---|---|---|
| 4,464,474 | 8/1984 | Coursaget | 436/513 |
| 4,701,421 | 10/1987 | Kupers | 436/518 |
| 5,106,726 | 4/1992 | Wang | 435/5 |
| 5,308,750 | 5/1994 | Mehta et al. | 435/5 |
| 5,350,671 | 9/1994 | Houghton et al. | 435/5 |
| 5,436,126 | 7/1995 | Wang et al. | 435/5 |

FOREIGN PATENT DOCUMENTS

| | | |
|---|---|---|
| 0 318 216 | 5/1989 | European Pat. Off. |
| 0 363 025 | 4/1990 | European Pat. Off. |
| 0 445 423 | 9/1991 | European Pat. Off. |
| 0 468 527 | 1/1992 | European Pat. Off. |
| 0 472 207 | 2/1992 | European Pat. Off. |
| 0 484 787 | 5/1992 | European Pat. Off. |
| 4054197 | 2/1992 | Japan |
| 4159298 | 6/1992 | Japan |
| 2 212 511 | 7/1989 | United Kingdom |
| 2 239 245 | 6/1991 | United Kingdom |
| WO 90/00597 | 1/1990 | WIPO |
| WO 91/14779 | 10/1991 | WIPO |
| WO 91/15574 | 10/1991 | WIPO |
| WO 92/10514 | 6/1992 | WIPO |
| WO 92/17493 | 10/1992 | WIPO |

OTHER PUBLICATIONS

Bradley, et al., *Gastroenterology* (1985) 88:773–779.
Choo et al., *Science* (1989) 244:359–362.
Geysen, Mario et al., *Proc. Natl. Science* (1984) 81:3998–4002.
Kuo, George et al., *Science* (1989) 244:362–264.
Krawczynski, Krzysztoft et al., *Gastroenterology* (1992) 103:622–629.
Saito, M. et al., *Clin. Chemistry* (1992) 38:2434–2439.
Sällberg, et al., *J. Clin. Micro.* (1992) 30(8):1989–1994.

*Primary Examiner*—Michael P. Woodward
*Assistant Examiner*—Donna C. Wortman
*Attorney, Agent, or Firm*—Alisa A. Harbin; Tyler M. Dylan; Robert P. Blackburn

[57] ABSTRACT

Combinations of HCV antigens that have a broader range of immunological reactivity than any single HCV antigen. The combinations consist of an antigen from the C domain of the HCV polyprotein, and at least one additional HCV antigen from either the NS3 domain, the NS4 domain, the S domain, or the NS5 domain, and are in the form of a fusion protein, a simple physical mixture, or the individual antigens commonly bound to a solid matrix.

22 Claims, 19 Drawing Sheets

```
                                           -341  GCCAGCCCCCTGATGGGGGCGA
                                                 CGGTCGGGGGACTACCCCCGCT

-319  CACTCCACCATGAATCACTCCCCTGTGAGGAACTACTGTCTTCACGCAGAAAGCGTCTAG
      GTGAGGTGGTACTTAGTGAGGGGACACTCCTTGATGACAGAAGTGCGTCTTTCGCAGATC

-259  CCATGGCGTTAGTATGAGTGTCGTGCAGCCTCCAGGACCCCCCCTCCCGGGAGAGCCATA
      GGTACCGCAATCATACTCACAGCACGTCGGAGGTCCTGGGGGGAGGGCCCTCTCGGTAT

-199  GTGGTCTGCGGAACCGGTGAGTACACCGGAATTGCCAGGACGACCGGGTCCTTTCTTGGA
      CACCAGACGCCTTGGCCACTCATGTGGCCTTAACGGTCCTGCTGGCCCAGGAAAGAACCT

-139  TCAACCCGCTCAATGCCTGGAGATTTGGGCGTGCCCCCGCAAGACTGCTAGCCGAGTAGT
      AGTTGGGCGAGTTACGGACCTCTAAACCCGCACGGGGGCGTTCTGACGATCGGCTCATCA

- 79  GTTGGGTCGCGAAAGGCCTTGTGGTACTGCCTGATAGGGTGCTTGCGAGTGCCCCGGGAG
      CAACCCAGCGCTTTCCGGAACACCATGACGGACTATCCCACGAACGCTCACGGGGCCCTC

- 19  GTCTCGTAGACCGTGCACC
      CAGAGCATCTGGCACGTGG
      ---                Arg  Thr
          MetSerThrAsnProLysProGlnLysLysAsnLysArgAsnThrAsnArgArgProGln
   1  ATGAGCACGAATCCTAAACCTCAAAAAAAAAACAAACGTAACACCAACCGTCGCCCACAG
      TACTCGTGCTTAGGATTTGGAGTTTTTTTTTGTTTGCATTGTGGTTGGCAGCGGGTGTC

AspValLysPheProGlyGlyGlyGlnIleValGlyGlyValTyrLeuLeuProArgArg
  61  GACGTCAAGTTCCCGGGTGGCGGTCAGATCGTTGGTGGAGTTTACTTGTTGCCGCGCAGG
      CTGCAGTTCAAGGGCCCACCGCCAGTCTAGCAACCACCTCAAATGAACAACGGCGCGTCC

GlyProArgLeuGlyValArgAlaThrArgLysThrSerGluArgSerGlnProArgGly
 121  GGCCCTAGATTGGGTGTGCGCGCGACGAGAAAGACTTCCGAGCGGTCGCAACCTCGAGGT
      CCGGGATCTAACCCACACGCGCGCTGCTCTTTCTGAAGGCTCGCCAGCGTTGGAGCTCCA

ArgArgGlnProIleProLysAlaArgArgProGluGlyArgThrTrpAlaGlnProGly
 181  AGACGTCAGCCTATCCCCAAGGCTCGTCGGCCCGAGGGCAGGACCTGGGCTCAGCCCGGG
      TCTGCAGTCGGATAGGGGTTCCGAGCAGCCGGGCTCCCGTCCTGGACCCGAGTCGGGCCC

TyrProTrpProLeuTyrGlyAsnGluGlyCysGlyTrpAlaGlyTrpLeuLeuSerPro
 241  TACCCTTGGCCCCTCTATGGCAATGAGGGCTGCGGGTGGGCGGGATGGCTCCTGTCTCCC
      ATGGGAACCGGGGAGATACCGTTACTCCCGACGCCCACCCGCCCTACCGAGGACAGAGGG

ArgGlySerArgProSerTrpGlyProThrAspProArgArgArgSerArgAsnLeuGly
 301  CGTGGCTCTCGGCCTAGCTGGGGCCCCACAGACCCCGGCGTAGGTCGCGCAATTTGGGT
      GCACCGAGAGCCGGATCGACCCCGGGGTGTCTGGGGCCGCATCCAGCGCGTTAAACCCA

LysValIleAspThrLeuThrCysGlyPheAlaAspLeuMetGlyTyrIleProLeuVal
 361  AAGGTCATCGATACCCTTACGTGCGGCTTCGCCGACCTCATGGGTACATACCGCTCGTC
      TTCCAGTAGCTATGGGAATGCACGCCGAAGCGGCTGGAGTACCCATGTATGGCGAGCAG

GlyAlaProLeuGlyGlyAlaAlaArgAlaLeuAlaHisGlyValArgValLeuGluAsp
 421  GGCGCCCCTCTTGGAGGCGCTGCCAGGGCCCTGGCGCATGGCGTCCGGGTTCTGGAAGAC
      CCGCGGGGAGAACCTCCGCGACGGTCCCGGGACCGCGTACCGCAGGCCCAAGACCTTCTG
```

FIG. 1A

```
                                                            Thr
      GlyValAsnTyrAlaThrGlyAsnLeuProGlyCysSerPheSerIlePheLeuLeuAla
 481  GGCGTGAACTATGCAACAGGGAACCTTCCTGGTTGCTCTTTCTCTATCTTCCTTCTGGCC
      CCGCACTTGATACGTTGTCCCTTGGAAGGACCAACGAGAAAGAGATAGAAGGAAGACCGG

LeuLeuSerCysLeuThrValProAlaSerAlaTyrGlnValArgAsnSerThrGlyLeu
 541  CTGCTCTCTTGCTTGACTGTGCCCGCTTCGGCCTACCAAGTGCGCAACTCCACGGGGCTT
      GACGAGAGAACGAACTGACACGGGCGAAGCCGGATGGTTCACGCGTTGAGGTGCCCCGAA

TyrHisValThrAsnAspCysProAsnSerSerIleValTyrGluAlaAlaAspAlaIle
 601  TACCACGTCACCAATGATTGCCCTAACTCGAGTATTGTGTACGAGGCGGCCGATGCCATC
      ATGGTGCAGTGGTTACTAACGGGATTGAGCTCATAACACATGCTCCGCCGGCTACGGTAG

LeuHisThrProGlyCysValProCysValArgGluGlyAsnAlaSerArgCysTrpVal
 661  CTGCACACTCCGGGGTGCGTCCCTTGCGTTCGTGAGGGCAACGCCTCGAGGTGTTGGGTG
      GACGTGTGAGGCCCCACGCAGGGAACGCAAGCACTCCCGTTGCGGAGCTCCACAACCCAC

AlaMetThrProThrValAlaThrArgAspGlyLysLeuProAlaThrGlnLeuArgArg
 721  GCGATGACCCCTACGGTGGCCACCAGGGATGGCAAACTCCCCGCGACGCAGCTTCGACGT
      CGCTACTGGGGATGCCACCGGTGGTCCCTACCGTTTGAGGGGCGCTGCGTCGAAGCTGCA

HisIleAspLeuLeuValGlySerAlaThrLeuCysSerAlaLeuTyrValGlyAspLeu
 781  CACATCGATCTGCTTGTCGGGAGCGCCACCCTCTGTTCGGCCCTCTACGTGGGGGACCTA
      GTGTAGCTAGACGAACAGCCCTCGCGGTGGGAGACAAGCCGGGAGATGCACCCCCTGGAT

CysGlySerValPheLeuValGlyGlnLeuPheThrPheSerProArgArgHisTrpThr
 841  TGCGGGTCTGTCTTTCTTGTCGGCCAACTGTTCACCTTCTCTCCCAGGCGCCACTGGACG
      ACGCCCAGACAGAAAGAACAGCCGGTTGACAAGTGGAAGAGAGGGTCCGCGGTGACCTGC

ThrGlnGlyCysAsnCysSerIleTyrProGlyHisIleThrGlyHisArgMetAlaTrp
 901  ACGCAAGGTTGCAATTGCTCTATCTATCCCGGCCATATAACGGGTCACCGCATGGCATGG
      TGCGTTCCAACGTTAACGAGATAGATAGGGCCGGTATATTGCCCAGTGGCGTACCGTACC

Val
      AspMetMetMetAsnTrpSerProThrThrAlaLeuValMetAlaGlnLeuLeuArgIle
 961  GATATGATGATGAACTGGTCCCCTACGACGGCGTTGGTAATGGCTCAGCTGCTCCGGATC
      CTATACTACTACTTGACCAGGGGATGCTGCCGCAACCATTACCGAGTCGACGAGGCCTAG

ProGlnAlaIleLeuAspMetIleAlaGlyAlaHisTrpGlyValLeuAlaGlyIleAla
1021  CCACAAGCCATCTTGGACATGATCGCTGGTGCTCACTGGGGAGTCCTGGCGGGCATAGCG
      GGTGTTCGGTAGAACCTGTACTAGCGACCACGAGTGACCCCTCAGGACCGCCCGTATCGC

TyrPheSerMetValGlyAsnTrpAlaLysValLeuValValLeuLeuLeuPheAlaGly
1081  TATTTCTCCATGGTGGGGAACTGGGCGAAGGTCCTGGTATTGCTGCTGCTATTTGCCGGC
      ATAAAGAGGTACCACCCCTTGACCCGCTTCCAGGACCATAACGACGACGATAAACGGCCG

ValAspAlaGluThrHisValThrGlyGlySerAlaGlyHisThrValSerGlyPheVal
1141  GTCGACGCGGAAACCCACGTCACCGGGGGAAGTGCCGGCCACACTGTGTCTGGATTTGTT
      CAGCTGCGCCTTTGGGTGCAGTGGCCCCCTTCACGGCCGGTGTGACACAGACCTAAACAA

SerLeuLeuAlaProGlyAlaLysGlnAsnValGlnLeuIleAsnThrAsnGlySerTrp
1201  AGCCTCCTCGCACCAGGCGCCAAGCAGAACGTCCAGCTGATCAACACCAACGGCAGTTGG
      TCGGAGGAGCGTGGTCCGCGGTTCGTCTTGCAGGTCGACTAGTTGTGGTTGCCGTCAACC
```

FIG. IB

```
     HisLeuAsnSerThrAlaLeuAsnCysAsnAspSerLeuAsnThrGlyTrpLeuAlaGly
1261 CACCTCAATAGCACGGCCCTGAACTGCAATGATAGCCTCAACACCGGCTGGTTGGCAGGG
     GTGGAGTTATCGTGCCGGGACTTGACGTTACTATCGGAGTTGTGGCCGACCAACCGTCCC

LeuPheTyrHisHisLysPheAsnSerSerGlyCysProGluArgLeuAlaSerCysArg
1321 CTTTTCTATCACCACAAGTTCAACTCTTCAGGCTGTCCTGAGAGGCTAGCCAGCTGCCGA
     GAAAAGATAGTGGTGTTCAAGTTGAGAAGTCCGACAGGACTCTCCGATCGGTCGACGGCT

ProLeuThrAspPheAspGlnGlyTrpGlyProIleSerTyrAlaAsnGlySerGlyPro
1381 CCCCTTACCGATTTTGACCAGGGCTGGGGCCCTATCAGTTATGCCAACGGAAGCGGCCCC
     GGGGAATGGCTAAAACTGGTCCCGACCCCGGGATAGTCAATACGGTTGCCTTCGCCGGGG

AspGlnArgProTyrCysTrpHisTyrProProLysProCysGlyIleValProAlaLys
1441 GACCAGCGCCCTACTGCTGGCACTACCCCCAAAACCTTGCGGTATTGTGCCCGCGAAG
     CTGGTCGCGGGGATGACGACCGTGATGGGGGTTTTGGAACGCCATAACACGGGCGCTTC

SerValCysGlyProValTyrCysPheThrProSerProValValValGlyThrThrAsp
1501 AGTGTGTGTGGTCCGGTATATTGCTTCACTCCAGCCCGTGGTGGTGGGAACGACCGAC
     TCACACACACCAGGCCATATAACGAAGTGAGGGTCGGGGCACCACCACCCTTGCTGGCTG

ArgSerGlyAlaProThrTyrSerTrpGlyGluAsnAspThrAspValPheValLeuAsn
1561 AGGTCGGGCGCGCCCACCTACAGCTGGGGTGAAAATGATACGGACGTCTTCGTCCTTAAC
     TCCAGCCCGCGCGGGTGGATGTCGACCCCACTTTTACTATGCCTGCAGAAGCAGGAATTG

AsnThrArgProProLeuGlyAsnTrpPheGlyCysThrTrpMetAsnSerThrGlyPhe
1621 AATACCAGGCCACCGCTGGGCAATTGGTTCGGTTGTACCTGGATGAACTCAACTGGATTC
     TTATGGTCCGGTGGCGACCCGTTAACCAAGCCAACATGGACCTACTTGAGTTGACCTAAG

ThrLysValCysGlyAlaProProCysValIleGlyGlyAlaGlyAsnAsnThrLeuHis
1681 ACCAAAGTGTGCGGAGCGCCTCCTTGTGTCATCGGAGGGGCGGGCAACAACACCCTGCAC
     TGGTTTCACACGCCTCGCGGAGGAACACAGTAGCCTCCCCGCCCGTTGTTGTGGGACGTG

CysProThrAspCysPheArgLysHisProAspAlaThrTyrSerArgCysGlySerGly
1741 TGCCCCACTGATTGCTTCCGCAAGCATCCGGACGCCACATACTCTCGGTGCGGCTCCGGT
     ACGGGGTGACTAACGAAGGCGTTCGTAGGCCTGCGGTGTATGAGAGCCACGCCGAGGCCA

Ile
     ProTrpLeuThrProArgCysLeuValAspTyrProTyrArgLeuTrpHisTyrProCys
1801 CCCTGGATCACACCCAGGTGCCTGGTCGACTACCCGTATAGGCTTTGGCATTATCCTTGT
     GGGACCTAGTGTGGGTCCACGGACCAGCTGATGGGCATATCCGAAACCGTAATAGGAACA

ThrIleAsnTyrThrIlePheLysIleArgMetTyrValGlyGlyValGluHisArgLeu
1861 ACCATCAACTACACCATATTTAAAATCAGGATGTACGTGGGAGGGGTCGAACACAGGCTG
     TGGTAGTTGATGTGGTATAAATTTTAGTCCTACATGCACCCTCCCCAGCTTGTGTCCGAC

GluAlaAlaCysAsnTrpThrArgGlyGluArgCysAspLeuGluAspArgAspArgSer
1921 GAAGCTGCCTGCAACTGGACGCGGGGCGAACGTTGCGATCTGGAAGACAGGGACAGGTCC
     CTTCGACGGACGTTGACCTGCGCCCCGCTTGCAACGCTAGACCTTCTGTCCCTGTCCAGG

GluLeuSerProLeuLeuLeuThrThrThrGlnTrpGlnValLeuProCysSerPheThr
1981 GAGCTCAGCCCGTTACTGCTGACCACTACACAGTGGCAGGTCCTCCCGTGTTCCTTCACA
     CTCGAGTCGGGCAATGACGACTGGTGATGTGTCACCGTCCAGGAGGGCACAAGGAAGTGT
```

FIG. 1C

```
               ThrLeuProAlaLeuSerThrGlyLeuIleHisLeuHisGlnAsnIleValAspValGln
2041           ACCCTACCAGCCTTGTCCACCGGCCTCATCCACCTCCACCAGAACATTGTGGACGTGCAG
               TGGGATGGTCGGAACAGGTGGCCGGAGTAGGTGGAGGTGGTCTTGTAACACCTGCACGTC

TyrLeuTyrGlyValGlySerSerIleAlaSerTrpAlaIleLysTrpGluTyrValVal
2101           TACTTGTACGGGGTGGGGTCAAGCATCGCGTCCTGGGCCATTAAGTGGGAGTACGTCGTT
               ATGAACATGCCCCACCCCAGTTCGTAGCGCAGGACCCGGTAATTCACCCTCATGCAGCAA

LeuLeuPheLeuLeuLeuAlaAspAlaArgValCysSerCysLeuTrpMetMetLeuLeu
2161           CTCCTGTTCCTTCTGCTTGCAGACGCGCGCGTCTGCTCCTGCTTGTGGATGATGCTACTC
               GAGGACAAGGAAGACGAACGTCTGCGCGCGCAGACGAGGACGAACACCTACTACGATGAG

IleSerGlnAlaGluAlaAlaLeuGluAsnLeuValIleLeuAsnAlaAlaSerLeuAla
2221           ATATCCCAAGCGGAGGCGGCTTTGGAGAACCTCGTAATACTTAATGCAGCATCCCTGGCC
               TATAGGGTTCGCCTCCGCCGAAACCTCTTGGAGCATTATGAATTACGTCGTAGGGACCGG

GlyThrHisGlyLeuValSerPheLeuValPhePheCysPheAlaTrpTyrLeuLysGly
2281           GGGACGCACGGTCTTGTATCCTTCCTCGTGTTCTTCTGCTTTGCATGGTATTTGAAGGGT
               CCCTGCGTGCCAGAACATAGGAAGGAGCACAAGAAGACGAAACGTACCATAAACTTCCCA

LysTrpValProGlyAlaValTyrThrPheTyrGlyMetTrpProLeuLeuLeuLeuLeu
2341           AAGTGGGTGCCCGGAGCGGTCTACACCTTCTACGGGATGTGGCCTCTCCTCCTGCTCCTG
               TTCACCCACGGGCCTCGCCAGATGTGGAAGATGCCCTACACCGGAGAGGAGGACGAGGAC

LeuAlaLeuProGlnArgAlaTyrAlaLeuAspThrGluValAlaAlaSerCysGlyGly
2401           TTGGCGTTGCCCCAGCGGGCGTACGCGCTGGACACGGAGGTGGCCGCGTCGTGTGGCGGT
               AACCGCAACGGGGTCGCCCGCATGCGCGACCTGTGCCTCCACCGGCGCAGCACACCGCCA

ValValLeuValGlyLeuMetAlaLeuThrLeuSerProTyrTyrLysArgTyrIleSer
2461           GTTGTTCTCGTCGGGTTGATGGCGCTGACTCTGTCACCATATTACAAGCGCTATATCAGC
               CAACAAGAGCAGCCCAACTACCGCGACTGAGACAGTGGTATAATGTTCGCGATATAGTCG (Asn)
               TrpCysLeuTrpTrpLeuGlnTyrPheLeuThrArgValGluAlaGlnLeuHisValTrp
2521           TGGTGCTTGTGGTGGCTTCAGTATTTTCTGACCAGAGTGGAAGCGCAACTGCACGTGTGG
               ACCACGAACACCACCGAAGTCATAAAAGACTGGTCTCACCTTCGCGTTGACGTGCACACC

IleProProLeuAsnValArgGlyGlyArgAspAlaValIleLeuLeuMetCysAlaVal
2581           ATTCCCCCCCTCAACGTCCGAGGGGGCGCGACGCCGTCATCTTACTCATGTGTGCTGTA
               TAAGGGGGGGAGTTGCAGGCTCCCCCGCGCTGCGGCAGTAGAATGAGTACACACGACAT

HisProThrLeuValPheAspIleThrLysLeuLeuLeuAlaValPheGlyProLeuTrp
2641           CACCCGACTCTGGTATTTGACATCACCAAATTGCTGCTGGCCGTCTTCGGACCCCTTTGG
               GTGGGCTGAGACCATAAACTGTAGTGGTTTAACGACGACCGGCAGAAGCCTGGGGAAACC

IleLeuGlnAlaSerLeuLeuLysValProTyrPheValArgValGlnGlyLeuLeuArg
2701           ATTCTTCAAGCCAGTTTGCTTAAAGTACCCTACTTTGTGCGCGTCCAAGGCCTTCTCCGG
               TAAGAAGTTCGGTCAAACGAATTTCATGGGATGAAACACGCGCAGGTTCCGGAAGAGGCC

PheCysAlaLeuAlaArgLysMetIleGlyGlyHisTyrValGlnMetValIleIleLys
2761           TTCTGCGCGTTAGCGCGGAAGATGATCGGAGGCCATTACGTGCAAATGGTCATCATTAAG
               AAGACGCGCAATCGCGCCTTCTACTAGCCTCCGGTAATGCACGTTTACCAGTAGTAATTC
```

FIG. 1D

```
              LeuGlyAlaLeuThrGlyThrTyrValTyrAsnHisLeuThrProLeuArgAspTrpAla
2821          TTAGGGGCGCTTACTGGCACCTATGTTTATAACCATCTCACTCCTCTTCGGGACTGGGCG
              AATCCCCGCGAATGACCGTGGATACAAATATTGGTAGAGTGAGGAGAAGCCCTGACCCGC

HisAsnGlyLeuArgAspLeuAlaValAlaValGluProValValPheSerGlnMetGlu
2881          CACAACGGCTTGCGAGATCTGGCCGTGGCTGTAGAGCCAGTCGTCTTCTCCCAAATGGAG
              GTGTTGCCGAACGCTCTAGACCGGCACCGACATCTCGGTCAGCAGAAGAGGGTTTACCTC

ThrLysLeuIleThrTrpGlyAlaAspThrAlaAlaCysGlyAspIleIleAsnGlyLeu
2941          ACCAAGCTCATCACGTGGGGGGCAGATACCGCCGCGTGCGGTGACATCATCAACGGCTTG
              TGGTTCGAGTAGTGCACCCCCGTCTATGGCGGCGCACGCCACTGTAGTAGTTGCCGAAC

ProValSerAlaArgArgGlyArgGluIleLeuLeuGlyProAlaAspGlyMetValSer
3001          CCTGTTTCCGCCCGCAGGGGCCGGGAGATACTGCTCGGGCCAGCCGATGGAATGGTCTCC
              GGACAAAGGCGGGCGTCCCCGGCCCTCTATGACGAGCCCGGTCGGCTACCTTACCAGAGG

LysGlyTrpArgLeuLeuAlaProIleThrAlaTyrAlaGlnGlnThrArgGlyLeuLeu
3061          AAGGGGTGGAGGTTGCTGGCGCCCATCACGGCGTACGCCCAGCAGACAAGGGGCCTCCTA
              TTCCCCACCTCCAACGACCGCGGGTAGTGCCGCATGCGGGTCGTCTGTTCCCCGGAGGAT

GlyCysIleIleThrSerLeuThrGlyArgAspLysAsnGlnValGluGlyGluValGln
3121          GGGTGCATAATCACCAGCCTAACTGGCCGGGACAAAAACCAAGTGGAGGGTGAGGTCCAG
              CCCACGTATTAGTGGTCGGATTGACCGGCCCTGTTTTTGGTTCACCTCCCACTCCAGGTC

IleValSerThrAlaAlaGlnThrPheLeuAlaThrCysIleAsnGlyValCysTrpThr
3181          ATTGTGTCAACTGCTGCCCAAACCTTCCTGGCAACGTGCATCAATGGGGTGTGCTGGACT
              TAACACAGTTGACGACGGGTTTGGAAGGACCGTTGCACGTAGTTACCCCACACGACCTGA

ValTyrHisGlyAlaGlyThrArgThrIleAlaSerProLysGlyProValIleGlnMet
3241          GTCTACCACGGGGCCGGAACGAGGACCATCGCGTCACCCAAGGGTCCTGTCATCCAGATG
              CAGATGGTGCCCCGGCCTTGCTCCTGGTAGCGCAGTGGGTTCCCAGGACAGTAGGTCTAC

Ser      Thr
              TyrThrAsnValAspGlnAspLeuValGlyTrpProAlaProGlnGlySerArgSerLeu
3301          TATACCAATGTAGACCAAGACCTTGTGGGCTGGCCCGCTCCGCAAGGTAGCCGCTCATTG
              ATATGGTTACATCTGGTTCTGGAACACCCGACCGGGCGAGGCGTTCCATCGGCGAGTAAC

ThrProCysThrCysGlySerSerAspLeuTyrLeuValThrArgHisAlaAspValIle
3361          ACACCCTGCACTTGCGGCTCCTCGGACCTTTACCTGGTCACGAGGCACGCCGATGTCATT
              TGTGGGACGTGAACGCCGAGGAGCCTGGAAATGGACCAGTGCTCCGTGCGGCTACAGTAA

ProValArgArgArgGlyAspSerArgGlySerLeuLeuSerProArgProIleSerTyr
3421          CCCGTGCGCCGGCGGGGTGATAGCAGGGGCAGCCTGCTGTCGCCCCGGCCCATTTCCTAC
              GGGCACGCGGCCGCCCCACTATCGTCCCCGTCGGACGACAGCGGGGCCGGGTAAAGGATG

LeuLysGlySerSerGlyGlyProLeuLeuCysProAlaGlyHisAlaValGlyIlePhe
3481          TTGAAAGGCTCCTCGGGGGGTCCGCTGTTGTGCCCCGCGGGGCACGCCGTGGGCATATTT
              AACTTTCCGAGGAGCCCCCAGGCGACAACACGGGGCGCCCCGTGCGGCACCCGTATAAA

ArgAlaAlaValCysThrArgGlyValAlaLysAlaValAspPheIleProValGluAsn
3541          AGGGCCGCGGTGTGCACCCGTGGAGTGGCTAAGGCGGTGGACTTTATCCCTGTGGAGAAC
              TCCCGGCGCCACACGTGGGCACCTCACCGATTCCGCCACCTGAAATAGGGACACCTCTTG
```

FIG. IE

```
       LeuGluThrThrMetArgSerProValPheThrAspAsnSerSerProProValValPro
3601   CTAGAGACAACCATGAGGTCCCCGGTGTTCACGGATAACTCCTCTCCACCAGTAGTGCCC
       GATCTCTGTTGGTACTCCAGGGGCCACAAGTGCCTATTGAGGAGAGGTGGTCATCACGGG

GlnSerPheGlnValAlaHisLeuHisAlaProThrGlySerGlyLysSerThrLysVal
3661   CAGAGCTTCCAGGTGGCTCACCTCCATGCTCCCACAGGCAGCGGCAAAAGCACCAAGGTC
       GTCTCGAAGGTCCACCGAGTGGAGGTACGAGGGTGTCCGTCGCCGTTTTCGTGGTTCCAG

ProAlaAlaTyrAlaAlaGlnGlyTyrLysValLeuValLeuAsnProSerValAlaAla
3721   CCGGCTGCATATGCAGCTCAGGGCTATAAGGTGCTAGTACTCAACCCCTCTGTTGCTGCA
       GGCCGACGTATACGTCGAGTCCCGATATTCCACGATCATGAGTTGGGGAGACAACGACGT

Leu
       ThrLeuGlyPheGlyAlaTyrMetSerLysAlaHisGlyIleAspProAsnIleArgThr
3781   ACACTGGGCTTTGGTGCTTACATGTCCAAGGCTCATGGGATCGATCCTAACATCAGGACC
       TGTGACCCGAAACCACGAATGTACAGGTTCCGAGTACCCTAGCTAGGATTGTAGTCCTGG

GlyValArgThrIleThrThrGlySerProIleThrTyrSerThrTyrGlyLysPheLeu
3841   GGGGTGAGAACAATTACCACTGGCAGCCCCATCACGTACTCCACCTACGGCAAGTTCCTT
       CCCCACTCTTGTTAATGGTGACCGTCGGGGTAGTGCATGAGGTGGATGCCGTTCAAGGAA

AlaAspGlyGlyCysSerGlyGlyAlaTyrAspIleIleIleCysAspGluCysHisSer
3901   GCCGACGGCGGGTGCTCGGGGGGCGCTTATGACATAATAATTTGTGACGAGTGCCACTCC
       CGGCTGCCGCCCACGAGCCCCCCGCGAATACTGTATTATTAAACACTGCTCACGGTGAGG (Val)
       ThrAspAlaThrSerIleLeuGlyIleGlyThrValLeuAspGlnAlaGluThrAlaGly
3961   ACGGATGCCACATCCATCTTGGGCATCGGCACTGTCCTTGACCAAGCAGAGACTGCGGGG
       TGCCTACGGTGTAGGTAGAACCCGTAGCCGTGACAGGAACTGGTTCGTCTCTGACGCCCC

AlaArgLeuValValLeuAlaThrAlaThrProProGlySerValThrValProHisPro
4021   GCGAGACTGGTTGTGCTCGCCACCGCCACCCCTCCGGGCTCCGTCACTGTGCCCCATCCC
       CGCTCTGACCAACACGAGCGGTGGCGGTGGGGAGGCCCGAGGCAGTGACACGGGGTAGGG

AsnIleGluGluValAlaLeuSerThrThrGlyGluIleProPheTyrGlyLysAlaIle
4081   AACATCGAGGAGGTTGCTCTGTCCACCACCGGAGAGATCCCTTTTTACGGCAAGGCTATC
       TTGTAGCTCCTCCAACGAGACAGGTGGTGGCCTCTCTAGGGAAAAATGCCGTTCCGATAG

ProLeuGluValIleLysGlyGlyArgHisLeuIlePheCysHisSerLysLysLysCys
4141   CCCCTCGAAGTAATCAAGGGGGGGAGACATCTCATCTTCTGTCATTCAAAGAAGAAGTGC
       GGGGAGCTTCATTAGTTCCCCCCCTCTGTAGAGTAGAAGACAGTAAGTTTCTTCTTCACG

AspGluLeuAlaAlaLysLeuValAlaLeuGlyIleAsnAlaValAlaTyrTyrArgGly
4201   GACGAACTCGCCGCAAAGCTGGTCGCATTGGGCATCAATGCCGTGGCCTACTACCGCGGT
       CTGCTTGAGCGGCGTTTCGACCAGCGTAACCCGTAGTTACGGCACCGGATGATGGCGCCA

LeuAspValSerValIleProThrSerGlyAspValValValValAlaThrAspAlaLeu
4261   CTTGACGTGTCCGTCATCCCGACCAGCGGCGATGTTGTCGTCGTGGCAACCGATGCCCTC
       GAACTGCACAGGCAGTAGGGCTGGTCGCCGCTACAACAGCAGCACCGTTGGCTACGGGAG

Tyr
       MetThrGlyTyrThrGlyAspPheAspSerValIleAspCysAsnThrCysValThrGln
4321   ATGACCGGCTATACCGGCGACTTCGACTCGGTGATAGACTGCAATACGTGTGTCACCCAG
       TACTGGCCGATATGGCCGCTGAAGCTGAGCCACTATCTGACGTTATGCACACAGTGGGTC
```

FIG. 1F

```
                  (Ser)
       ThrValAspPheSerLeuAspProThrPheThrIleGluThrIleThrLeuProGlnAsp
4381   ACAGTCGATTTCAGCCTTGACCCTACCTTCACCATTGAGACAATCACGCTCCCCCAGGAT
       TGTCAGCTAAAGTCGGAACTGGGATGGAAGTGGTAACTCTGTTAGTGCGAGGGGGTCCTA

AlaValSerArgThrGlnArgArgGlyArgThrGlyArgGlyLysProGlyIleTyrArg
4441   GCTGTCTCCCGCACTCAACGTCGGGGCAGGACTGGCAGGGGAAGCCAGGCATCTATAGA
       CGACAGAGGGCGTGAGTTGCAGCCCCGTCCTGACCGTCCCCCTTCGGTCCGTAGATCTCT

PheValAlaProGlyGluArgProSerGlyMetPheAspSerSerValLeuCysGluCys
4501   TTTGTGGCACCGGGGGAGCGCCCCTCCGGCATGTTCGACTCGTCCGTCCTCTGTGAGTGC
       AAACACCGTGGCCCCCTCGCGGGGAGGCCGTACAAGCTGAGCAGGCAGGAGACACTCACG

TyrAspAlaGlyCysAlaTrpTyrGluLeuThrProAlaGluThrThrValArgLeuArg
4561   TATGACGCAGGCTGTGCTTGGTATGAGCTCACGCCCGCCGAGACTACAGTTAGGCTACGA
       ATACTGCGTCCGACACGAACCATACTCGAGTGCGGGCGGCTCTGATGTCAATCCGATGCT

AlaTyrMetAsnThrProGlyLeuProValCysGlnAspHisLeuGluPheTrpGluGly
4621   GCGTACATGAACACCCCGGGGCTTCCCGTGTGCCAGGACCATCTTGAATTTTGGGAGGGC
       CGCATGTACTTGTGGGGCCCCGAAGGGCACACGGTCCTGGTAGAACTTAAAACCCTCCCG

ValPheThrGlyLeuThrHisIleAspAlaHisPheLeuSerGlnThrLysGlnSerGly
4681   GTCTTTACAGGCCTCACTCATATAGATGCCCACTTTCTATCCCAGACAAAGCAGAGTGGG
       CAGAAATGTCCGGAGTGAGTATATCTACGGGTGAAAGATAGGGTCTGTTTCGTCTCACCC

GluAsnLeuProTyrLeuValAlaTyrGlnAlaThrValCysAlaArgAlaGLnAlaPro
4741   GAGAACCTTCCTTACCTGGTAGCGTACCAAGCCACCGTGTGCGCTAGGGCTCAAGCCCCT
       CTCTTGGAAGGAATGGACCATCGCATGGTTCGGTGGCACACGCGATCCCGAGTTCGGGGA

ProProSerTrpAspGlnMetTrpLysCysLeuIleArgLeuLysProThrLeuHisGly
4801   CCCCCATCGTGGGACCAGATGTGGAAGTGTTTGATTCGCCTCAAGCCCACCCTCCATGGG
       GGGGGTAGCACCCTGGTCTACACCTTCACAAACTAAGCGGAGTTCGGGTGGGAGGTACCC

ProThrProLeuLeuTyrArgLeuGlyAlaValGlnAsnGluIleThrLeuThrHisPro
4861   CCAACACCCCTGCTATACAGACTGGGCGCTGTTCAGAATGAAATCACCCTGACGCACCCA
       GGTTGTGGGGACGATATGTCTGACCCGCGACAAGTCTTACTTTAGTGGGACTGCGTGGGT

ValThrLysTyrIleMetThrCysMetSerAlaAspLeuGluValValThrSerThrTrp
4921   GTCACCAAATACATCATGACATGCATGTCGGCCGACCTGGAGGTCGTCACGAGCACCTGG
       CAGTGGTTTATGTAGTACTGTACGTACAGCCGGCTGGACCTCCAGCAGTGCTCGTGGACC

ValLeuValGlyGlyValLeuAlaAlaLeuAlaAlaTyrCysLeuSerThrGlyCysVal
4981   GTGCTCGTTGGCGGCGTCCTGGCTGCTTTGGCCGCGTATTGCCTGTCAACAGGCTGCGTG
       CACGAGCAACCGCCGCAGGACCGACGAAACCGGCGCATAACGGACAGTTGTCCGACGCAC

ValIleValGlyArgValValLeuSerGlyLysProAlaIleIleProAspArgGluVal
5041   GTCATAGTGGGCAGGGTCGTCTTGTCCGGGAAGCCGGCAATCATACCTGACAGGGAAGTC
       CAGTATCACCCGTCCCAGCAGAACAGGCCCTTCGGCCGTTAGTATGGACTGTCCCTTCAG

LeuTyrArgGluPheAspGluMetGluGluCysSerGlnHisLeuProTyrIleGluGln
5101   CTCTACCGAGAGTTCGATGAGATGGAAGAGTGCTCTCAGCACTTACCGTACATCGAGCAA
       GAGATGGCTCTCAAGCTACTCTACCTTCTCACGAGAGTCGTGAATGGCATGTAGCTCGTT
```

FIG. IG

```
        GlyMetMetLeuAlaGluGlnPheLysGlnLysAlaLeuGlyLeuLeuGlnThrAlaSer
5161    GGGATGATGCTCGCCGAGCAGTTCAAGCAGAAGGCCCTCGGCCTCCTGCAGACCGCGTCC
        CCCTACTACGAGCGGCTCGTCAAGTTCGTCTTCCGGGAGCCGGAGGACGTCTGGCGCAGG

ArgGlnAlaGluValIleAlaProAlaValGlnThrAsnTrpGlnLysLeuGluThrPhe
5221    CGTCAGGCAGAGGTTATCGCCCCTGCTGTCCAGACCAACTGGCAAAAACTCGAGACCTTC
        GCAGTCCGTCTCCAATAGCGGGGACGACAGGTCTGGTTGACCGTTTTTGAGCTCTGGAAG

TrpAlaLysHisMetTrpAsnPheIleSerGlyIleGlnTyrLeuAlaGlyLeuSerThr
5281    TGGGCGAAGCATATGTGGAACTTCATCAGTGGGATACAATACTTGGCGGGCTTGTCAACG
        ACCCGCTTCGTATACACCTTGAAGTAGTCACCCTATGTTATGAACCGCCCGAACAGTTGC

LeuProGlyAsnProAlaIleAlaSerLeuMetAlaPheThrAlaAlaValThrSerPro
5341    CTGCCTGGTAACCCCGCCATTGCTTCATTGATGGCTTTTACAGCTGCTGTCACCAGCCCA
        GACGGACCATTGGGGCGGTAACGAAGTAACTACCGAAAATGTCGACGACAGTGGTCGGGT

LeuThrThrSerGlnThrLeuLeuPheAsnIleLeuGlyValTrpValAlaAlaGlnLeu
5401    CTAACCACTAGCCAAACCCTCCTCTTCAACATATTGGGCGTGTGGGTCGCTGCCCAGCTC
        GATTGGTGATCGGTTTGGGAGGAGAAGTTGTATAACCCCGCACCCAGCGACGGGTCGAG

AlaAlaProGlyAlaAlaThrAlaPheValGlyAlaGlyLeuAlaGlyAlaAlaIleGly
5461    GCCGCCCCCGGTGCCGCTACTGCCTTTGTGGGCGCTGGCTTAGCTGGCGCCGCCATCGGC
        CGGCGGGGCCACGGCGATGACGGAAACACCCGCGACCGAATCGACCGCGGCGGTAGCCG

SerValGlyLeuGlyLysValLeuIleAspIleLeuAlaGlyTyrGlyAlaGlyValAla
5521    AGTGTTGGACTGGGGAAGGTCCTCATAGACATCCTTGCAGGTATGGCGCGGCGTGGCG
        TCACAACCTGACCCCTTCCAGGAGTATCTGTAGGAACGTCCATACCGCGCCGCACCGC (Gly)
        GlyAlaLeuValAlaPheLysIleMetSerGlyGluValProSerThrGluAspLeuVal
5581    GGAGCTCTTGTGGCATTCAAGATCATGAGCGGTGAGGTCCCCTCCACGGAGGACCTGGTC
        CCTCGAGAACACCGTAAGTTCTAGTACTCGCCACTCCAGGGAGGTGCCTCCTGGACCAG

AsnLeuLeuProAlaIleLeuSerProGlyAlaLeuValValGlyValValCysAlaAla
5641    AATCTACTGCCCGCCATCCTCTCGCCCGGAGCCCTCGTAGTCGGCGTGGTCTGTGCAGCA
        TTAGATGACGGGCGGTAGGAGAGCGGGCCTCGGGAGCATCAGCCGCACCAGACACGTCGT

IleLeuArgArgHisValGlyProGlyGlyAlaValGlnTrpMetAsnArgLeuIle
5701    ATACTGCGCCGGCACGTTGGCCCGGGCGAGGGGGCAGTGCAGTGGATGAACCGGCTGATA
        TATGACGCGGCCGTGCAACCGGGCCCGCTCCCCCGTCACGTCACCTACTTGGCCGACTAT

AlaPheAlaSerArgGlyAsnHisValSerProThrHisTyrValProGlySerAspAla
5761    GCCTTCGCCTCCCGGGGGAACCATGTTTCCCCCACGCACTACGTGCCGGGAGCGATGCA
        CGGAAGCGGAGGGCCCCCTTGGTACAAAGGGGGTGCGTGATGCACGGCCTCGCTACGT (HisCys)
        AlaAlaArgValThrAlaIleLeuSerSerLeuThrValThrGlnLeuLeuArgArgLeu
5821    GCTGCCCGCGTCACTGCCATACTCAGCAGCCTCACTGTAACCCAGCTCCTGAGGCGACTG
        CGACGGGCGCAGTGACGGTATGAGTCGTCGGAGTGACATTGGGTCGAGGACTCCGCTGAC

HisGlnTrpIleSerSerGluCysThrThrProCysSerGlySerTrpLeuArgAspIle
5881    CACCAGTGGATAAGCTCGGAGTGTACCACTCCATGCTCCGGTCCTGGCTAAGGGACATC
        GTGGTCACCTATTCGAGCCTCACATGGTGAGGTACGAGGCCAGGACCGATTCCCTGTAG
```

FIG. 1H

```
       TrpAspTrpIleCysGluValLeuSerAspPheLysThrTrpLeuLysAlaLysLeuMet
5941   TGGGACTGGATATGCGAGGTGTTGAGCGACTTTAAGACCTGGCTAAAAGCTAAGCTCATG
       ACCCTGACCTATACGCTCCACAACTCGCTGAAATTCTGGACCGATTTTCGATTCGAGTAC

ProGlnLeuProGlyIleProPheValSerCysGlnArgGlyTyrLysGlyValTrpArg
6001   CCACAGCTGCCTGGGATCCCCTTTGTGTCCTGCCAGCGCGGGTATAAGGGGGTCTGGCGA
       GGTGTCGACGGACCCTAGGGGAAACACAGGACGGTCGCGCCCATATTCCCCCAGACCGCT (Val)
       GlyAspGlyIleMetHisThrArgCysHisCysGlyAlaGluIleThrGlyHisValLys
6061   GTGGACGGCATCATGCACACTCGCTGCCACTGTGGAGCTGAGATCACTGGACATGTCAAA
       CACCTGCCGTAGTACGTGTGAGCGACGGTGACACCTCGACTCTAGTGACCTGTACAGTTT

AsnGlyThrMetArgIleValGlyProArgThrCysArgAsnMetTrpSerGlyThrPhe
6121   AACGGGACGATGAGGATCGTCGGTCCTAGGACCTGCAGGAACATGTGGAGTGGGACCTTC
       TTGCCCTGCTACTCCTAGCAGCCAGGATCCTGGACGTCCTTGTACACCTCACCCTGGAAG

ProIleAsnAlaTyrThrThrGlyProCysThrProLeuProAlaProAsnTyrThrPhe
6181   CCCATTAATGCCTACACCACGGGCCCCTGTACCCCCCTTCCTGCGCCGAACTACACGTTC
       GGGTAATTACGGATGTGGTGCCCGGGGACATGGGGGGAAGGACGCGGCTTGATGTGCAAG

AlaLeuTrpArgValSerAlaGluGluTyrValGluIleArgGlnValGlyAspPheHis
6241   GCGCTATGGAGGGTGTCTGCAGAGGAATATGTGGAGATAAGGCAGGTGGGGGACTTCCAC
       CGCGATACCTCCCACAGACGTCTCCTTATACACCTCTATTCCGTCCACCCCCTGAAGGTG

TyrValThrGlyMetThrThrAspAsnLeuLysCysProCysGlnValProSerProGlu
6301   TACGTGACGGGTATGACTACTGACAATCTCAAATGCCCGTGCCAGGTCCCATCGCCCGAA
       ATGCACTGCCCATACTGATGACTGTTAGAGTTTACGGGCACGGTCCAGGGTAGCGGGCTT

PhePheThrGluLeuAspGlyValArgLeuHisArgPheAlaProProCysLysProLeu
6361   TTTTTCACAGAATTGGACGGGGTGCGCCTACATAGGTTTGCGCCCCCCTGCAAGCCCTTG
       AAAAAGTGTCTTAACCTGCCCCACGCGGATGTATCCAAACGCGGGGGGACGTTCGGGAAC

LeuArgGluGluValSerPheArgValGlyLeuHisGluTyrProValGlySerGlnLeu
6421   CTGCGGGAGGAGGTATCATTCAGAGTAGGACTCCACGAATACCCGGTAGGGTCGCAATTA
       GACGCCCTCCTCCATAGTAAGTCTCATCCTGAGGTGCTTATGGGCCATCCCAGCGTTAAT

ProCysGluProGluProAspValAlaValLeuThrSerMetLeuThrAspProSerHis
6481   CCTTGCGAGCCCGAACCGGACGTGGCCGTGTTGACGTCCATGCTCACTGATCCCTCCCAT
       GGAACGCTCGGGCTTGGCCTGCACCGGCACAACTGCAGGTACGAGTGACTAGGGAGGGTA

IleThrAlaGluAlaAlaGlyArgArgLeuAlaArgGlySerProProSerValAlaSer
6541   ATAACAGCAGAGGCGGCCGGGCGAAGGTTGGCGAGGGGATCACCCCCCTCTGTGGCCAGC
       TATTGTCGTCTCCGCCGGCCCGCTTCCAACCGCTCCCCTAGTGGGGGGAGACACCGGTCG

SerSerAlaSerGlnLeuSerAlaProSerLeuLysAlaThrCysThrAlaAsnHisAsp
6601   TCCTCGGCTAGCCAGCTATCCGCTCCATCTCTCAAGGCAACTTGCACCGCTAACCATGAC
       AGGAGCCGATCGGTCGATAGGCGAGGTAGAGAGTTCCGTTGAACGTGGCGATTGGTACTG

SerProAspAlaGluLeuIleGluAlaAsnLeuLeuTrpArgGlnGluMetGlyGlyAsn
6661   TCCCCTGATGCTGAGCTCATAGAGGCCAACCTCCTATGGAGGCAGGAGATGGGCGGCAAC
       AGGGGACTACGACTCGAGTATCTCCGGTTGGAGGATACCTCCGTCCTCTACCCGCCGTTG
```

FIG. II

```
            IleThrArgValGluSerGluAsnLysValValIleLeuAspSerPheAspProLeuVal
6721        ATCACCAGGGTTGAGTCAGAAAACAAAGTGGTGATTCTGGACTCCTTCGATCCGCTTGTG
            TAGTGGTCCCAACTCAGTCTTTTGTTTCACCACTAAGACCTGAGGAAGCTAGGCGAACAC

AlaGluGluAspGluAlaGluIleSerValProAlaGluIleLeuArgLysSerArgArg
6781        GCGGAGGAGGACGAGCGGGAGATCTCCGTACCCGCAGAAATCCTGCGGAAGTCTCGGAGA
            CGCCTCCTCCTGCTCGCCCTCTAGAGGCATGGGCGTCTTTAGGACGCCTTCAGAGCCTCT

PheAlaGlnAlaLeuProValTrpAlaArgProAspTyrAsnProProLeuValGluThr
6841        TTCGCCCAGGCCCTGCCCGTTTGGGCGCGGCCGGACTATAACCCCCCGCTAGTGGAGACG
            AAGCGGGTCCGGGACGGGCAAACCCGCGCCGGCCTGATATTGGGGGGCGATCACCTCTGC

TrpLysLysProAspTyrGluProProValValHisGlyCysProLeuProProProLys
6901        TGGAAAAAGCCCGACTACGAACCACCTGTGGTCCATGGCTGTCCGCTTCCACCTCCAAAG
            ACCTTTTTCGGGCTGATGCTTGGTGGACACCAGGTACCGACAGGCGAAGGTGGAGGTTTC

SerProProValProProProArgLysLysArgThrValValLeuThrGluSerThrLeu
6961        TCCCCTCCTGTGCCTCCGCCCTCGGAAGAAGCGGACGGTGGTCCTCACTGAATCAACCCTA
            AGGGGAGGACACGGAGGCGGAGCCTTCTTCGCCTGCCACCAGGAGTGACTTAGTTGGGAT (Ser)
            SerThrAlaLeuAlaGluLeuAlaThrArgSerPheGlySerSerSerThrSerGlyIle
7021        TCTACTGCCTTGGCCGAGCTCGCCACCAGAAGCTTTGGCAGCTCCTCAACTTCCGGCATT
            AGATGACGGAACCGGCTCGAGCGGTGGTCTTCGAAACCGTCGAGGAGTTGAAGGCCGTAA

ThrGlyAspAsnThrThrThrSerSerGluProAlaProSerGlyCysProProAspSer
7081        ACGGGCGACAATACGACAACATCCTCTGAGCCCGCCCCTTCTGGCTGCCCCCCCGACTCC
            TGCCCGCTGTTATGCTGTTGTAGGAGACTCGGGCGGGGAAGACCGACGGGGGGGCTGAGG (PheAla)
            AspAlaGluSerTyrSerSerMetProProLeuGluGlyGluProGlyAspProAspLeu
7141        GACGCTGAGTCCTATTCCTCCATGCCCCCCCTGGAGGGGGAGCCTGGGGATCCGGATCTT
            CTGCGACTCAGGATAAGGAGGTACGGGGGGGACCTCCCCCTCGGACCCCTAGGCCTAGAA

SerAspGlySerTrpSerThrValSerSerGluAlaAsnAlaGluAspValValCysCys
7201        AGCGACGGGTCATGGTCAACGGTCAGTAGTGAGGCCAACGCGGAGGATGTCGTGTGCTGC
            TCGCTGCCCAGTACCAGTTGCCAGTCATCACTCCGGTTGCGCCTCCTACAGCACACGACG

SerMetSerTyrSerTrpThrGlyAlaLeuValThrProCysAlaAlaGluGluGlnLys
7261        TCAATGTCTTACTCTTGGACAGGCGCACTCGTCACCCCGTGCGCCGCGGAAGAACAGAAA
            AGTTACAGAATGAGAACCTGTCCGCGTGAGCAGTGGGGCACGCGGCGCCTTCTTGTCTTT

LeuProIleAsnAlaLeuSerAsnSerLeuLeuArgHisHisAsnLeuValTyrSerThr
7321        CTGCCCATCAATGCACTAAGCAACTCGTTGCTACGTCACCACAATTTGGTGTATTCCACC
            GACGGGTAGTTACGTGATTCGTTGAGCAACGATGCAGTGGTGTTAAACCACATAAGGTGG

ThrSerArgSerAlaCysGlnArgGlnLysLysValThrPheAspArgLeuGlnValLeu
7381        ACCTCACGCAGTGCTTGCCAAAGGCAGAAGAAAGTCACATTTGACAGACTGCAAGTTCTG
            TGGAGTGCGTCACGAACGGTTTCCGTCTTCTTTCAGTGTAAACTGTCTGACGTTCAAGAC

AspSerHisTyrGlnAspValLeuLysGluValLysAlaAlaAlaSerLysValLysAla
7441        GACAGCCATTACCAGGACGTACTCAAGGAGGTTAAAGCAGCGGCGTCAAAAGTGAAGGCT
            CTGTCGGTAATGGTCCTGCATGAGTTCCTCCAATTTCGTCGCCGCAGTTTTCACTTCCGA
```

FIG. IJ

```
                (Phe)
       AsnLeuLeuSerValGluGluAlaCysSerLeuThrProProHisSerAlaLysSerLys
7501   AACTTGCTATCCGTAGAGGAAGCTTGCAGCCTGACGCCCCACACTCAGCCAAATCCAAG
       TTGAACGATAGGCATCTCCTTCGAACGTCGGACTGCGGGGGTGTGAGTCGGTTTAGGTTC

PheGlyTyrGlyAlaLysAspValArgCysHisAlaArgLysAlaValThrHisIleAsn
7561   TTTGGTTATGGGGCAAAAGACGTCCGTTGCCATGCCAGAAAGGCCGTAACCCACATCAAC
       AAACCAATACCCCGTTTTCTGCAGGCAACGGTACGGTCTTTCCGGCATTGGGTGTAGTTG

SerValTrpLysAspLeuLeuGluAspAsnValThrProIleAspThrThrIleMetAla
7621   TCCGTGTGGAAAGACCTTCTGGAAGACAATGTAACACCAATAGACACTACCATCATGGCT
       AGGCACACCTTTCTGGAAGACCTTCTGTTACATTGTGGTTATCTGTGATGGTAGTACCGA

LysAsnGluValPheCysValGlnProGluLysGlyGlyArgLysProAlaArgLeuIle
7681   AAGAACGAGGTTTTCTGCGTTCAGCCTGAGAAGGGGGGTCGTAAGCCAGCTCGTCTCATC
       TTCTTGCTCCAAAAGACGCAAGTCGGACTCTTCCCCCCAGCATTCGGTCGAGCAGAGTAG

ValPheProAspLeuGlyValArgValCysGluLysMetAlaLeuTyrAspValValThr
7741   GTGTTCCCCGATCTGGGCGTGCGCGTGTGCGAAAAGATGGCTTTGTACGACGTGGTTACA
       CACAAGGGGCTAGACCCGCACGCGCACACGCTTTTCTACCGAAACATGCTGCACCAATGT

LysLeuProLeuAlaValMetGlySerSerTyrGlyPheGlnTyrSerProGlyGlnArg
7801   AAGCTCCCCTTGGCCGTGATGGGAAGCTCCTACGGATTCCAATACTCACCAGGACAGCGG
       TTCGAGGGGAACCGGCACTACCCTTCGAGGATGCCTAAGGTTATGAGTGGTCCTGTCGCC

ValGluPheLeuValGlnAlaTrpLysSerLysLysThrProMetGlyPheSerTyrAsp
7861   GTTGAATTCCTCGTGCAAGCGTGGAAGTCCAAGAAAACCCCAATGGGGTTCTCGTATGAT
       CAACTTAAGGAGCACGTTCGCACCTTCAGGTTCTTTTGGGGTTACCCCAAGAGCATACTA

ThrArgCysPheAspSerThrValThrGluSerAspIleArgThrGluGluAlaIleTyr
7921   ACCCGCTGCTTTGACTCCACAGTCACTGAGAGCGACATCCGTACGGAGGAGGCAATCTAC
       TGGGCGACGAAACTGAGGTGTCAGTGACTCTCGCTGTAGGCATGCCTCCTCCGTTAGATG

GlnCysCysAspLeuAspProGlnAlaArgValAlaIleLysSerLeuThrGluArgLeu
7981   CAATGTTGTGACCTCGACCCCAAGCCCGCGTGGCCATCAAGTCCCTCACCGAGAGGCTT
       GTTACAACACTGGAGCTGGGGGTTCGGGCGCACCGGTAGTTCAGGGAGTGGCTCTCCGAA (Gly)
       TyrValGlyGlyProLeuThrAsnSerArgGlyGluAsnCysGlyTyrArgArgCysArg
8041   TATGTTGGGGGCCCTCTTACCAATTCAAGGGGGGAGAACTGCGGCTATCGCAGGTGCCGC
       ATACAACCCCCGGGAGAATGGTTAAGTTCCCCCCTCTTGACGCCGATAGCGTCCACGGCG

AlaSerGlyValLeuThrThrSerCysGlyAsnThrLeuThrCysTyrIleLysAlaArg
8101   GCGAGCGGCGTACTGACAACTAGCTGTGGTAACACCCTCACTTGCTACATCAAGGCCCGG
       CGCTCGCCGCATGACTGTTGATCGACACCATTGTGGGAGTGAACGATGTAGTTCCGGGCC

AlaAlaCysArgAlaAlaGlyLeuGlnAspCysThrMetLeuValCysGlyAspAspLeu
8161   GCAGCCTGTCGAGCCGCAGGGCTCCAGGACTGCACCATGCTCGTGTGTGGCGACGACTTA
       CGTCGGACAGCTCGGCGTCCCGAGGTCCTGACGTGGTACGAGCACACACCGCTGCTGAAT

ValValIleCysGluSerAlaGlyValGlnGluAspAlaAlaSerLeuArgAlaPheThr
8221   GTCGTTATCTGTGAAAGCGCGGGGGTCCAGGAGGACGCGGCGAGCCTGAGAGCCTTCACG
       CAGCAATAGACACTTTCGCGCCCCCAGGTCCTCCTGCGCCGCTCGGACTCTCGGAAGTGC
```

FIG. IK

```
         GluAlaMetThrArgTyrSerAlaProProGlyAspProProGlnProGluTyrAspLeu
  8281   GAGGCTATGACCAGGTACTCCGCCCCCCTGGGGACCCCCCACAACCAGAATACGACTTG
         CTCCGATACTGGTCCATGAGGCGGGGGGGACCCCTGGGGGGTGTTGGTCTTATGCTGAAC

GluLeuIleThrSerCysSerSerAsnValSerValAlaHisAspGlyAlaGlyLysArg
  8341   GAGCTCATAACATCATGCTCCTCCAACGTGTCAGTCGCCCACGACGGCGCTGGAAAGAGG
         CTCGAGTATTGTAGTACGAGGAGGTTGCACAGTCAGCGGGTGCTGCCGCGACCTTTCTCC

ValTyrTyrLeuThrArgAspProThrThrProLeuAlaArgAlaAlaTrpGluThrAla
  8401   GTCTACTACCTCACCCGTGACCCTACAACCCCCCTCGCGAGAGCTGCGTGGGAGACAGCA
         CAGATGATGGAGTGGGCACTGGGATGTTGGGGGGAGCGCTCTCGACGCACCCTCTGTCGT

ArgHisThrProValAsnSerTrpLeuGlyAsnIleIleMetPheAlaProThrLeuTrp
  8461   AGACACACTCCAGTCAATTCCTGGCTAGGCAACATAATCATGTTTGCCCCCACACTGTGG
         TCTGTGTGAGGTCAGTTAAGGACCGATCCGTTGTATTAGTACAAACGGGGGTGTGACACC

AlaArgMetIleLeuMetThrHisPhePheSerValLeuIleAlaArgAspGlnLeuGlu
  8521   GCGAGGATGATACTGATGACCCATTTCTTTAGCGTCCTTATAGCCAGGGACCAGCTTGAA
         CGCTCCTACTATGACTACTGGGTAAAGAAATCGCAGGAATATCGGTCCCTGGTCGAACTT

GlnAlaLeuAspCysGluIleTyrGlyAlaCysTyrSerIleGluProLeuAspLeuPro
  8581   CAGGCCCTCGATTGCGAGATCTACGGGGCCTGCTACTCCATAGAACCACTTGATCTACCT
         GTCCGGGAGCTAACGCTCTAGATGCCCCGGACGATGAGGTATCTTGGTGAACTAGATGGA

ProIleIleGlnArgLeuHisGlyLeuSerAlaPheSerLeuHisSerTyrSerProGly
  8641   CCAATCATTCAAAGACTCCATGGCCTCAGCGCATTTTCACTCCACAGTTACTCTCCAGGT
         GGTTAGTAAGTTTCTGAGGTACCGGAGTCGCGTAAAAGTGAGGTGTCAATGAGAGGTCCA

GluIleAsnArgValAlaAlaCysLeuArgLysLeuGlyValProProLeuArgAlaTrp
  8701   GAAATTAATAGGGTGGCCGCATGCCTCAGAAAACTTGGGGTACCGCCCTTGCGAGCTTGG
         CTTTAATTATCCCACCGGCGTACGGAGTCTTTTGAACCCCATGGCGGGAACGCTCGAACC

Gly
         ArgHisArgAlaArgSerValArgAlaArgLeuLeuAlaArgGlyGlyArgAlaAlaIle
  8761   AGACACCGGGCCCGGAGCGTCCGCGCTAGGCTTCTGGCCAGAGGAGGCAGGGCTGCCATA
         TCTGTGGCCCGGGCCTCGCAGGCGCGATCCGAAGACCGGTCTCCTCCGTCCCGACGGTAT

CysGlyLysTyrLeuPheAsnTrpAlaValArgThrLysLeuLysLeuThrProIleAla
  8821   TGTGGCAAGTACCTCTTCAACTGGGCAGTAAGAACAAAGCTCAAACTCACTCCAATAGCG
         ACACCGTTCATGGAGAAGTTGACCCGTCATTCTTGTTTCGAGTTTGAGTGAGGTTATCGC

AlaAlaGlyGlnLeuAspLeuSerGlyTrpPheThrAlaGlyTyrSerGlyGlyAspIle
  8881   GCCGCTGGCCAGCTGGACTTGTCCGGCTGGTTCACGGCTGGCTACAGCGGGGGAGACATT
         CGGCGACCGGTCGACCTGAACAGGCCGACCAAGTGCCGACCGATGTCGCCCCCTCTGTAA (Pro)
         TyrHisSerValSerHisAlaArgProArgTrpIleTrpPheCysLeuLeuLeuLeuAla
  8941   TATCACAGCGTGTCTCATGCCCGGCCCCGCTGGATCTGGTTTTGCCTACTCCTGCTTGCT
         ATAGTGTCGCACAGAGTACGGGCCGGGGCGACCTAGACCAAAACGGATGAGGACGAACGA

AlaGlyValGlyIleTyrLeuLeuProAsnArgOP
  9001   GCAGGGGTAGGCATCTACCTCCTCCCCAACCGATGAAGGTTGGGGTAAACACTCCGGCCT
         CGTCCCCATCCGTAGATGGAGGAGGGGTTGGCTACTTCCAACCCCATTTGTGAGGCCGGA
```

FIG. 1L

Coding:  aa 1-154      hSOD
         aa 155-159    linker
         aa 160-899    c200 [aa HCV1 1192-1931]
         aa 900-902    linker
         aa 903-1021   c22 [aa HCV1 2-120]

Translation of SODc200core

```
  1                                               10
Met Ala Thr Lys Ala Val Cys Val Leu Lys Gly Asp Gly Pro Val
ATG GCT ACA AAG GCT GTT TGT GTT TTG AAG GGT GAC GGC CCA GTT 20                                30
Gln Gly Ile Ile Asn Phe Glu Gln Lys Glu Ser Asn Gly Pro Val
CAA GGT ATT ATT AAC TTC GAG CAG AAG GAA AGT AAT GGA CCA GTG

40
Lys Val Trp Gly Ser Ile Lys Gly Leu Thr Glu Gly Leu His Gly
AAG GTG TGG GGA AGC ATT AAA GGA CTG ACT GAA GGC CTG CAT GGA 50                                            60
Phe His Val His Glu Phe Gly Asp Asn Thr Ala Gly Cys Thr Ser
TTC CAT GTT CAT GAG TTT GGA GAT AAT ACA GCA GGC TGT ACC AGT

70
Ala Gly Pro His Phe Asn Pro Leu Ser Arg Lys His Gly Gly Pro
GCA GGT CCT CAC TTT AAT CCT CTA TCC AGA AAA CAC GGT GGG CCA 80                                        90
Lys Asp Glu Glu Arg His Val Gly Asp Leu Gly Asn Val Thr Ala
AAG GAT GAA GAG AGG CAT GTT GGA GAC TTG GGC AAT GTG ACT GCT

100
Asp Lys Asp Gly Val Ala Asp Val Ser Ile Glu Asp Ser Val Ile
GAC AAA GAT GGT GTG GCC GAT GTG TCT ATT GAA GAT TCT GTG ATC 110                                           120
Ser Leu Ser Gly Asp His Cys Ile Ile Gly Arg Thr Leu Val Val
TCA CTC TCA GGA GAC CAT TGC ATC ATT GGC CGC ACA CTG GTG GTC

130
His Glu Lys Ala Asp Asp Leu Gly Lys Gly Gly Asn Glu Glu Ser
CAT GAA AAA GCA GAT GAC TTG GGC AAA GGT GGA AAT GAA GAA AGT 140                                       150
Thr Lys Thr Gly Asn Ala Gly Ser Arg Leu Ala Cys Gly Val Ile
ACA AAG ACA GGA AAC GCT GGA AGT CGT TTG GCT TGT GGT GTA ATT

*                           *160
Gly Ile Ala Gln*Asn Leu Glu Phe Gly*Ala Val Asp Phe Ile Pro
GGG ATC GCC CAG*AAT TTG GAA TTC GGG*GCG GTG GAC TTT ATC CCT
```

FIG. 4A

```
                          170                                                    180
Val Glu Asn Leu Glu Thr Thr Met Arg Ser Pro Val Phe Thr Asp
GTG GAG AAC CTA GAG ACA ACC ATG AGG TCC CCG GTG TTC ACG GAT

190
Asn Ser Ser Pro Pro Val Val Pro Gln Ser Phe Gln Val Ala His
AAC TCC TCT CCA CCA GTA GTG CCC CAG AGC TTC CAG GTG GCT CAC 200                                            210
Leu His Ala Pro Thr Gly Ser Gly Lys Ser Thr Lys Val Pro Ala
CTC CAT GCT CCC ACA GGC AGC GGC AAA AGC ACC AAG GTC CCG GCT

220
Ala Tyr Ala Ala Gln Gly Tyr Lys Val Leu Val Leu Asn Pro Ser
GCA TAT GCA GCT CAG GGC TAT AAG GTG CTA GTA CTC AAC CCC TCT 230                                                240
Val Ala Ala Thr Leu Gly Phe Gly Ala Tyr Met Ser Lys Ala His
GTT GCT GCA ACA CTG GGC TTT GGT GCT TAC ATG TCC AAG GCT CAT

250
Gly Ile Asp Pro Asn Ile Arg Thr Gly Val Arg Thr Ile Thr Thr
GGG ATC GAT CCT AAC ATC AGG ACC GGG GTG AGA ACA ATT ACC ACT 260                                           270
Gly Ser Pro Ile Thr Tyr Ser Thr Tyr Gly Lys Phe Leu Ala Asp
GGC AGC CCC ATC ACG TAC TCC ACC TAC GGC AAG TTC CTT GCC GAC

280
Gly Gly Cys Ser Gly Gly Ala Tyr Asp Ile Ile Ile Cys Asp Glu
GGC GGG TGC TCG GGG GGC GCT TAT GAC ATA ATA ATT TGT GAC GAG 290                                        300
Cys His Ser Thr Asp Ala Thr Ser Ile Leu Gly Ile Gly Thr Val
TGC CAC TCC ACG GAT GCC ACA TCC ATC TTG GGC ATC GGC ACT GTC

310
Leu Asp Gln Ala Glu Thr Ala Gly Ala Arg Leu Val Val Leu Ala
CTT GAC CAA GCA GAG ACT GCG GGG GCG AGA CTG GTT GTG CTC GCC 320                                            330
Thr Ala Thr Pro Pro Gly Ser Val Thr Val Pro His Pro Asn Ile
ACC GCC ACC CCT CCG GGC TCC GTC ACT GTG CCC CAT CCC AAC ATC

340
Glu Glu Val Ala Leu Ser Thr Thr Gly Glu Ile Pro Phe Tyr Gly
GAG GAG GTT GCT CTG TCC ACC ACC GGA GAG ATC CCT TTT TAC GGC 350                                        360
Lys Ala Ile Pro Leu Glu Val Ile Lys Gly Gly Arg His Leu Ile
AAG GCT ATC CCC CTC GAA GTA ATC AAG GGG GGG AGA CAT CTC ATC

370
Phe Cys His Ser Lys Lys Lys Cys Asp Glu Leu Ala Ala Lys Leu
TTC TGT CAT TCA AAG AAG AAG TGC GAC GAA CTC GCC GCA AAG CTG
```

FIG. 4B

```
                        380                                                     390
    Val Ala Leu Gly Ile Asn Ala Val Ala Tyr Tyr Arg Gly Leu Asp
    GTC GCA TTG GGC ATC AAT GCC GTG GCC TAC TAC CGC GGT CTT GAC

400
    Val Ser Val Ile Pro Thr Ser Gly Asp Val Val Val Val Ala Thr
    GTG TCC GTC ATC CCG ACC AGC GGC GAT GTT GTC GTC GTG GCA ACC 410                                         420
    Asp Ala Leu Met Thr Gly Tyr Thr Gly Asp Phe Asp Ser Val Ile
    GAT GCC CTC ATG ACC GGC TAT ACC GGC GAC TTC GAC TCG GTG ATA

430
    Asp Cys Asn Thr Cys Val Thr Gln Thr Val Asp Phe Ser Leu Asp
    GAC TGC AAT ACG TGT GTC ACC CAG ACA GTC GAT TTC AGC CTT GAC 440                                                 450
    Pro Thr Phe Thr Ile Glu Thr Ile Thr Leu Pro Gln Asp Ala Val
    CCT ACC TTC ACC ATT GAG ACA ATC ACG CTC CCC CAG GAT GCT GTC

460
    Ser Arg Thr Gln Arg Arg Gly Arg Thr Gly Arg Gly Lys Pro Gly
    TCC CGC ACT CAA CGT CGG GGC AGG ACT GGC AGG GGG AAG CCA GGC 470                                         480
    Ile Tyr Arg Phe Val Ala Pro Gly Glu Arg Pro Ser Gly Met Phe
    ATC TAC AGA TTT GTG GCA CCG GGG GAG CGC CCC TCC GGC ATG TTC

490
    Asp Ser Ser Val Leu Cys Glu Cys Tyr Asp Ala Gly Cys Ala Trp
    GAC TCG TCC GTC CTC TGT GAG TGC TAT GAC GCA GGC TGT GCT TGG 500                                                 510
    Tyr Glu Leu Thr Pro Ala Glu Thr Thr Val Arg Leu Arg Ala Tyr
    TAT GAG CTC ACG CCC GCC GAG ACT ACA GTT AGG CTA CGA GCG TAC

520
    Met Asn Thr Pro Gly Leu Pro Val Cys Gln Asp His Leu Glu Phe
    ATG AAC ACC CCG GGG CTT CCC GTG TGC CAG GAC CAT CTT GAA TTT 530                                             540
    Trp Glu Gly Val Phe Thr Gly Leu Thr His Ile Asp Ala His Phe
    TGG GAG GGC GTC TTT ACA GGC CTC ACT CAT ATA GAT GCC CAC TTT

550
    Leu Ser Gln Thr Lys Gln Ser Gly Glu Asn Leu Pro Tyr Leu Val
    CTA TCC CAG ACA AAG CAG AGT GGG GAG AAC CTT CCT TAC CTG GTA 560                                     570
    Ala Tyr Gln Ala Thr Val Cys Ala Arg Ala Gln Ala Pro Pro Pro
    GCG TAC CAA GCC ACC GTG TGC GCT AGG GCT CAA GCC CCT CCC CCA

580
    Ser Trp Asp Gln Met Trp Lys Cys Leu Ile Arg Leu Lys Pro Thr
    TCG TGG GAC CAG ATG TGG AAG TGT TTG ATT CGC CTC AAG CCC ACC
```

FIG. 4C

```
                    590                                              600
Leu His Gly Pro Thr Pro Leu Leu Tyr Arg Leu Gly Ala Val Gln
CTC CAT GGG CCA ACA CCC CTG CTA TAC AGA CTG GGC GCT GTT CAG

610
Asn Glu Ile Thr Leu Thr His Pro Val Thr Lys Tyr Ile Met Thr
AAT GAA ATC ACC CTG ACG CAC CCA GTC ACC AAA TAC ATC ATG ACA 620                                              630
Cys Met Ser Ala Asp Leu Glu Val Val Thr Ser Thr Trp Val Leu
TGC ATG TCG GCC GAC CTG GAG GTC GTC ACG AGC ACC TGG GTG CTC

640
Val Gly Gly Val Leu Ala Ala Leu Ala Ala Tyr Cys Leu Ser Thr
GTT GGC GGC GTC CTG GCT GCT TTG GCC GCG TAT TGC CTG TCA ACA 650                                              660
Gly Cys Val Val Ile Val Gly Arg Val Val Leu Ser Gly Lys Pro
GGC TGC GTG GTC ATA GTG GGC AGG GTC GTC TTG TCC GGG AAG CCG

670
Ala Ile Ile Pro Asp Arg Glu Val Leu Tyr Arg Glu Phe Asp Glu
GCA ATC ATA CCT GAC AGG GAA GTC CTC TAC CGA GAG TTC GAT GAG 680                                              690
Met Glu Glu Cys Ser Gln His Leu Pro Tyr Ile Glu Gln Gly Met
ATG GAA GAG TGC TCT CAG CAC TTA CCG TAC ATC GAG CAA GGG ATG

700
Met Leu Ala Glu Gln Phe Lys Gln Lys Ala Leu Gly Leu Leu Gln
ATG CTC GCC GAG CAG TTC AAG CAG AAG GCC CTC GGC CTC CTG CAG 710                                              720
Thr Ala Ser Arg Gln Ala Glu Val Ile Ala Pro Ala Val Gln Thr
ACC GCG TCC CGT CAG GCA GAG GTT ATC GCC CCT GCT GTC CAG ACC

730
Asn Trp Gln Lys Leu Glu Thr Phe Trp Ala Lys His Met Trp Asn
AAC TGG CAA AAA CTC GAG ACC TTC TGG GCG AAG CAT ATG TGG AAC 740                                              750
Phe Ile Ser Gly Ile Gln Tyr Leu Ala Gly Leu SEr Thr Leu Pro
TTC ATC AGT GGG ATA CAA TAC TTG GCG GGC TTG TCA ACG CTG CCT

760
Gly Asn Pro Ala Ile Ala Ser Leu Met Ala Phe Thr Ala Ala Val
GGT AAC CCC GCC ATT GCT TCA TTG ATG GCT TTT ACA GCT GCT GTC 770                                      780
Thr Ser Pro Leu Thr Thr Ser Gln Thr Leu Leu Phe Asn Ile Leu
ACC AGC CCA CTA ACC ACT AGC CAA ACC CTC CTC TTC AAC ATA TTG

790
Gly Gly Trp Val Ala Ala Gln Leu Ala Ala Pro Gly Ala Ala Thr
GGG GGG TGG GTG GCT GCC CAG CTC GCC GCC CCC GGT GCC GCT ACT
```

FIG. 4D

```
                800                                                              810
Ala Phe Val Gly Ala Gly Leu Ala Gly Ala Ala Ile Gly Ser Val
GCC TTT GTG GGC GCT GGC TTA GCT GGC GCC GCC ATC GGC AGT GTT

820
Gly Leu Gly Lys Val Leu Ile Asp Ile Leu Ala Gly Tyr Gly Ala
GGA CTG GGG AAG GTC CTC ATA GAC ATC CTT GCA GGG TAT GGC GCG 830                                              840
Gly Val Ala Gly Ala Leu Val Ala Phe Lys Ile Met Ser Gly Glu
GGC GTG GCG GGA GCT CTT GTG GCA TTC AAG ATC ATG AGC GGT GAG

850
Val Pro Ser Thr Glu Asp Leu Val Asn Leu Leu Pro Ala Ile Leu
GTC CCC TCC ACG GAG GAC CTG GTC AAT CTA CTG CCC GCC ATC CTC 860                                              870
Ser Pro Gly Ala Leu Val Val Gly Val Val Cys Ala Ala Ile Leu
TCG CCC GGA GCC CTC GTA GTC GGC GTG GTC TGT GCA GCA ATA CTG

880
Arg Arg His Val Gly Pro Gly Glu Gly Ala Val Gln Trp Met Asn
CGC CGG CAC GTT GGC CCA GGC GAG GGG GCA GTG CAG TGG ATG AAC

890                                                *900
Arg Leu Ile Ala Phe Ala Ser Arg Gly Asn His Val Ser Pro*Gly
CGG CTG ATA GCC TTC GCC TCA CGG GGG AAC CAT GTT TCA CCC*GGG

*                                910
Asn Ser*Ser Thr Asn Pro Lys Pro Gln Lys Lys Asn Lys Arg Asn
AAT TCC*AGC ACG AAT CCT AAA CCT CAA AAA AAA AAC AAA CGT AAC 920                                          930
Thr Asn Arg Arg Pro Gln Asp Val Lys Phe Pro Gly Gly Gly Gln
ACC AAC CGT CGC CCA CAG GAC GTC AAG TTC CCG GGT GGC GGT CAG

940
Ile Val Gly Gly Val Tyr Leu Leu Pro Arg Arg Gly Pro Arg Leu
ATC GTT GGT GGA GTT TAC TTG TTG CCG CGC AGG GGC CCT AGA TTG 950                                          960
Gly Val Arg Ala Thr Arg Lys Thr Ser Glu Arg Ser Gln Pro Arg
GGT GTG CGC GCG ACG AGA AAG ACT TCC GAG CGG TCG CAA CCT CGA

970
Gly Arg Arg Gln Pro Ile Pro Lys Ala Arg Arg Pro Glu Gly Arg
GGT AGA CGT CAG CCT ATC CCC AAG GCT CGT CGG CCC GAG GGC AGG 980                                              990
Thr Trp Ala Gln Pro Gly Tyr Pro Trp Pro Leu Tyr Gly Asn Glu
ACC TGG GCT CAG CCC GGG TAC CCT TGG CCC CTC TAT GGC AAT GAG

1000
Gly Cys Gly Trp Ala Gly Trp Leu Leu Ser Pro Arg Gly Ser Arg
GGC TGC GGG TGG GCG GGA TGG CTC CTG TCT CCC CGT GGC TCT CGG 1010                                         1020
Pro Ser Trp Gly Pro Thr Asp Pro Arg Arg Arg Ser Arg Asn Leu
CCT AGC TGG GGC CCC ACA GAC CCC CGG CGT AGG TCG CGC AAT TTG

1021
Gly OC
GGT TAA TGAGTCGAC
```

FIG. 4E

COMBINATIONS OF HEPATITIS C VIRUS (HCV) ANTIGENS FOR USE IN IMMUNOASSAYS FOR ANTI-HCV ANTIBODIES

REFERENCE TO RELATED APPLICATIONS

This application is a continuation-in-part of U.S. Ser. No. 07/504,352 (filed Apr. 4, 1990 now abandoned), which in its entirety is hereby incorporated herein by reference. U.S. Ser. No. 07/504,352 is a continuation-in-part (CIP) of U.S. patent application Ser. No. 07/355,002, filed May 18, 1989, now abandoned, which in turn is a CIP of the following U.S. patent applications, all of which are now abandoned:

| Ser. No. | Filing Date |
| --- | --- |
| 07/122,714 | 11/18/87 |
| 07/139,886 | 12/30/87 |
| 07/161,072 | 02/26/88 |
| 07/191,263 | 05/06/88 |
| 07/263,584 | 10/26/88 |
| 07/271,450 | 11/14/88 |
| (PCT/US88/04125) | 11/18/88 |
| 07/325,338 | 03/17/89 |
| 07/341,334 | 04/20/89 |
| 07/353,896 | 04/21/89. |

TECHNICAL FIELD

The present invention is in the field of immunoassays for HCV (previously called Non-A, Non-B hepatitis virus). More particularly, it concerns combinations of HCV antigens that permit broad range immunoassays for anti-HCV antibodies.

BACKGROUND

The disease known previously as Non-A, Non-B hepatitis (NANBH) was considered to be a transmissible disease or family of diseases that were believed to be viral-induced, and that were distinguishable from other forms of viral-associated liver diseases, including that caused by the known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). NANBH was first identified in transfused individuals. Transmission from man to chimpanzee and serial passage in chimpanzees provided evidence that NANBH was due to a transmissible infectious agent or agents. Epidemiologic evidence suggested that there may be three types of NANBH: a water-borne epidemic type; a blood-borne or parenterally transmitted type; and a sporadically occurring (community acquired) type. However, until recently, no transmissible agent responsible for NANBH had been identified, and clinical diagnosis and identification of NANBH had been accomplished primarily by exclusion of other viral markers. Among the methods used to detect putative NANBH antigens and antibodies were agar-gel diffusion, counterimmunoelectrophoresis, immunofluorescence microscopy, immune electron microscopy, radioimmunoassay, and enzyme-linked immunosorbent assay. However, none of these assays proved to be sufficiently sensitive, specific, and reproducible to be used as a diagnostic test for NANBH.

In 1987, scientists at Chiron Corporation (the owner of the present application) identified the first nucleic acid definitively linked to blood-borne NANBH. See, e.g., EPO Pub. No. 318,216; Houghton et al., Science 244:359 (1989). These publications describe the cloning of an isolate from a new viral class, hepatitis C virus (HCV), the prototype isolate described therein being named "HCV1." HCV is a Flavi-like virus, with an RNA genome.

U.S. patent application Ser. No. 456,637 (Houghton et al.), incorporated herein by reference, describes the preparation of various recombinant HCV polypeptides by expressing HCV cDNA and the screening of those polypeptides for immunological reactivity with sera from HCV patients. That limited screening showed that at least five of the polypeptides tested were very immunogenic; specifically, those identified as 5-1-1, C100, C33c, CA279a, and CA290a. Of these five polypeptides, 5-1-1 is located in the putative NS4 domain; C100 spans the putative NS3 and NS4 domains; C33c is located within the putative NS3 domain and CA279a and CA290a are located within the putative C domain. The screening also showed that no single polypeptide tested was immunologically reactive with all sera. Thus, improved tests, which react with all or more samples from HCV positive individuals, are desirable.

DISCLOSURE OF THE INVENTION

Applicants have carried out additional serological studies on HCV antigens that confirm that no single HCV polypeptide identified to date is immunologically reactive with all sera. This lack of a single polypeptide that is universally reactive with all sera from individuals with HCV may be due, inter alia, to strain-to-strain variation in HCV epitopes, variability in the humoral response from individual-to-individual and/or variation in serology with the state of the disease.

These additional studies have also enabled applicants to identify combinations of HCV antigens that provide more efficient detection of HCV antibodies than any single HCV polypeptide.

Accordingly, one aspect of this invention is a combination of antigens comprising:
(a) a first HCV antigen from the C domain; and
(b) at least one additional HCV antigen selected from the group consisting of
(i) an HCV antigen from the NS3 domain;
(ii) an HCV antigen from the NS4 domain;
(iii) an HCV antigen from the S domain; and
(iv) an HCV antigen from the NS5 domain.

In one embodiment, the combination of HCV antigens is in the form of a fusion protein comprised of the antigens. In an alternative embodiment, the combination of antigens is in the form of the individual antigens bound to a common solid matrix. In still another embodiment, the combination of antigens is in the form of a mixture of the individual antigens.

Another aspect of the invention is a method for detecting antibodies to HCV in a mammalian body component suspected of containing said antibodies comprising contacting said body component with the above-described combination of HCV antigens under conditions that permit antibody-antigen reaction and detecting the presence of immune complexes of said antibodies and said antigens.

Another aspect of the invention is a method for detecting antibodies to HCV in a mammalian body component suspected of containing said antibodies comprising contacting said body component with a panel of HCV antigens, simultaneously or sequentially, comprising:
(a) a first HCV antigen from the C domain; and
(b) at least one additional HCV antigen selected from the group consisting of (i) an HCV antigen from the NS3 domain;
(ii) an HCV antigen from the NS4 domain;
(iii) an HCV antigen from the S domain; and
(iv) an HCV antigen from the NS5 domain under conditions that permit antibody-antigen reaction and detecting the presence of immune complexes of said antibodies and said antigens.

Another aspect of the invention is a kit for carrying out an assay for detecting antibodies to HCV in a mammalian body component suspected of containing said antibodies comprising in packaged combination (a) said combination of HCV antigens;
(b) standard control reagents; and
(c) instructions for carrying out the assay.

BRIEF DESCRIPTION OF THE DRAWINGS

In the drawings:

FIG. 1 is the nucleotide sequence of the cDNA sense and anti-sense strand for the HCV polyprotein (SEQ ID NO: 9) and the amino acid sequence encoded by the sense strand (SEQ ID NO: 10).

FIG. 4 shows the coding sequence of pSOD/c200/core (SEQ ID NO: 11 & SEQ ID NO: 12).

MODES FOR CARRYING OUT THE INVENTION

Definitions

"HCV antigen" intends a polypeptide of at least about 5 amino acids, more usually at least about 8 to 10 amino acids that defines an epitope found in an isolate of HCV. Preferably, the epitope is unique to HCV. When an antigen is designated by an alphanumeric code, the epitope is from the HCV domain specified by the alphanumeric.

"Synthetic" as used to characterize an HCV antigen intends that the HCV antigen has either been isolated from native sources or man-made such as by chemical or recombinant synthesis.

Figure 2:
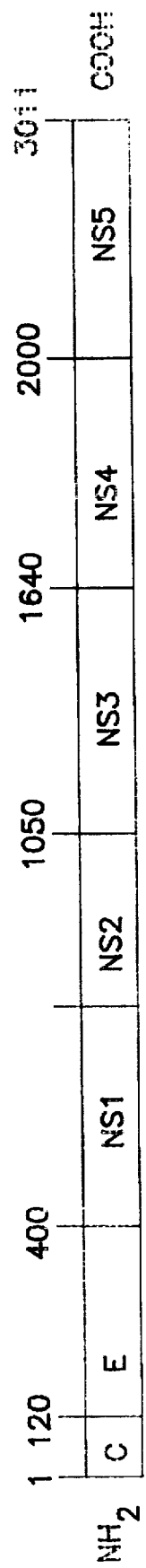
FIG. 2 is a schematic of the amino acid sequence of FIG. 1 showing the putative domains of the HCV polypeptide.

"Domains" intends those segments of the HCV polyprotein shown in FIG. 2 which generally correspond to the putative structural and nonstructural proteins of HCV. Domain designations generally follow the convention used to name Flaviviral proteins. The locations of the domains shown in FIG. 2 are only approximate. The designations "NS" denotes "nonstructural" domains, while "S" denotes the envelope domain, and "C" denotes the nucleocapsid or core domain.

"Fusion polypeptide" intends a polypeptide in which the HCV antigen(s) are part of a single continuous chain of amino acids, which chain does not occur in nature. The HCV antigens may be connected directly to each other by peptide bonds or be separated by intervening amino acid sequences. The fusion polypeptides may also contain amino acid sequences exogenous to HCV.

"Common solid matrix" intends a solid body to which the individual HCV antigens or the fusion polypeptide comprised of HCV antigens are bound covalently or by noncovalent means such as hydrophobic adsorption.

"Mammalian body component" intends a fluid or tissue of a mammalian individual (e.g., a human) that commonly contains antibodies produced by the individual. Such components are known in the art and include, without limitation, blood, plasma, serum, spinal fluid, lymph fluid, secretions of the respiratory, intestinal or genitourinary tracts, tears, saliva, milk, white blood cells, and myelomas.

"Immunologically reactive" means that the antigen in question will react specifically with anti-HCV antibody commonly present in a significant proportion of sera from individuals infected with HCV.

"Immune complex" intends the combination or aggregate formed when an antibody binds to an epitope on an antigen.

Combinations of HCV Antigens

FIG. 2 shows the putative domains of the HCV polyprotein. The domains from which the antigens used in the combinations derive are: C, S (or E), NS3, NS4, and NS5. The C domain is believed to define the nucleocapsid protein of HCV. It extends from the N-terminal of the polyprotein to approximately amino acid 120 of FIG. 1. The S domain is believed to define the virion envelope protein, and possibly the matrix (M) protein, and is believed to extend from approximately amino acid 120 to amino acid 400 of FIG. 1. The NS3 domain extends from approximately amino acid 1050 to amino acid 1640 and is believed to constitute the viral protease. The NS4 domain extends from the terminus of NS3 to approximately amino acid 2000. The function of the NS4 protein is not known at this time. Finally, the NS5 domain extends from about amino acid 2000 to the end of the polyprotein and is believed to define the viral polymerase.

The sequence shown in FIG. 1 is the sequence of the HCV1 isolate. It is expected that the sequences of other strains of the blood-borne HCV may differ from the sequence of FIG. 1, particularly in the envelope (S) and nucleocapsid (C) domains. The use of HCV antigens having such differing sequences is intended to be within the scope of the present invention, provided, however, that the variation does not significantly degrade the immunological reactivity of the antigen to sera from persons infected with HCV.

In general, the HCV antigens will comprise entire or truncated domains, the domain fragments being readily screened for antigenicity by those skilled in the art. The individual HCV antigens used in the combination will preferably comprise the immunodominant portion (i.e., the portion primarily responsible for the immunological reactivity of the polypeptide) of the stated domain. In the case of the C domain it is preferred that the C domain antigen comprise a majority of the entire sequence of the domain. The antigen designated C22 (see Example 4, infra), is particularly preferred. The S domain antigen preferably includes the hydrophobic subdomain at the N-terminal end of the domain. This hydrophobic subdomain extends from approximately amino acid 199 to amino acid 328 of FIG. 1. The HCV antigen designated S2 (see Example 3, infra), is particularly preferred. Sequence downstream of the hydrophobic subdomain may be included in the S domain antigen if desired.

A preferred NS3 domain antigen is the antigen designated C33c. That antigen includes amino acids 1192 to 1457 of FIG. 1. A preferred NS4 antigen is C100 which comprises amino acids 1569 to 1931 of FIG. 1. A preferred NS5 antigen comprises amino acids 2054 to 2464 of FIG. 1. Additional preferred S domain antigens are disclosed in commonly owned U.S. Pat. Ser. No. 07/910,759 (Attorney Docket No. 22300-20287.00), filed on even date herewith, entitled "Immunoassays for Anti-HCV Antibodies Using Antigens with Conformational Epitopes," by David Chien, and in U.S. Ser. No. 07/758,880, filed Sept. 13, 1991, and in WO92/08734, which are incorporated herein by reference.

The HCV antigen may be in the form of a polypeptide composed entirely of HCV amino acid sequence or it may contain sequence exogenous to HCV (i.e., it may be in the form of a fusion protein that includes exogenous sequence). In the case of recombinantly produced HCV antigen, producing the antigen as a fusion protein such as with SOD, alpha-factor or ubiquitin (see commonly owned U.S. Pat. No. 4,751,180, U.S. Pat. No. 4,870,008 and U.S. patent application Ser. No. 390,599, filed 7 Aug. 1989, the disclosures of which are incorporated herein, which describe expression of SOD, alpha-factor and ubiquitin fusion proteins) may increase the level of expression and/or increase the water solubility of the antigen. Fusion proteins such as the alpha-factor and ubiquitin fusion are processed by the expression host to remove the heterologous sequence. Alpha-factor is a secretion system, however, while ubiquitin fusions remain in the cytoplasm.

Further, the combination of antigens may be produced as a fusion protein. Generally, these fusions will combine epitopes from the C domain with one or more epitopes from the S, NS3, NS4 and/or NS5 domains (e.g., C/NS3/NS4 or C/NS5 or C/NS3/NS5). Another preferred class of fusions are those where the C domain epitopes are encoded at the carboxy end of the fusion protein (e.g., N'—NS3/NS4/CC'; N'—NS3/C—'; N'—NS5/C—C'; N'—NS3/NS4/NS5/C—C'; N'S/C—C'). For instance, a continuous fragment of DNA encoding C22 and C33c may be constructed, cloned into an expression vector and used to express a fusion protein of C22 and C33c. In a similar manner fusion proteins of C22 and C100; C22 and S2; C22 and an NS5 antigen; C22, C33c, and S2; C22, C100 and S2, and C22, C33c, C100, and S2 may be made. Examples of preferred fusion proteins are fusions with c200, such as c22/c200 and c200/c22. Alternative fragments from the exemplified domain may also be used.

Preparation of HCV Antigens

The HCV antigens of the invention are preferably produced recombinantly or by known solid phase chemical synthesis. They may, however, also be isolated from dissociated HCV or HCV particles using affinity chromatography techniques employing antibodies to the antigens.

When produced by recombinant techniques, standard procedures for constructing DNA encoding the antigen, cloning that DNA into expression vectors, transforming host cells such as bacteria, yeast, insect, or mammalian cells, and expressing such DNA to produce the antigen may be employed. As indicated previously, it may be desirable to express the antigen as a fusion protein to enhance expression, facilitate purification, or enhance solubility. Examples of specific procedures for producing representative HCV antigens are described in the Examples, infra, and in U.S. patent application Ser. No. 456,637, and in EPO Publication No. 318,216.

Formulation of Antigens for Use in Immunoassay

The HCV antigens may be combined by producing them in the form of a fusion protein composed of two or more of the antigens, by immobilizing them individually on a common solid matrix, or by physically mixing them. Fusion proteins of the antigen may also be immobilized on (bound to) a solid matrix. Methods and means for covalently or noncovalently binding proteins to solid matrices are known in the art. The nature of the solid surface will vary depending upon the assay format. For assays carried out in microtiter wells, the solid surface will be the wall of the well or cup. For assays using beads, the solid surface will be the surface of the bead. In assays using a dipstick (i.e., a solid body made from a porous or fibrous material such as fabric or paper) the surface will be the surface of the material from which the dipstick is made. In agglutination assays the solid surface may be the surface of latex or gelatin particles. When individual antigens are bound to the matrix they may be distributed homogeneously on the surface or distributed thereon in a pattern, such as bands so that a pattern of antigen binding may be discerned.

Simple mixtures of the antigens comprise the antigens in any suitable solvent or dispersing medium.

Assay Formats Using Combinations of Antigens

The HCV antigens may be employed in virtually any assay format that employs a known antigen to detect antibodies. A common feature of all of these assays is that the antigen is contacted with the body component suspected of containing HCV antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin, and enzyme-labeled and mediated immunoassays, such as ELISA assays.

The immunoassay may be, without limitation, in a heterogenous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immulon™), diazotized paper, nylon membranes, activated beads, and Protein A beads. For example, Dynatech Immulon™ 1 or Immulon™ 2 microtiter plates or 0.25 inch polysterene beads (Precision Plastic Ball) can be used in the heterogeneous format. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of HCV antibodies forming the antibody-antigen complex is directly monitored. This may be accomplished by determining whether labeled anti-xenogenic (e.g., anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

Complexes formed comprising anti-HCV antibody (or, in the case of competitive assays, the amount of competing antibody) are detected by any of a number of known techniques, depending on the format. For example, unlabeled HCV antibodies in the complex may be detected using a conjugate of antixenogeneic Ig complexed with a label, (e.g., an enzyme label).

In an immunoprecipitation or agglutination assay format the reaction between the HCV antigens and the antibody forms a network that precipitates from the solution or suspension and forms a visible layer or film of precipitate. If no anti-HCV antibody is present in the test specimen, no visible precipitate is formed.

The HCV antigens will typically be packaged in the form of a kit for use in these immunoassays. The kit will normally contain in separate containers the combination of antigens (either already bound to a solid matrix or separate with reagents for binding them to the matrix), control antibody formulations (positive and/or negative), labeled antibody when the assay format requires same and signal generating reagents (e.g., enzyme substrate) if the label does not generate a signal directly. Instructions (e.g., written, tape, VCR, CD-ROM, etc.) for carrying out the assay usually will be included in the kit.

The following examples are intended to illustrate the invention and are not intended to limit the invention in any manner.

Example 1: Synthesis of HCV Antigen C33c

HCV antigen C33c contains a sequence from the NS3 domain. Specifically, it includes amino acids 1192–1457 of FIG. 1. This antigen was produced in bacteria as a fusion protein with human superoxide dismutase (SOD) as follows. The vector pSODcf1 (Steiner et al. (1986), J. Virol. 58:9) was digested to completion with EcoRI and BamHI and the resulting EcoRI.BamHI fragment was ligated to the following linker to form pcf1EF:

GATC CTG GAA TTC TGA TAA (SEQ. ID NO:1)
GAC CTT AAG ACT ATT TTA A (SEQ. ID NO:2)

A CDNA clone endcoding amino acids 1192–1457 and having EcoRI ends was inserted into pcf1EF to form pcf1EF/C33c. This expression construct was transformed into D1210 *E. coli* cells.

The transformants were used to express a fusion protein comprised of SOD at the N-terminus and in-frame C33c HCV antigen at the C-terminus. Expression was accomplished by inoculating 1500 ml of Luria broth containing ampicillin (100 micrograms/ml) with 15 ml of an overnight culture of the transformants. The cells were grown to an O.D. of 0.3, IPTG was added to yield a final concentration of 2 mM, and growth continued until the cells attained a density of 1 O.D., at which time they were harvested by centrifugation at 3,000×g at 4° C. for 20 minutes. The packed cells can be stored at −80° C. for several months.

In order to purify the SOD-C33c polypeptide the bacterial cells in which the polypeptide was expressed were subjected to osmotic shock and mechanical disruption, the insoluble fraction containing SOD-C33c was isolated and subjected to differential extraction with an alkaline-NaCl solution, and the fusion polypeptide in the extract purified by chromatography on columns of S-Sepharose and Q-Sepharose.

The crude extract resulting from osmotic shock and mechanical disruption was prepared by the following procedure. One gram of the packed cells were suspended in 10 ml of a solution containing 0.02 M Tris HCl, pH 7.5, 10 mM EDTA, 20% sucrose, and incubated for 10 minutes on ice. The cells were then pelleted by centrifugation at 4,000×g for 15 min at 4° C. After the supernatant was removed, the cell pellets were resuspended in 10 ml of Buffer A1 (0.01M Tris HCl, pH 7.5, 1 mM EDTA, 14 mM beta-mercaptoethanol [BME]), and incubated on ice for 10 minutes. The cells were again pelleted at 4,000×g for 15 minutes at 4° C. After removal of the clear supernatant (periplasmic fraction I), the cell pellets were resuspended in Buffer A1, incubated on ice for 10 minutes, and again centrifuged at 4,000×g for 15 minutes at 4° C. The clear supernatant (periplasmic fraction II) was removed, and the cell pellet resuspended in 5 ml of Buffer A2 (0.02M Tris HCl, pH 7.5, 14 mM BME, 1 mM EDTA, 1 mM PMSF). In order to disrupt the cells, the suspension (5 ml) and 7.5 ml of Dyno-mill lead-free acid washed glass beads (0.10–0.15 mm diameter)(obtained from Glen-Mills, Inc.) were placed in a Falcon tube, and vortexed at top speed for two minutes, followed by cooling for at least 2 min on ice; the vortexing-cooling procedure was repeated another four times. After vortexing, the slurry was filtered through a scintered glass funnel using low suction; the glass beads were washed two times with Buffer A2, and the filtrate and washes combined.

The insoluble fraction of the crude extract was collected by centrifugation at 20,000×g for 15 min at 4° C., washed twice with 10 ml Buffer A2, and resuspended in 5 ml of MILLI-Q water.

A fraction containing SOD-C33c was isolated from the insoluble material by adding to the suspension NaOH (2M) and NaCl (2M) to yield a final concentration of 20 mM each, vortexing the mixture for 1 minute, centrifuging it 20,000×g for 20 min at 4° C., and retaining the supernatant.

In order to purify SOD-C33c on S-Sepharose, the supernatant fraction was adjusted to a final concentration of 6M urea, 0.05M Tris HCl, pH 7.5, 14 mM BME, 1 mM EDTA. This fraction was then applied to a column of S-Sepharose Fast Flow (1.5×10 cm) which had been equilibrated with Buffer B (0.05M Tris HCl, pH 7.5, 14 mM BME, 1 mM EDTA). After application, the column was washed with two column volumes of Buffer B. The flow through and wash fractions were collected. The flow rate of application and wash, was 1 ml/min; and collected fractions were 1 ml. In order to identify fractions containing SOD-C33c, aliquots of the fractions were analyzed by electrophoresis on 10% polyacrylamide gels containing SDS followed by staining with Coomassie blue. The fractions are also analyzable by Western blots using an antibody directed against SOD. Fractions containing SOD-C33c were pooled.

Further purification of SOD-C33c was on a Q-Sepharose column (1.5×5 cm) which was equilibrated with Buffer B. The pooled fractions containing SOD-C33c obtained from chromatography on S-Sepharose was applied to the column. The column was then washed with Buffer B, and eluted with 60 ml of a gradient of 0.0 to 0.4M NaCl in Buffer B. The flow rate for application, wash, and elution was 1 ml/min; collected fractions were 1 ml. All fractions from the Q-Sepharose column were analyzed as described for the S-Sepharose column. The peak of SOD-C33c eluted from the column at about 0.2M NaCl.

The SOD-C33c obtained from the Q-Sepharose column was greater than about 90% pure, as judged by analysis on the polyacrylamide SDS gels and immunoblot using a monoclonal antibody directed against human SOD.

Example 2: Synthesis of HCV Antigen C100

HCV antigen C100 contains sequences from the NS3 and NS4 domains (See EPO Pub. No. 318,216, Example IV.B.4-.6.) Specifically, it includes amino acids 1569–1931 of FIG. 1. This antigen was produced in yeast. A cDNA fragment of 1270 bp encoding the above amino acids and having EcoRI termini was prepared.

The construction of a yeast expression vector in which this fragment was fused directly to the *S. cerevisiae* ADH2/

GAP promoter was accomplished by a protocol which included amplification of the C100 sequence using a PCR method, followed by ligation of the amplified sequence into a cloning vector. After cloning, the C100 sequence was excised, and with a sequence which contained the ADH2/GAP promoter, was ligated to a large fragment of a yeast vector to yield a yeast expression vector.

The PCR amplification of C100 was performed using as template the vector pS3-56$_{C100m}$, which had been linearized by digestion with SalI. pS3-56, which is a pBR322 derivative, contains an expression cassette which is comprised of the ADH2/GAPDH hybrid yeast promoter upstream of the human superoxide dismutase gene, and a downstream alpha factor transcription terminator.

The oligonucleotide primers used for the amplification were designed to facilitate cloning into the expression vector, and to introduce a translation termination codon. Specifically, novel 5'-HindIII and 3'-SalI sites were generated with the PCR oligonucleotides. The oligonucleotide containing the SalI site also encodes the double termination codons, TAA and TGA. The oligonucleotide containing the HindIII site also contains an untranslated leader sequence derived from the pgap63 gene, situated immediately upstream of the AUG codon. The pEco63GAPDH gene is described by Holland and Holland (1980) and by Kniskern et al. (1986). The PCR primer sequences used for the direct expression of C100m were:

5' GAG TGC TCA AGC TTC AAA ACA AAA TGGCTC (SEQ. ID NO:3)
ACT TTC TAT CCC AGA CAA AGC AGA GT 3' and

5' GAG TGC TCG TCG ACT CAT TAG GGGGAA (SEQ. ID NO:4)
ACA TGG TTC CCC CGG GAG GCG AA 3'

Amplification by PCR, utilizing the primers, and template, was with a Cetus-Perkin-Elmer PCR kit, and was performed according to the manufacturer's directions. The PCR conditions were 29 cycles of 94° C. for a minute, 37° C. for 2 minutes, 72° C. for 3 minutes; and the final incubation was at 72° C. for 10 minutes. The DNA can be stored at 4° C. or −20° C. overnight.

After amplification, the PCR products were digested with HindIII and SalI. The major product of 1.1 kb was purified by electrophoresis on a gel, and the eluted purified product was ligated with a large SalI-HindIII fragment of pBR322. In order to isolate correct recombinants, competent HB101 cells were transformed with the recombinant vectors, and after cloning, the desired recombinants were identified on the basis of the predicted size of HindIII- SalI fragments excised from the clones. One of the clones which contained the a HindIII-SalI fragment of the correct size was named pBR322/C100⁻d. Confirmation that this clone contained amplified C100 was by direct sequence analysis of the HindIII-SalI fragment.

The expression vector containing C100 was constructed by ligating the HindIII-SalI fragment from pBR322/C100⁻d to a 13.1 kb BamHI-SalI fragment of pBS24.1, and a 1369 bm BamHI-HindIII fragment containing the ADH2/GAP promoter. (The latter fragment is described in EPO 164, 556). The pBS24.1 vector is described in commonly owned U.S. Ser. No. 382,805 filed 19 Jul. 1989. The ADH2/GAP promoter fragment was obtained by digestion of the vector pPGAP/AG/HindIII with HindIII and BamHI, followed by purification of the 1369 bp fragment on a gel.

Competent HB101 cells were transformed with the recombinant vectors; and correct recombinants were identified by the generation of a 2464 bp fragment and a 13.1 kb fragment generated by BamHI and SalI digestion of the cloned vectors. One of the cloned correct recombinant vectors was named pC100⁻d#3.

In order to express C100, competent cells of *Saccharomyces cerevisiae* strain AB122 (MATa leu2 ura3-53 prb 1-1122 pep4-3 prcl-407[cir-0]) were transformed with the expression vector pC100⁻d#3. The transformed cells were plated on URA-sorbitol, and individual transformants were then streaked on Leu⁻ plates.

Individual clones were cultured in Leu⁻, ura⁻ medium with 2% glucose at 30° C. for 24–36 hours. One liter of Yeast Extract Peptone Medium (YEP) containing 2% glucose was inoculated with 10 ml of the overnight culture, and the resulting culture was grown at 30° C. at an agitation rate of 400 rpm and an aeration rate of 1 L of air per 1 L of medium per minute (i.e., 1vvm) for 48 hours. The pH of the medium was not controlled. The culture was grown in a BioFlo II fermentor manufactured by New Brunswick Science Corp. Following fermentation, the cells were isolated and analyzed for C100 expression.

Analysis for expressed C100 polypeptide by the transformed cells was performed on total cell lysates and crude extracts prepared from single yeast colonies obtained from the Leu⁻ plates. The cell lysates and crude extracts were analyzed by electrophoresis on SDS polyacrylamide gels, and by Western blots. The Western blots were probed with rabbit polyclonal antibodies directed against the SOD-C100 polypeptide expressed in yeast. The expected size of the C100 polypeptide is 364 amino acids. By gel analysis the expressed polypeptide has a $MW_r$ of 39.9K.

Both analytical methods demonstrated that the expressed C100 polypeptide was present in total cell lysates, but was absent from crude extracts. These results suggest that the expressed C100 polypeptide may be insoluble.

Example 3: Expression of HCV Antigen S2

HCV antigen S2 contains a sequence from the hydrophobic N-terminus of the S domain. It includes amino acids 199–328 of FIG. 1.

The protocol for the construction of the expression vector encoding the S2 polypeptide and for its expression in yeast was analogous to that used for the expression of the C100 polypeptide, described in Example 2.

The template for the PCR reaction was the vector pBR322/Pi14a, which had been linearized by digestion with HindIII. Pi14a is a cDNA clone that encodes amino acids 199–328.

The oligonucleotides used as primers for the amplification by PCR of the S2 encoding sequence were the following.

For the 5'-region of the S2 sequence: (SEQ. ID NO:5)
5' GAG TGC TCA AGC TTC AAA ACA AAA TGG GGC TCT
ACC ACG TCA CCA ATG ATT GCC CTA AC 3';

and for the 3'-region of the S2 sequence: (SEQ. ID NO:5)
5' GAG TGC TCG TCG ACT CAT TAA GGG GAC CAG TTC
ATC ATC ATA TCC CAT GCC AT 3'

The primer for the 5'-region introduces a HindIII site and an ATG start codon into the amplified product. The primer for the 3'-region introduces translation stop codons and a SalI site into the amplified product.

The PCR conditions were 29 cycles of 94° C. for a minute, 37° C. for 2 minutes, 72° C. for 3 minutes, and the final incubation was at 72° C. for 10 minutes.

The main product of the PCR reaction was a 413 bp fragment, which was gel purified. The purified fragment was ligated to the large fragment obtained from pBR322 digested with HindIII and SalI fragment, yielding the plasmid pBR322/S2d.

Ligation of the 413 bp HindIII-SalI S2 fragment with the 1.36 kb BamHI-HindIII fragment containing the ADH2/

GAP promoter, and with the large BamHI-SalI fragment of the yeast vector pBS24.1 yielded recombinant vectors, which were cloned. Correct recombinant vectors were identified by the presence of a 1.77 kb fragment after digestion with BamHI and SalI. An expression vector constructed from the amplified sequence, and containing the sequence encoding S2 fused directly to the ADH2/GAP promoter is identified as pS2d#9.

Example 4: Synthesis of HCV C Antigen

HCV antigen C22 is from the C domain. It comprises amino acids 1–122 of FIG. 1.

The protocol for the construction of the expression vector encoding the C polypeptide and for its expression in yeast was analogous to that used for the expression of the C100 polypeptide, described supra, except for the following.

The template for the PCR reaction was pBR322/Ag30a which had been linearized with HindIII. Ag30 is a cDNA clone that encodes amino acids 1–122. The oligonucleotides used as primers for the amplification by PCR of the C encoding sequence were the following.

For the 5'-region of the C sequence: (SEQ. ID NO:7)
5' GAG TGC AGC TTC AAA ACA AAA TGA GCA CGA
    ATC CTA AAC CTC AAA AAA AAA AC 3' and for the 3'-region of the C sequence: (SEQ. ID NO:8)
5' GAG TGC TCG TCG ACT CAT TAA CCC AAA TTG CGC
    GAC CTA CGC CGG GGG TCT GT 3'.

The primer for the 5'-region introduces a HindIII site into the amplified product, and the primer for the 3'-region introduces translation stop codons and a SalI site. The PCR was run for 29 cycles of 94° C. for a minute, 37° C. for 2 minutes, 72° C. for 3 minutes, and the final incubation was at 72° C. for 10 minutes.

The major product of PCR amplification is a 381 bp polynucleotide. Ligation of this fragment with the SalI-HindIII large SalI-HindIII fragment of pBR322 yielded the plasmid pBR322/C2.

Ligation of the 381 bp HindIII-SalI C coding fragment excised from pBR322/C2 with the 1.36 kb BamHI-HindIII fragment containing the ADH2/GAP promoter, and with the large BamHI-SalI fragment of the yeast vector pBS24.1 yielded recombinant vectors, which were cloned. Correct recombinant vectors were identified by the presence of a 1.74 kb fragment after digestion with BamHI and SalI. An expression vector constructed from the amplified sequence, and containing the sequence encoding C fused directly to the ADH2/GAP promoter is identified as pC22.

Analysis for expressed C polypeptide by the transformed cells was performed on total cell lysates and crude extracts prepared from single yeast colonies obtained from the Leu⁻ plates. The cell lysates and crude extracts were analyzed by electrophoresis on SDS polyacrylamide gels. The C polypeptide is expected to have 122 amino acids and by gel analysis the expressed polypeptide has a $MW_r$ of approximately 13.6 Kd.

Example 5: Synthesis of NS5 Polypeptide

This polypeptide contains sequence from the N-terminus of the NS5 domain. Specifically it includes amino acids 2054 to 2464 of FIG. 1. The protocol for the construction of the expression vector encoding the NS5 polypeptide and for its expression were analogous to that used for the expression of C33c (see Example 1).

Another NS5 domain antigen was made by preparing a coding sequence for amino acids 2054–2995 of FIG. 1 and ligating it into a yeast SOD fusion expression vector (pSOD/NS5) in a manner analogous to Example 1 above and expressing it in *S. cerevisiae* strain JSC 308, as described in EPO Pub. No. 318,216, Examples IV.B.4-.6.

Example 6: Fusion Proteins

In addition to the c100 fusion protein described above, several other fusion proteins were prepared.

A fusion of NS3 and NS4 domains, called c200 was prepared. The c200 polypeptide spans amino acids 1192–1931 of FIG. 1. An expression plasmid pAB24-c200, which is a yeast SOD fusion expression vector containing a coding sequence for c200 was prepared in a manner analogous to the c100-3 vector in EPO Pub. No. 318,216, Example IV.B.4-.6, and expressed in *S. cerevisiae* JSC308. Id. c200 can be used in place of c100 in the above-described antigen panels. See also U.S. Pat. Ser. No. 07/456,637, filed 21 Dec. 1989, Examples IV.A.37 and IV.B.10, incorporated herein by reference.

A fusion of core, NS3 and NS4 called c22/c200 was prepared. The coding domain for the expression plasmid, pSOD/core/c200, encodes amino acids 2–120, 1192–1931 of FIG. 1. This plasmid, a yeast SOD expression vector for core fused to c200, was prepared in a manner analogous to Example 2, above, and expressed in *S. cerevisiae* JSC308.

Figure 3:
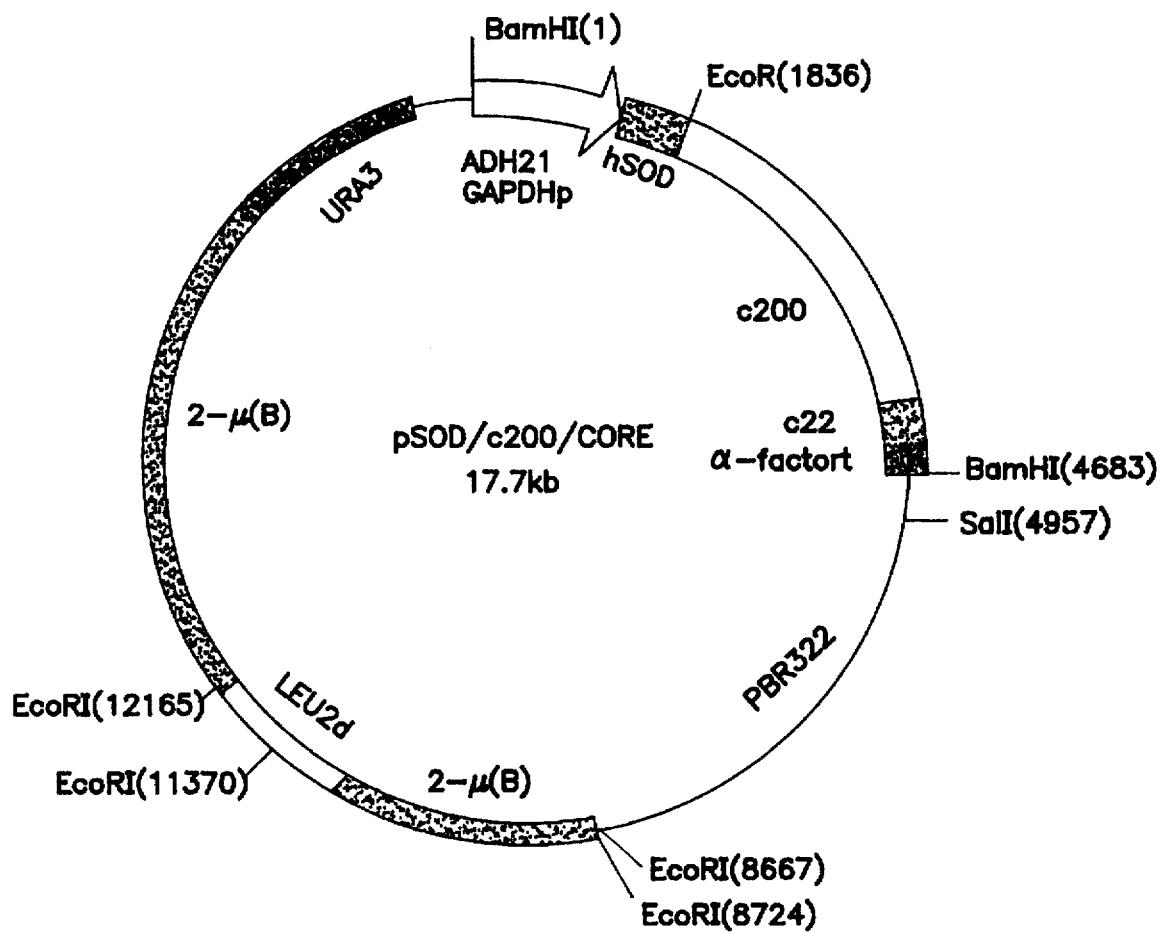
FIG. 3 is a map showing some of the features of the plasmid pSOD/c200/core.

A variation of the above fusion, called c200/c22, was also prepared. In this antigen, the core domain is located at the carboxy rather than the amino terminus of the protein. The expression plasmid, pSOD/c200/core (FIG. 3), has an HCV coding sequence for amino acids 1192–1931, 2–120 (FIG. 4). The vector was prepared as described in Example 2, above, and expressed in *S. cerevisiae* JSC 308.

Example 7: Radioimmunoassay (RIA) for Antibodies to HCV

The HCV antigens of Examples 1–5 were tested in an RIA format for their ability to detect antibodies to HCV in the serum of individuals clinically diagnosed as having HCV (Non-A, Non-B) and in serum from blood given by paid blood donors.

The RIA was based upon the procedure of Tsu and Herzenberg (1980) in SELECTED METHODS IN CELLULAR IMMUNOLOGY (W. H. Freeman & Co.), pp. 373–391. Generally, microtiter plates (Immulon 2, Removawell strips) are coated with purified HCV antigen. The coated plates are incubated with the serum samples or appropriate controls. During incubation, antibody, if present, is immunologically bound to the solid phase antigen. After removal of the unbound material and washing of the microtiter plates, complexes of human antibody-HCV antigen are detected by incubation with $^{125}$I-labeled sheep anti-human immunoglobulin. Unbound labeled antibody is removed by aspiration, and the plates are washed. The radioactivity in individual wells is determined; the amount of bound human anti-HCV antibody is proportional to the radioactivity in the well.

Specifically, one hundred microliter aliquots containing 0.1 to 0.5 micrograms of the HCV antigen in 0.125M Na borate buffer, pH 8.3, 0.075M NaCl (BBS) was added to each well of a microtiter plate (Dynatech Immulon 2 Removawell Strips). The plate was incubated at 4° C. overnight in a humid chamber, after which, the antigen solution was removed and the wells washed 3 times with BBS containing 0.02% TRITON X-100 surfactant (BBST). To prevent nonspecific binding, the wells were coated with bovine serum albumin (BSA) by addition of 100 microliters of a 5 mg/ml solution of BSA in BBS followed by incubation at room temperature for 1 hour; after this incubation the BSA solution was removed. The antigens in the coated wells were reacted with serum by adding 100 microliters of serum samples diluted 1:100 in 0.01M Na phosphate buffer, pH 7.2, 0.15M NaCl (PBS) containing 10 mg/ml BSA, and incubating the serum containing wells for 1 hr at 37° C. After incubation, the serum samples were removed by aspiration, and the wells were washed 5 times with BBST. Antibody bound to the antigen was determined by the binding of $^{125}$I-labeled F (ab)$_2$ sheep anti-human IgG to the coated wells. Aliquots of 100 microliters of the labeled probe (specific activity 5–20 microcuries/microgram) were added to each well, and the plates were incubated at 37° C. for 1 hour, followed by removal of excess probe by aspiration, and 5 washes with BBST. The amount of radioactivity bound in each well was determined by counting in a counter which detects gamma radiation.

Table 1 below presents the results of the tests on the serum from individuals diagnosed as having HCV. The NS5 antigen used in the immunoassays referred to in Table 1 is the antigen spanning amino acids 2054–2464 of FIG. 1 described in Example 5, above.

TABLE 1

| INDIVIDUAL | ANTIGEN | | | | |
|---|---|---|---|---|---|
| | S2 | C22 | C100 | C33c | NS5 |
| CVH IVDA | P | P | P(+++) | P | P |
| CVH IVDA | P | P | P(+) | P | P |
| CVH IVDA | P | P | P(+) | P | P |
| CVH NOS | P | P | P | P | P |
| AVH NOS HS | N | N | N | N | N |
| AVH NOS HS | P | N | N | N | N |
| AVH NOS HS | P | N | N | N | N |
| AVH NOS HS | P/N | N | N | N | N |
| AVH PTVH | N | N | N | P/N | N |
| AVH NOS HS | N | N | N | N | N |
| AVH NOS | N | N | N | N | P |
| AVH PTVH | N | N | N | N | N |
| AVH IVDA | N | P | N | P | P |
| AVH PTVH | P | P/N | N | N | P |
| AVH NOS | N | P | N | N | N |
| AVH IVDA | N | P | N | P | P |
| AVH NOS HS | P/N | N | N | N | N |
| AVH PTVH | N | N | N | N | N |
| CVH IVDA | P | P | P | P | P |
| CVH IVDA | P | P | P | P | P |
| AVH NOS HS | N | N | N | N | N |
| CVH PTVH | P | P | N | N | N |
| AVH PTVH | P | N | P(+) | P(+++) | N |
| CVH PTVH | N | P | P | P | P |
| CVH NOS HS | P | P | P | P | N |
| CVH NOS | N | P | P/N | P | P |
| CVH IVDA | N | N | N | P | P |
| AVH IVDA | P | P | P | P | P |
| AVH IVDA | P | P | P | P | P |
| CVH IVDA | P | P | P | P | P |
| AVH IVDA | P/N | P | N | P | P |
| AVH IVDA | N | P | P | P | N |
| CVH PTVH | P | P/N | N | N | N |
| CVH NOS | N | N | N | N | N |
| CVH NOS | N | N | N | N | N |
| CVH IVDA | P | P | P | P | P |
| AVH IVDA | P | P | P | P | P |
| CVH PTVH | P | P | P | P | P |
| AVH PTVH? | N | P | P | P | P |
| AVH IVDA | N | P | N | P | N |
| AVH NOS | N | N | N | N | N |
| AVH NOS | N | N | N | N | N |
| CVH NOS | N | P | N | N | P |
| CVH NOS | P | P | N | N | N |
| CVH NOS HS | P | P | P | P | P |
| CVH PTVH | P | P | N | P | N |
| AVH nurse | P | P | N | N | N |
| AVH IVDA | P | P | P | P | N |
| AVH IVDA | N | P | P(+) | P(+++) | N |
| AVH nurse | P/N | P | N | N | N |
| AVH PTVH | P/N | P | P | N | P |

TABLE 1-continued

| INDIVIDUAL | ANTIGEN | | | | |
|---|---|---|---|---|---|
| | S2 | C22 | C100 | C33c | NS5 |
| AVH NOS | N | P/N | N | N | P |
| AVH NOS | N | P | N | P | N |
| AVH PTVH | P | P/N | N | N | N |
| AVH PTVH | N | P | N | P | P |
| AVH PTVH | P | P | P | P | P |
| AVH PTVH | N | P | N | N | P |
| CVH PTVH | P/N | P | P(+) | P(+++) | N |
| AVH PTVH | N | P/N | P(+) | P(+++) | P |
| AVH PTVH | P | (?) | P | N | P |
| CVH PTVH | N | P | N | P | P |
| CVH PTVH | N | P | P | P | P |
| CVH PTVH | N | N | N | N | N |
| AVH NOS | N | N | N | N | N |
| AVH nurse | P | P | N | N | N |
| CVH PTVH | N | P | N | N | P |
| AVH IVDA | N | P | N | P/N | N |
| CVH PTVH | P | P | P(+) | P(+++) | P |
| AVH NOS | P | P | N | N | N |
| AVH NOS | P/N | P | N | N | P |
| AVH PTVH | P/N | P | P | P | P |
| AVH NOS | N | P | P | P | P/N |
| AVH IVDA | N | P | N | N | P |
| AVH NOS | N | P/N | N | N | N |
| AVH NOS | P | P | N | N | P |
| AVH PTVH | N | P | P | P | P |
| crypto | P | P | P | P | P |
| CVH NOS | N | P | P | P | P |
| CVH NOS | N | N | N | N | N |
| AVH PTVH | N | P | P(+) | P(++) | N |
| AVH PTVH | N | P/N | P(+) | P(++) | P |
| AVH PTVH | N | P/N | P(+) | P(++) | P |
| CVH IVDA | P | P | P | P | P |
| CVH IVDA | P | P | P | P | P |
| CVH IVDA | P | P | P | P | P |
| CVH IVDA | P | P | P | P | P |
| AVH NOS | N | P | N | N | N |
| CVH IVDA | P | P | P | P | P/N |
| AVH IVDA | P | P | P | P | N |
| AVH NOS | P | P | N | N | N |
| AVH NOS | P | P | N | N | N |
| CVH PTVH | P | P | N | N | P/N |
| AVH PTVH | N | P | N | P | P |
| AVH NOS | N | N | N | N | N |
| AVH NOS | N | P | N | N | N |
| AVH NOS | P | N | N | N | N |
| CVH NOS | N | N | N | N | N |
| AVH NOS | N | P/N | N | N | N |
| AVH IVDA | N | P | P | P | P |
| crypto | N | P | N | N | P/N |
| crypto | P | P | P/N | P | P |
| AVH IVDA | N | N | P | P | N |
| AVH IVDA | N | P | P | P | N |
| AVH NOS | N | N | N | N | N |
| AVH NOS | N | N | N | N | N |
| CVH IVDA | P | P | P | P | P |
| CVH PTVH | N | N | N | N | N |
| CVH PTVH | P | P | P(+) | P(+++) | P |
| CVH PTVH | P | P | P(+) | P(+++) | P |
| CVH NOS | P/N | N | N | N | N |
| CVH NOS | N | N | N | N | N |
| CVH PTVH | P | P | P | P | P |
| CVH PTVH | P | P | P | P | P |
| CVH PTVH | P | P | P | P | P |
| AVH IVDA | N | P | P | P | P |
| CVH NOS | N | N | N | N | N |
| CVH NOS | N | N | N | N | N |
| CVH PTVH | P | P | P | P | P |
| AVH NOS | P | P | N | N | P/N |
| AVH NOS | N | P/N | N | N | N |
| CVH PTVH | N | P | N | N | P |
| CVH NOS | N | P/N | N | N | N |
| AVH NOS | N | P | N | N | N |
| AVH NOS | N | P | N | N | N |
| CVH PTVH | P | P | N | N | N |
| AVH IVDA | N | P | N | P | P |

TABLE 1-continued

| INDIVIDUAL | S2 | C22 | C100 | C33c | NS5 |
|---|---|---|---|---|---|
| AVH NOS | P | N | N | N | N |
| CVH NOS | N | N | N | N | N |
| CVH NOS | N | N | N | N | N |
| CVH IVDA | P | P | P | P | P |
| CVH IVDA | P/N | P | P | P | P |
| CVH IVDA | P | P | P | P | P |
| CVH IVDA | N | P | P | P | P |
| AVH NOS | N | P | N | N | N |
| CVH IVDA | N | P | N | N | P |
| CVH IVDA | N | P | N | N | P |
| AVH PTVH | P | P | N | P | P |
| AVH PTVH | P | P | N | P | P |
| CVH NOS | N | P/N | N | N | P/N |
| CVH NOS | N | P | N | N | N |
| CVH NOS | N | N | N | N | N |
| CVH PTVH | P | P | P | P | P |
| CVH PTVH | P | P | P | P | P |
| CVH PTVH | P | P | P | P | P |
| AVH IVDA | N | P | N | N | P |
| AVH IVDA | N | P | P(++) | P(+) | P |
| CVH PTVH | P | P | P | P | P |
| AVH PTVH | N | P | P | P | P |
| CVH PTVH? | N | P | P | P | P |
| CVH PTVH? | P/N | P | P | P | P |
| CVH NOS HS | P | P | N | N | N |
| CVH IVDA | P | P | P | P | N |
| CVH PTVH | N | P | P | P | P |
| CVH PTVH | P | P | P | P | P/N |
| CVH NOS | P | P | P | P | P |
| CVH IVDA | P | P | P | P | P |
| CVH PTVH | P | P | P | P | N |
| CVH PTVH | P | P | P | P | P |
| CVH NOS | N | N | N | N | P/N |
| CVH NOS | N | P/N | N | N | P/N |
| CVH PTVH | P | P | P | P | P |
| CVH NOS | N | P | N | N | N |
| CVH NOS | N | N | N | N | N |
| CVH NOS | P | P | N | N | P/N |
| CVH NOS | N | N | N | N | N |
| CVH NOS HS | P | P | P | P | P |
| CVH NOS HS | P | P | P | P | P |
| CVH PTVH | N | N | N | N | N |
| AVH PTVH | N | P | P | P | P |
| AVH NOS | — | — | | | |
| CVH PTVH | N | P | P/N | P(+++) | N |
| crypto | P | P | P | P | P |
| crypto | P | P | P | P | P |
| crypto | N | P | N | N | N |
| crypto | N | P | P | P | P |
| CVH PTVH | P | P | P | P | P |
| crypto | N | N | N | N | N |
| crypto | N | P | N | N | P/N |
| crypto | N | P | N | N | P |
| crypto | P | P | P | P | P |
| crypto | N | P | N | P | N |
| crypto | | — | | — | |
| crypto | | — | | — | |
| CVH NOS | | — | | — | |
| AVH-IVDA | N | P | N | P(+) | P |
| AVH-IVDA | N | P/N | N | P(++) | N |

AVH = acute viral hepatitis
CVH = chronic viral hepatitis
PTVH = post-transfusion viral hepatitis
IVDA = intravenous drug abuser
crypto = cryptogenic hepatitis
NOS = non-obvious source
P = positive
N = negative Per these results, no single antigen reacted with all sera. C22 and C33c were the most reactive and S2 reacted with some sera from some putative acute HCV cases with which no other antigen reacted. Based on these results, the combination of two antigens that would provide the greatest range of detection is C22 and C33c. If one wished to detect a maximum of acute infections, S2 would be included in the combination.

Table 2 below presents the results of the testing on the paid blood donors.

TABLE 2

| Donor | Antigens | | | | |
|---|---|---|---|---|---|
| | C100 | C33c | C22 | S2 | NS5 |
| 1 | N | N | N | N | N |
| 2 | N | N | N | N | N |
| 3 | P | P | P | P | P |
| 4 | N | N | N | N | N |
| 5 | N | N | N | N | N |
| 6 | N | N | N | N | N |
| 7 | N | N | N | N | N |
| 8 | N | N | N | N | N |
| 9 | N | N | N | N | N |
| 10 | N | N | N | N | N |
| 11 | N | N | N | N | N |
| 12 | N | N | N | N | N |
| 13 | N | N | N | N | N |
| 14 | N | N | N | N | N |
| 15 | N | N | N | N | N |
| 16 | N | N | N | N | N |
| 17 | N | N | N | N | N |
| 18 | P | P | P | P | P |
| 19 | P | P | N | P | P |
| 20 | P | P | N | P | P |
| 21 | N | N | N | N | N |
| 22 | N | P | P | N | P |
| 23 | P | P | P | P | P |
| 24 | N | N | N | N | N |
| 25 | N | N | N | N | N |
| 26 | N | N | N | N | N |
| 27 | N | N | N | N | N |
| 28 | N | N | N | N | N |
| 29 | N | N | N | N | N |
| 30 | N | N | N | N | N |
| 31 | P | P | P | N | P |
| 32 | N | N | N | N | N |
| 33 | N | N | N | N | N |
| 34 | N | N | N | N | P |
| 35 | N | N | P | N | P |
| 36 | N | N | N | N | N |
| 37 | N | N | N | N | N |
| 38 | N | N | N | N | N |
| 39 | N | N | N | N | N |
| 40 | N | N | N | N | N |
| 41 | N | N | N | N | P |
| 42 | N | N | N | N | N |
| 43 | N | N | N | N | N |
| 44 | N | N | N | N | N |
| 45 | N | N | N | N | N |
| 46 | N | N | N | N | N |
| 47 | P | P | N | N | P |
| 48 | N | N | N | N | N |
| 49 | N | N | N | N | N |
| 50 | N | N | N | N | N |
| 51 | N | P | P | N | P |
| 52 | N | N | N | N | N |
| 53 | N | P | P | N | P |
| 54 | P | P | P | P | N |
| 55 | N | N | N | N | N |
| 56 | N | N | N | N | N |
| 57 | N | N | N | N | N |
| 58 | N | N | N | N | N |
| 59 | N | N | N | N | N |
| 60 | N | N | N | N | N |
| 61 | N | N | N | N | N |
| 62 | N | N | N | N | N |
| 63 | N | N | N | N | N |
| 64 | N | N | N | N | N |
| 65 | N | N | N | N | N |
| 66 | N | N | N | N | N |
| 67 | N | N | N | N | N |
| 68 | N | N | N | N | N |

TABLE 2-continued

| Donor | C100 | C33c | C22 | S2 | NS5 |
|---|---|---|---|---|---|
| 69 | N | N | N | N | N |
| 70 | P | P | P | P | P |
| 71 | N | N | N | N | N |
| 72 | N | N | N | N | N |
| 73 | P | P | P | P | N |
| 74 | N | N | N | N | N |
| 75 | N | N | N | N | N |
| 76 | N | N | N | N | P |
| 77 | N | N | N | N | N |
| 78 | N | N | N | N | N |
| 79 | N | N | N | N | N |
| 80 | N | N | N | N | N |
| 81 | N | N | N | N | N |
| 82 | N | N | N | N | N |
| 83 | P | P | N | N | N |
| 84 | N | N | P | N | N |
| 85 | N | N | N | N | N |
| 86 | P | P | P | P | N |
| 87 | N | N | N | N | N |
| 88 | N | N | N | N | N |
| 89 | P | P | P | P | P |
| 90 | P | P | P | P | N |
| 91 | N | N | N | N | P |
| 92 | P | P | P | N | N |
| 93 | N | N | N | N | N |
| 94 | N | N | N | N | N |
| 95 | N | N | N | N | N |
| 96 | N | N | N | N | N |
| 97 | N | N | N | N | N |
| 98 | N | P | P | P | P |
| 99 | P | P | P | P | P |
| 100 | N | N | N | N | N |
| 101 | P | P | P | P | P |
| 102 | N | N | N | N | N |
| 103 | N | N | N | N | N |
| 104 |   | N | N | N | N |
| 105 | P | P | P | P | N |
| 106 | N | N | N | N | N |
| 107 | N | N | N | N | N |
| 108 | N | N | N | N | N |
| 109 | P | P | P | P | P |
| 110 | P | P | P | N | P |
| 111 | P | P | P | N | P |
| 112 | N | N | N | N | N |
| 113 | P | P | P | P | P |
| 114 | N | N | N | N | N |
| 115 | N | N | N | N | N |
| 116 | P | P | P | P | P |
| 117 | N | N | N | N | N |
| 118 | N | N | N | N | N |
| 119 | N | N | N | N | N |
| 120 | P | P | P | P | P |
| 121 | N | N | N | N | N |
| 122 | N | P | P | N | P |
| 123 | N | N | N | N | N |
| 124 | N | N | N | N | N |
| 125 | N | N | N | N | N |
| 126 | P | N | N | N | N |
| 127 | N | N | N | N | N |
| 128 | N | N | N | N | N |
| 129 | N | N | N | N | N |
| 130 | P | P | P | P | N |
| 131 | N | N | N | N | P |
| 132 | N | N | N | N | N |
| 133 | N | N | N | N | N |
| 134 | N | N | N | N | N |
| 135 | N | N | N | N | N |
| 136 | N | N | N | N | N |
| 137 | N | N | N | N | N |
| 138 | N | N | N | N | N |
| 139 | N | N | N | N | N |
| 140 | P | N | N | N | N |
| 141 | P | N | P | P | P |
| 142 | N | N | N | N | N |
| 143 | N | N | N | N | N |
| 144 | N | N | N | N | N |
| 145 | N | N | N | N | N |
| 146 | N | N | N | N | N |
| 147 | N | N | N | N | N |
| 148 | N | N | N | N | N |
| 149 | N | N | N | N | N |
| 150 | N | N | N | N | N |
| 151 | N | N | N | N | N |
| 152 | N | N | N | N | N |
| 153 | N | N | N | N | N |
| 154 | P | P | P | P | P |
| 155 | N | N | N | N | N |
| 156 | N | N | N | N | N |
| 157 | N | N | N | N | N |
| 158 | N | N | N | N | N |
| 159 | N | N | N | N | N |
| 160 | N | N | N | N | N |
| 161 | P | P | P | P | P |
| 162 | N | N | N | N | N |
| 163 | N | N | N | N | N |
| 164 | P | P | P | N | P |
| 165 | N | N | N | N | N |
| 166 | P | P | P | N | P |
| 167 | N | N | N | N | N |
| 168 | N | N | N | N | N |
| 169 | N | N | N | N | N |
| 170 | N | N | N | N | N |
| 171 | N | N | N | N | N |
| 172 | N | N | N | N | N |
| 173 | N | N | N | N | N |
| 174 | N | N | N | N | N |
| 175 | N | N | N | N | N |
| 176 | N | N | N | N | N |
| 177 | N | N | N | N | P |
| 178 | N | N | N | N | N |
| 179 | N | N | N | N | N |
| 180 | N | N | N | N | N |
| 181 | N | N | N | N | N |
| 182 | N | N | N | N | N |
| 183 | P | P | P | P | P |
| 184 | N | N | N | N | N |
| 185 | N | N | N | N | N |
| 186 | N | N | N | N | N |
| 187 | N | N | N | N | N |
| 188 | N | P | P | N | N |
| 189 | N | N | N | N | N |
| 190 | N | N | N | N | N |
| 191 | N | N | N | N | N |
| 192 | N | N | N | N | N |
| 193 | N | N | N | N | N |
| 194 | N | N | N | N | N |
| 195 | N | N | N | N | N |
| 196 | N | N | N | N | N |
| 197 | N | N | N | N | P |
| 198 | P | P | P | N | N |
| 199 | N | N | N | N | P |
| 200 | P | P | P | P | N |

The results on the paid donors generally confirms the results from the sera of infected individuals.

Example 7: ELISA Determinations of HCV Antibodies Using Combination of HCV Antigens Plates coated with a combination of C22 and C33c antigens are prepared as follows. A solution containing coating buffer (50mM Na Borate, pH 9.0), 21 ml/plate, BSA (25 micrograms/ml), C22 and C33c (2.50 micrograms/ml each) is prepared just prior to addition to the Removeawell Immulon I plates (Dynatech Corp.). After mixing for 5 minutes, 0.2ml/well of the solution is added to the plates, they are covered and incubated for 2 hours at 37° C., after which the solution is removed by aspiration. The wells are washed once with 400 microliters wash buffer (100 mM sodium phosphate, pH 7.4, 140 mM sodium chloride, 0.1% (W/V) casein, 1% (W/V) TRITON x-100 surfactant 0.01% (W/V) Thimerosal). After removal of the wash solution, 200 microliters/well of Postcoat solution (10 mM sodium phosphate, pH 7.2, 150 mM sodium chloride, 0.1% (w/v) casein, 3% sucrose and 2 mM phenylmethylsulfonylfluoride (PMSF)) is added, the plates are loosely covered to prevent evaporation, and are allowed to stand at room temperature for 30 minutes. The wells are then aspirated to remove the solution, and lyophilized dry overnight, without shelf heating. The prepared plates may be stored at 2–8° C. in sealed aluminum pouches with dessicant (3 g Sorb-it™ packs).

In order to perform the ELISA determination, 20 microliters of serum sample or control sample is added to a well containing 200 microliters of sample diluent (100 mM sodium phosphate, pH 7.4, 500 mM sodium chloride, 1 mM EDTA, 0.1% (W/V) Casein, 0.01% (W/V) Thimerosal, 1% (W/V) TRITON X-100 surfactant, 100 micrograms/ml yeast extract). The plates are sealed, and are incubated at 37° C. for two hours, after which the solution is removed by aspiration, and the wells are washed three times with 400 microliters of wash buffer (phosphate buffered saline (PBS) containing 0.05% TWEEN 20 surfactant). The washed wells are treated with 200 microliters of mouse anti-human IgG-horse radish peroxidase (HRP) conjugate contained in a solution of Ortho conjugate diluent (10 mM sodium phosphate, pH 7.2, 150 mM sodium chloride, 50% (V/V) fetal bovine serum, 1% (V/V) heat treated horse serum, 1 mM $K_3Fe(CN)_6$, 0.05% (W/V) TWEEN 20 surfactant, 0.02% (W/V) Thimerosal). Treatment is for 1 hour at 37° C., the solution is removed by aspiration, and the wells are washed three times with 400 ml wash buffer, which is also removed by aspiration. To determine the amount of bound enzyme conjugate, 200 microliters of substrate solution (10 mg O-phenylenediamine dihydrochloride per 5 ml of Developer solution) is added. Developer solution contains 50 mM sodium citrate adjusted to pH 5.1 with phosphoric acid, and 0.6 microliters/ml of 30% $H_2O_2$. The plates containing the substrate solution are incubated in the dark for 30 minutes at room temperature, the reactions are stopped by the addition of 50 microliters/ml 4N sulfuric acid, and the ODs determined.

In a similar manner, ELISAs using fusion proteins of C22 and C33c, and C22, C33c, and S2 and combinations of C22 and C100, C22 and S2, C22 and an NS5 antigen, C22, C33c, and S2, and C22, C100, and S2 may be carried out.

Modifications of the above-described modes for carrying out the invention that are obvious to those of skill in the fields of molecular biology, immunology, and related fields are intended to be within the scope of the following claims.

---

We claim:

1. A combination of hepatitis C viral (HCV) antigens comprising:
   (a) a first HCV antigen comprising the C domain or an immunologically reactive fragment thereof containing at least 8 amino acids, said C domain consisting of amino acids 1 to 120 of the HCV polyprotein; and
   (b) two additional HCV antigens from two different HCV polyprotein domains each independently selected from the group consisting of
      (i) an HCV antigen comprising the NS3 domain or an immunologically reactive fragment thereof containing at least 8 amino acids, said NS3 domain consisting of amino acids 1050 to 1640 of the HCV polyprotein;
      (ii) an HCV antigen comprising the NS4 domain or an immunologically reactive fragment thereof containing at least 8 amino acids, said NS4 domain consisting of amino acids 1640 to 2000 of the HCV polyprotein;
      (iii) an HCV antigen comprising the S domain or an immunologically reactive fragment thereof containing at least 8 amino acids, said S domain consisting of amino acids 120 to 400 of the HCV polyprotein; and
      (iv) an HCV antigen comprising the NS5 domain or an immunologically reactive fragment thereof containing at least 8 amino acids, said NS5 domain consisting of amino acids 2000 to 3011 of the HCV polyprotein.

2. A combination of hepatitis C viral (HCV) antigens according to claim 1, wherein at least one of said additional antigens comprises the NS3 domain or an immunologically reactive fragment thereof containing at least 8 amino acids, said NS3 domain consisting of amino acids 1050 to 1640 of the HCV polyprotein.

3. A combination of hepatitis C viral (HCV) antigens according to claim 1, wherein at least one of said additional antigens comprises the NS4 domain or an immunologically reactive fragment thereof containing at least 8 amino acids, said NS4 domain consisting of amino acids 1640–2000 of the HCV polyprotein.

4. A combination of hepatitis C viral (HCV) antigens according to claim 1, wherein at least one of said additional antigens comprises the S domain or an immunologically reactive fragment thereof containing at least 8 amino acids, said S domain consisting of amino acids 120–400 of the HCV polyprotein.

5. A combination of hepatitis C viral (HCV) antigens according to claim 1, wherein at least one of said additional antigens comprises the NS5 domain or an immunologically reactive fragment thereof containing at least 8 amino acids, said NS5 domain consisting of amino acids 2000–3011 of the HCV polyprotein.

6. A combination of hepatitis C viral (HCV) antigens according to claim 1, wherein at least one of said additional antigens is amino acids 1192–1457 of the HCV polyprotein or an immunologically reactive fragment thereof containing at least 8 amino acids.

7. A combination of hepatitis C viral (HCV) antigens according to claim 1, wherein at least one of said additional antigens is amino acids 1569–1931 of the HCV polyprotein or an immunologically reactive fragment thereof containing at least 8 amino acids.

8. A combination of hepatitis C viral (HCV) antigens according to claim 1, wherein at least one of said additional antigens is amino acids 199–328 of the HCV polyprotein or an immunologically reactive fragment thereof containing at least 8 amino acids.

9. A combination of hepatitis C viral (HCV) antigens according to claim 1, wherein at least one of said additional antigens is amino acids 2054–2464 of the HCV polyprotein or an immunologically reactive fragment thereof containing at least 8 amino acids.

10. A combination of hepatitis C viral (HCV) antigens according to claim 2, wherein at least one of said additional antigens comprises the NS4 domain or an immunologically reactive fragment thereof containing at least 8 amino acids, said NS4 domain consisting of amino acids 1640–2000 of the HCV polyprotein.

11. A combination of hepatitis C viral (HCV) antigens according to claim 2, wherein at least one of said additional antigens comprises the S domain or an immunologically reactive fragment thereof containing at least 8 amino acids, said S domain consisting of amino acids 120–400 of the HCV polyprotein.

12. A combination of hepatitis C vital (HCV) antigens according to claim 2, wherein at least one of said additional antigens comprises the NS5 domain or an immunologically reactive fragment thereof containing at least 8 amino acids, said NS5 domain consisting of amino acids 2000–3011 of the HCV polyprotein.

13. A combination of hepatitis C vital (HCV) antigens comprising:

(a) a first HCV antigen which is amino acids 1–122 of the HCV polyprotein or an immunologically reactive fragment thereof containing at least 8 amino acids; and (b) two additional HCV antigens from two different HCV polyprotein domains each independently selected from the group consisting of (i) an HCV antigen comprising the NS3 domain or an immunologically reactive fragment thereof containing at least 8 amino acids, said NS3 domain consisting of amino acids 1050 to 1640 of the HCV polyprotein;

(ii) an HCV antigen comprising the NS4 domain or an immunologically reactive fragment thereof containing at least 8 amino acids, said NS4 domain consisting of amino acids 1640 to 2000 of the HCV polyprotein:

(iii) an HCV antigen comprising the S domain or an immunologically reactive fragment thereof containing at least 8 amino acids, said S domain consisting of amino acids 120 to 400 of the HCV polyprotein; and (iv) an HCV antigen comprising the NS5 domain or an immunologically reactive fragment thereof containing at least 8 amino acids, said NS5 domain consisting of amino acids 2000 to 3011 of the HCV polyprotein.

14. A combination of hepatitis C viral (HCV) antigens comprising:

(a) a first HCV antigen which is amino acids 9–177 of the HCV polyprotein or an immunologically reactive fragment thereof containing at least 8 amino acids; and (b) two additional HCV antigens from two different HCV polyprotein domains each independently selected from the group consisting of (i) an HCV antigen comprising the NS3 domain or an immunologically reactive fragment thereof containing at least 8 amino acids, said NS3 domain consisting of amino acids 1050 to 1640 of the HCV polyprotein;

(ii) an HCV antigen comprising the NS4 domain or an immunologically reactive fragment thereof containing at least 8 amino acids, said NS4 domain consisting of amino acids 1640 to 2000 of the HCV polyprotein;

(iii) an HCV antigen comprising the S domain or an immunologically reactive fragment thereof containing at least 8 amino acids, said S domain consisting of amino acids 120 to 400 of the HCV polyprotein; and (iv) an HCV antigen comprising the NS5 domain or an immunologically reactive fragment thereof containing at least 8 amino acids, said NS5 domain consisting of amino acids 2000 to 3011 of the HCV polyprotein.

15. A combination according to claim 1, 2, 3, 4, 5, 6, 7, 8, 9, 10, 11, 12, 13, or 14, wherein said HCV antigens are produced by recombinant expression or chemical synthesis.

16. A combination according to claim 1, 2, 3, 4, 5, 6, 7, 8, 9, 10, 11, 12, 13, or 14, wherein the combination is in the form of a fusion polypeptide.

17. A combination according to claim 16, wherein said HCV antigens are produced by recombinant expression or chemical synthesis.

18. A combination according to claim 1, 2, 3, 4, 5, 6, 7, 8, 9, 10, 11, 12, 13, or 14, wherein the combination is in the form of said first HCV antigen and said additional antigen(s) individually bound to a common solid matrix.

19. A combination according to claim 18, wherein said HCV antigens are produced by recombinant expression or chemical synthesis.

20. A combination according to claim 19, wherein the solid matrix is selected from the group consisting of the surface of a microtiter plate well, a head or a dipstick.

21. A combination according to claim 1, 2, 3, 4, 5, 6, 7, 8, 9, 10, 11, 12, 13, or 14, wherein the combination is in the form of a mixture of said first HCV antigen and said additional antigen(s).

22. A combination according to claim 21, wherein said HCV antigens are produced by recombinant expression or chemical synthesis.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GATCCTGGAA TTCTGATAA        19

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AATTTTATCA GAATTCCAG        19

( 2 ) INFORMATION FOR SEQ ID NO:3:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAGTGCTCAA GCTTCAAAAC AAAATGGCTC ACTTTCTATC CCAGACAAAG CAGAGT        56

( 2 ) INFORMATION FOR SEQ ID NO:4:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GAGTGCTCGT CGACTCATTA GGGGGAAACA TGGTTCCCCC GGGAGGCGAA              50

( 2 ) INFORMATION FOR SEQ ID NO:5:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GAGTGCTCAA GCTTCAAAAC AAAATGGGGC TCTACCACGT CACCAATGAT TGCCCTAAC    59

( 2 ) INFORMATION FOR SEQ ID NO:6:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GAGTGCTCGT CGACTCATTA AGGGGACCAG TTCATCATCA TATCCCATGC CAT          53

( 2 ) INFORMATION FOR SEQ ID NO:7:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GAGTGCAGCC TTCAAAACAA AATGAGCACG AATCCTAAAC CTCAAAAAAA AAAC         54

( 2 ) INFORMATION FOR SEQ ID NO:8:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GAGTGCTCGT CGACTCATTA ACCCAAATTG CGCGACCTAC GCCGGGGTC TGT           53

( 2 ) INFORMATION FOR SEQ ID NO:9:

( i ) SEQUENCE CHARACTERISTICS:
        ( A ) LENGTH: 9401 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 342..9374

( i x ) FEATURE:
        ( A ) NAME/KEY: misc_feature
        ( B ) LOCATION: 366
        ( D ) OTHER INFORMATION: /note="This amino acid position can also be Arg."

( i x ) FEATURE:
        ( A ) NAME/KEY: misc_feature
        ( B ) LOCATION: 372
        ( D ) OTHER INFORMATION: /note="This amino acid position can also be Thr."

( i x ) FEATURE:
        ( A ) NAME/KEY: misc_feature
        ( B ) LOCATION: 867
        ( D ) OTHER INFORMATION: /note="This amino acid position can also be Thr."

( i x ) FEATURE:
        ( A ) NAME/KEY: misc_feature
        ( B ) LOCATION: 1341
        ( D ) OTHER INFORMATION: /note="This amino acid position can also be Val."

( i x ) FEATURE:
        ( A ) NAME/KEY: misc_feature
        ( B ) LOCATION: 2148
        ( D ) OTHER INFORMATION: /note="This amino acid position can also be Ile."

( i x ) FEATURE:
        ( A ) NAME/KEY: misc_feature
        ( B ) LOCATION: 2883
        ( D ) OTHER INFORMATION: /note="This amino acid position can also be Asn."

( i x ) FEATURE:
        ( A ) NAME/KEY: misc_feature
        ( B ) LOCATION: 3681
        ( D ) OTHER INFORMATION: /note="This amino acid position can also be Ser."

( i x ) FEATURE:
        ( A ) NAME/KEY: misc_feature
        ( B ) LOCATION: 3690
        ( D ) OTHER INFORMATION: /note="This amino acid position can also be Thr."

( i x ) FEATURE:
        ( A ) NAME/KEY: misc_feature
        ( B ) LOCATION: 4167
        ( D ) OTHER INFORMATION: /note="This amino acid position can also be Leu."

( i x ) FEATURE:
        ( A ) NAME/KEY: misc_feature
        ( B ) LOCATION: 4323
        ( D ) OTHER INFORMATION: /note="This amino acid position can also be Val."

( i x ) FEATURE:
        ( A ) NAME/KEY: misc_feature
        ( B ) LOCATION: 4701
        ( D ) OTHER INFORMATION: /note="This amino acid position can also be Tyr."

( i x ) FEATURE:
    ( A ) NAME/KEY: misc_feature
    ( B ) LOCATION: 4752
    ( D ) OTHER INFORMATION: /note="This amino acid position can also be Ser."

( i x ) FEATURE:
    ( A ) NAME/KEY: misc_feature
    ( B ) LOCATION: 5970
    ( D ) OTHER INFORMATION: /note="This amino acid position can also be Gly."

( i x ) FEATURE:
    ( A ) NAME/KEY: misc_feature
    ( B ) LOCATION: 6183
    ( D ) OTHER INFORMATION: /note="This amino acid position can also be His."

( i x ) FEATURE:
    ( A ) NAME/KEY: misc_feature
    ( B ) LOCATION: 6186
    ( D ) OTHER INFORMATION: /note="This amino acid position can also be Cys."

( i x ) FEATURE:
    ( A ) NAME/KEY: misc_feature
    ( B ) LOCATION: 6402
    ( D ) OTHER INFORMATION: /note="This amino acid position can also be Val."

( i x ) FEATURE:
    ( A ) NAME/KEY: misc_feature
    ( B ) LOCATION: 7386
    ( D ) OTHER INFORMATION: /note="This amino acid position can also be Ser."

( i x ) FEATURE:
    ( A ) NAME/KEY: misc_feature
    ( B ) LOCATION: 7494
    ( D ) OTHER INFORMATION: /note="This amino acid position can also be Phe."

( i x ) FEATURE:
    ( A ) NAME/KEY: misc_feature
    ( B ) LOCATION: 7497
    ( D ) OTHER INFORMATION: /note="This amino acid position can also be Ala."

( i x ) FEATURE:
    ( A ) NAME/KEY: misc_feature
    ( B ) LOCATION: 7845
    ( D ) OTHER INFORMATION: /note="This amino acid position can also be Phe."

( i x ) FEATURE:
    ( A ) NAME/KEY: misc_feature
    ( B ) LOCATION: 8409
    ( D ) OTHER INFORMATION: /note="This amino acid position can also be Gly."

( i x ) FEATURE:
    ( A ) NAME/KEY: misc_feature
    ( B ) LOCATION: 9102
    ( D ) OTHER INFORMATION: /note="This amino acid position can also by Gly."

( i x ) FEATURE:
    ( A ) NAME/KEY: misc_feature
    ( B ) LOCATION: 9327
    ( D ) OTHER INFORMATION: /note="This amino acid position can also be Pro."

( x i ) SEQUENCE DESCRIPTION: SEQ ID NO:9:

```
GCCAGCCCCC TGATGGGGGC GACACTCCAC CATGAATCAC TCCCCTGTGA GGAACTACTG      60
TCTTCACGCA GAAAGCGTCT AGCCATGGCG TTAGTATGAG TGTCGTGCAG CCTCCAGGAC     120
CCCCCCTCCC GGGAGAGCCA TAGTGGTCTG CGGAACCGGT GAGTACACCG GAATTGCCAG     180
```

-continued

```
GACGACCGGG TCCTTTCTTG GATCAACCCG CTCAATGCCT GGAGATTTGG GCGTGCCCCC              240

GCAAGACTGC TAGCCGAGTA GTGTTGGGTC GCGAAAGGCC TTGTGGTACT GCCTGATAGG              300

GTGCTTGCGA GTGCCCCGGG AGGTCTCGTA GACCGTGCAC C ATG AGC ACG AAT                  353
                                               Met Ser Thr Asn
                                                 1
```

| | | | | | | | | | | | | | | | | |
|---|---|---|---|---|---|---|---|---|---|---|---|---|---|---|---|---|
| CCT | AAA | CCT | CAA | AAA | AAA | AAC | AAA | CGT | AAC | ACC | AAC | CGT | CGC | CCA | CAG | 401 |
| Pro | Lys | Pro | Gln | Lys | Lys | Asn | Lys | Arg | Asn | Thr | Asn | Arg | Arg | Pro | Gln | |
| 5 | | | | 10 | | | | | 15 | | | | | | 20 | |
| GAC | GTC | AAG | TTC | CCG | GGT | GGC | GGT | CAG | ATC | GTT | GGT | GGA | GTT | TAC | TTG | 449 |
| Asp | Val | Lys | Phe | Pro | Gly | Gly | Gly | Gln | Ile | Val | Gly | Gly | Val | Tyr | Leu | |
| | | | | 25 | | | | | 30 | | | | | 35 | | |
| TTG | CCG | CGC | AGG | GGC | CCT | AGA | TTG | GGT | GTG | CGC | GCG | ACG | AGA | AAG | ACT | 497 |
| Leu | Pro | Arg | Arg | Gly | Pro | Arg | Leu | Gly | Val | Arg | Ala | Thr | Arg | Lys | Thr | |
| | | | 40 | | | | | 45 | | | | | 50 | | | |
| TCC | GAG | CGG | TCG | CAA | CCT | CGA | GGT | AGA | CGT | CAG | CCT | ATC | CCC | AAG | GCT | 545 |
| Ser | Glu | Arg | Ser | Gln | Pro | Arg | Gly | Arg | Arg | Gln | Pro | Ile | Pro | Lys | Ala | |
| | | 55 | | | | | 60 | | | | | 65 | | | | |
| CGT | CGG | CCC | GAG | GGC | AGG | ACC | TGG | GCT | CAG | CCC | GGG | TAC | CCT | TGG | CCC | 593 |
| Arg | Arg | Pro | Glu | Gly | Arg | Thr | Trp | Ala | Gln | Pro | Gly | Tyr | Pro | Trp | Pro | |
| | 70 | | | | | 75 | | | | | 80 | | | | | |
| CTC | TAT | GGC | AAT | GAG | GGC | TGC | GGG | TGG | GCG | GGA | TGG | CTC | CTG | TCT | CCC | 641 |
| Leu | Tyr | Gly | Asn | Glu | Gly | Cys | Gly | Trp | Ala | Gly | Trp | Leu | Leu | Ser | Pro | |
| 85 | | | | | 90 | | | | | 95 | | | | | 100 | |
| CGT | GGC | TCT | CGG | CCT | AGC | TGG | GGC | CCC | ACA | GAC | CCC | CGG | CGT | AGG | TCG | 689 |
| Arg | Gly | Ser | Arg | Pro | Ser | Trp | Gly | Pro | Thr | Asp | Pro | Arg | Arg | Arg | Ser | |
| | | | | 105 | | | | | 110 | | | | | 115 | | |
| CGC | AAT | TTG | GGT | AAG | GTC | ATC | GAT | ACC | CTT | ACG | TGC | GGC | TTC | GCC | GAC | 737 |
| Arg | Asn | Leu | Gly | Lys | Val | Ile | Asp | Thr | Leu | Thr | Cys | Gly | Phe | Ala | Asp | |
| | | | 120 | | | | | 125 | | | | | 130 | | | |
| CTC | ATG | GGG | TAC | ATA | CCG | CTC | GTC | GGC | GCC | CCT | CTT | GGA | GGC | GCT | GCC | 785 |
| Leu | Met | Gly | Tyr | Ile | Pro | Leu | Val | Gly | Ala | Pro | Leu | Gly | Gly | Ala | Ala | |
| | | 135 | | | | | 140 | | | | | 145 | | | | |
| AGG | GCC | CTG | GCG | CAT | GGC | GTC | CGG | GTT | CTG | GAA | GAC | GGC | GTG | AAC | TAT | 833 |
| Arg | Ala | Leu | Ala | His | Gly | Val | Arg | Val | Leu | Glu | Asp | Gly | Val | Asn | Tyr | |
| | 150 | | | | | 155 | | | | | 160 | | | | | |
| GCA | ACA | GGG | AAC | CTT | CCT | GGT | TGC | TCT | TTC | TCT | ATC | TTC | CTT | CTG | GCC | 881 |
| Ala | Thr | Gly | Asn | Leu | Pro | Gly | Cys | Ser | Phe | Ser | Ile | Phe | Leu | Leu | Ala | |
| 165 | | | | | 170 | | | | | 175 | | | | | 180 | |
| CTG | CTC | TCT | TGC | TTG | ACT | GTG | CCC | GCT | TCG | GCC | TAC | CAA | GTG | CGC | AAC | 929 |
| Leu | Leu | Ser | Cys | Leu | Thr | Val | Pro | Ala | Ser | Ala | Tyr | Gln | Val | Arg | Asn | |
| | | | | 185 | | | | | 190 | | | | | 195 | | |
| TCC | ACG | GGG | CTT | TAC | CAC | GTC | ACC | AAT | GAT | TGC | CCT | AAC | TCG | AGT | ATT | 977 |
| Ser | Thr | Gly | Leu | Tyr | His | Val | Thr | Asn | Asp | Cys | Pro | Asn | Ser | Ser | Ile | |
| | | | 200 | | | | | 205 | | | | | 210 | | | |
| GTG | TAC | GAG | GCG | GCC | GAT | GCC | ATC | CTG | CAC | ACT | CCG | GGG | TGC | GTC | CCT | 1025 |
| Val | Tyr | Glu | Ala | Ala | Asp | Ala | Ile | Leu | His | Thr | Pro | Gly | Cys | Val | Pro | |
| | | 215 | | | | | 220 | | | | | 225 | | | | |
| TGC | GTT | CGT | GAG | GGC | AAC | GCC | TCG | AGG | TGT | TGG | GTG | GCG | ATG | ACC | CCT | 1073 |
| Cys | Val | Arg | Glu | Gly | Asn | Ala | Ser | Arg | Cys | Trp | Val | Ala | Met | Thr | Pro | |
| | 230 | | | | | 235 | | | | | 240 | | | | | |
| ACG | GTG | GCC | ACC | AGG | GAT | GGC | AAA | CTC | CCC | GCG | ACG | CAG | CTT | CGA | CGT | 1121 |
| Thr | Val | Ala | Thr | Arg | Asp | Gly | Lys | Leu | Pro | Ala | Thr | Gln | Leu | Arg | Arg | |
| 245 | | | | | 250 | | | | | 255 | | | | | 260 | |
| CAC | ATC | GAT | CTG | CTT | GTC | GGG | AGC | GCC | ACC | CTC | TGT | TCG | GCC | CTC | TAC | 1169 |
| His | Ile | Asp | Leu | Leu | Val | Gly | Ser | Ala | Thr | Leu | Cys | Ser | Ala | Leu | Tyr | |
| | | | | 265 | | | | | 270 | | | | | 275 | | |
| GTG | GGG | GAC | CTA | TGC | GGG | TCT | GTC | TTT | CTT | GTC | GGC | CAA | CTG | TTC | ACC | 1217 |
| Val | Gly | Asp | Leu | Cys | Gly | Ser | Val | Phe | Leu | Val | Gly | Gln | Leu | Phe | Thr | |
| | | | 280 | | | | | 285 | | | | | 290 | | | |

```
TTC TCT CCC AGG CGC CAC TGG ACG ACG CAA GGT TGC AAT TGC TCT ATC      1265
Phe Ser Pro Arg Arg His Trp Thr Thr Gln Gly Cys Asn Cys Ser Ile
        295                 300                 305

TAT CCC GGC CAT ATA ACG GGT CAC CGC ATG GCA TGG GAT ATG ATG ATG      1313
Tyr Pro Gly His Ile Thr Gly His Arg Met Ala Trp Asp Met Met Met
        310                 315                 320

AAC TGG TCC CCT ACG ACG GCG TTG GTA ATG GCT CAG CTG CTC CGG ATC      1361
Asn Trp Ser Pro Thr Thr Ala Leu Val Met Ala Gln Leu Leu Arg Ile
325                 330                 335                 340

CCA CAA GCC ATC TTG GAC ATG ATC GCT GGT GCT CAC TGG GGA GTC CTG      1409
Pro Gln Ala Ile Leu Asp Met Ile Ala Gly Ala His Trp Gly Val Leu
                    345                 350                 355

GCG GGC ATA GCG TAT TTC TCC ATG GTG GGG AAC TGG GCG AAG GTC CTG      1457
Ala Gly Ile Ala Tyr Phe Ser Met Val Gly Asn Trp Ala Lys Val Leu
                360                 365                 370

GTA GTG CTG CTG CTA TTT GCC GGC GTC GAC GCG GAA ACC CAC GTC ACC      1505
Val Val Leu Leu Leu Phe Ala Gly Val Asp Ala Glu Thr His Val Thr
            375                 380                 385

GGG GGA AGT GCC GGC CAC ACT GTG TCT GGA TTT GTT AGC CTC CTC GCA      1553
Gly Gly Ser Ala Gly His Thr Val Ser Gly Phe Val Ser Leu Leu Ala
        390                 395                 400

CCA GGC GCC AAG CAG AAC GTC CAG CTG ATC AAC ACC AAC GGC AGT TGG      1601
Pro Gly Ala Lys Gln Asn Val Gln Leu Ile Asn Thr Asn Gly Ser Trp
405                 410                 415                 420

CAC CTC AAT AGC ACG GCC CTG AAC TGC AAT GAT AGC CTC AAC ACC GGC      1649
His Leu Asn Ser Thr Ala Leu Asn Cys Asn Asp Ser Leu Asn Thr Gly
                    425                 430                 435

TGG TTG GCA GGG CTT TTC TAT CAC CAC AAG TTC AAC TCT TCA GGC TGT      1697
Trp Leu Ala Gly Leu Phe Tyr His His Lys Phe Asn Ser Ser Gly Cys
                440                 445                 450

CCT GAG AGG CTA GCC AGC TGC CGA CCC CTT ACC GAT TTT GAC CAG GGC      1745
Pro Glu Arg Leu Ala Ser Cys Arg Pro Leu Thr Asp Phe Asp Gln Gly
            455                 460                 465

TGG GGC CCT ATC AGT TAT GCC AAC GGA AGC GGC CCC GAC CAG CGC CCC      1793
Trp Gly Pro Ile Ser Tyr Ala Asn Gly Ser Gly Pro Asp Gln Arg Pro
        470                 475                 480

TAC TGC TGG CAC TAC CCC CCA AAA CCT TGC GGT ATT GTG CCC GCG AAG      1841
Tyr Cys Trp His Tyr Pro Pro Lys Pro Cys Gly Ile Val Pro Ala Lys
485                 490                 495                 500

AGT GTG TGT GGT CCG GTA TAT TGC TTC ACT CCC AGC CCC GTG GTG GTG      1889
Ser Val Cys Gly Pro Val Tyr Cys Phe Thr Pro Ser Pro Val Val Val
                    505                 510                 515

GGA ACG ACC GAC AGG TCG GGC GCG CCC ACC TAC AGC TGG GGT GAA AAT      1937
Gly Thr Thr Asp Arg Ser Gly Ala Pro Thr Tyr Ser Trp Gly Glu Asn
                520                 525                 530

GAT ACG GAC GTC TTC GTC CTT AAC AAT ACC AGG CCA CCG CTG GGC AAT      1985
Asp Thr Asp Val Phe Val Leu Asn Asn Thr Arg Pro Pro Leu Gly Asn
            535                 540                 545

TGG TTC GGT TGT ACC TGG ATG AAC TCA ACT GGA TTC ACC AAA GTG TGC      2033
Trp Phe Gly Cys Thr Trp Met Asn Ser Thr Gly Phe Thr Lys Val Cys
        550                 555                 560

GGA GCG CCT CCT TGT GTC ATC GGA GGG GCG GGC AAC AAC ACC CTG CAC      2081
Gly Ala Pro Pro Cys Val Ile Gly Gly Ala Gly Asn Asn Thr Leu His
565                 570                 575                 580

TGC CCC ACT GAT TGC TTC CGC AAG CAT CCG GAC GCC ACA TAC TCT CGG      2129
Cys Pro Thr Asp Cys Phe Arg Lys His Pro Asp Ala Thr Tyr Ser Arg
                    585                 590                 595

TGC GGC TCC GGT CCC TGG ATC ACA CCC AGG TGC CTG GTC GAC TAC CCG      2177
Cys Gly Ser Gly Pro Trp Ile Thr Pro Arg Cys Leu Val Asp Tyr Pro
                600                 605                 610
```

```
TAT AGG CTT TGG CAT TAT CCT TGT ACC ATC AAC TAC ACC ATA TTT AAA        2225
Tyr Arg Leu Trp His Tyr Pro Cys Thr Ile Asn Tyr Thr Ile Phe Lys
        615             620                 625

ATC AGG ATG TAC GTG GGA GGG GTC GAA CAC AGG CTG GAA GCT GCC TGC        2273
Ile Arg Met Tyr Val Gly Gly Val Glu His Arg Leu Glu Ala Ala Cys
    630             635                 640

AAC TGG ACG CGG GGC GAA CGT TGC GAT CTG GAA GAC AGG GAC AGG TCC        2321
Asn Trp Thr Arg Gly Glu Arg Cys Asp Leu Glu Asp Arg Asp Arg Ser
645             650                 655                 660

GAG CTC AGC CCG TTA CTG CTG ACC ACT ACA CAG TGG CAG GTC CTC CCG        2369
Glu Leu Ser Pro Leu Leu Leu Thr Thr Thr Gln Trp Gln Val Leu Pro
                665                 670                 675

TGT TCC TTC ACA ACC CTA CCA GCC TTG TCC ACC GGC CTC ATC CAC CTC        2417
Cys Ser Phe Thr Thr Leu Pro Ala Leu Ser Thr Gly Leu Ile His Leu
            680                 685                 690

CAC CAG AAC ATT GTG GAC GTG CAG TAC TTG TAC GGG GTG GGG TCA AGC        2465
His Gln Asn Ile Val Asp Val Gln Tyr Leu Tyr Gly Val Gly Ser Ser
        695                 700                 705

ATC GCG TCC TGG GCC ATT AAG TGG GAG TAC GTC GTT CTC CTG TTC CTT        2513
Ile Ala Ser Trp Ala Ile Lys Trp Glu Tyr Val Val Leu Leu Phe Leu
    710             715                 720

CTG CTT GCA GAC GCG CGC GTC TGC TCC TGC TTG TGG ATG ATG CTA CTC        2561
Leu Leu Ala Asp Ala Arg Val Cys Ser Cys Leu Trp Met Met Leu Leu
725             730                 735                 740

ATA TCC CAA GCG GAG GCG GCT TTG GAG AAC CTC GTA ATA CTT AAT GCA        2609
Ile Ser Gln Ala Glu Ala Ala Leu Glu Asn Leu Val Ile Leu Asn Ala
                745                 750                 755

GCA TCC CTG GCC GGG ACG CAC GGT CTT GTA TCC TTC CTC GTG TTC TTC        2657
Ala Ser Leu Ala Gly Thr His Gly Leu Val Ser Phe Leu Val Phe Phe
            760                 765                 770

TGC TTT GCA TGG TAT TTG AAG GGT AAG TGG GTG CCC GGA GCG GTC TAC        2705
Cys Phe Ala Trp Tyr Leu Lys Gly Lys Trp Val Pro Gly Ala Val Tyr
        775                 780                 785

ACC TTC TAC GGG ATG TGG CCT CTC CTC CTG CTC CTG TTG GCG TTG CCC        2753
Thr Phe Tyr Gly Met Trp Pro Leu Leu Leu Leu Leu Ala Leu Pro
    790             795                 800

CAG CGG GCG TAC GCG CTG GAC ACG GAG GTG GCC GCG TCG TGT GGC GGT        2801
Gln Arg Ala Tyr Ala Leu Asp Thr Glu Val Ala Ala Ser Cys Gly Gly
805             810                 815                 820

GTT GTT CTC GTC GGG TTG ATG GCG CTG ACT CTG TCA CCA TAT TAC AAG        2849
Val Val Leu Val Gly Leu Met Ala Leu Thr Leu Ser Pro Tyr Tyr Lys
                825                 830                 835

CGC TAT ATC AGC TGG TGC TTG TGG TGG CTT CAG TAT TTT CTG ACC AGA        2897
Arg Tyr Ile Ser Trp Cys Leu Trp Trp Leu Gln Tyr Phe Leu Thr Arg
            840                 845                 850

GTG GAA GCG CAA CTG CAC GTG TGG ATT CCC CCC CTC AAC GTC CGA GGG        2945
Val Glu Ala Gln Leu His Val Trp Ile Pro Pro Leu Asn Val Arg Gly
        855                 860                 865

GGG CGC GAC GCC GTC ATC TTA CTC ATG TGT GCT GTA CAC CCG ACT CTG        2993
Gly Arg Asp Ala Val Ile Leu Leu Met Cys Ala Val His Pro Thr Leu
    870             875                 880

GTA TTT GAC ATC ACC AAA TTG CTG CTG GCC GTC TTC GGA CCC CTT TGG        3041
Val Phe Asp Ile Thr Lys Leu Leu Leu Ala Val Phe Gly Pro Leu Trp
885             890                 895                 900

ATT CTT CAA GCC AGT TTG CTT AAA GTA CCC TAC TTT GTG CGC GTC CAA        3089
Ile Leu Gln Ala Ser Leu Leu Lys Val Pro Tyr Phe Val Arg Val Gln
                905                 910                 915

GGC CTT CTC CGG TTC TGC GCG TTA GCG CGG AAG ATG ATC GGA GGC CAT        3137
Gly Leu Leu Arg Phe Cys Ala Leu Ala Arg Lys Met Ile Gly Gly His
            920                 925                 930
```

```
TAC GTG CAA ATG GTC ATC ATT AAG TTA GGG GCG CTT ACT GGC ACC TAT      3185
Tyr Val Gln Met Val Ile Ile Lys Leu Gly Ala Leu Thr Gly Thr Tyr
        935             940                 945

GTT TAT AAC CAT CTC ACT CCT CTT CGG GAC TGG GCG CAC AAC GGC TTG      3233
Val Tyr Asn His Leu Thr Pro Leu Arg Asp Trp Ala His Asn Gly Leu
950             955                 960

CGA GAT CTG GCC GTG GCT GTA GAG CCA GTC GTC TTC TCC CAA ATG GAG      3281
Arg Asp Leu Ala Val Ala Val Glu Pro Val Val Phe Ser Gln Met Glu
965                 970             975                 980

ACC AAG CTC ATC ACG TGG GGG GCA GAT ACC GCC GCG TGC GGT GAC ATC      3329
Thr Lys Leu Ile Thr Trp Gly Ala Asp Thr Ala Ala Cys Gly Asp Ile
                985                 990                 995

ATC AAC GGC TTG CCT GTT TCC GCC CGC AGG GGC CGG GAG ATA CTG CTC      3377
Ile Asn Gly Leu Pro Val Ser Ala Arg Arg Gly Arg Glu Ile Leu Leu
            1000                1005                1010

GGG CCA GCC GAT GGA ATG GTC TCC AAG GGG TGG AGG TTG CTG GCG CCC      3425
Gly Pro Ala Asp Gly Met Val Ser Lys Gly Trp Arg Leu Leu Ala Pro
        1015                1020                1025

ATC ACG GCG TAC GCC CAG CAG ACA AGG GGC CTC CTA GGG TGC ATA ATC      3473
Ile Thr Ala Tyr Ala Gln Gln Thr Arg Gly Leu Leu Gly Cys Ile Ile
        1030                1035                1040

ACC AGC CTA ACT GGC CGG GAC AAA AAC CAA GTG GAG GGT GAG GTC CAG      3521
Thr Ser Leu Thr Gly Arg Asp Lys Asn Gln Val Glu Gly Glu Val Gln
1045                1050                1055                1060

ATT GTG TCA ACT GCT GCC CAA ACC TTC CTG GCA ACG TGC ATC AAT GGG      3569
Ile Val Ser Thr Ala Ala Gln Thr Phe Leu Ala Thr Cys Ile Asn Gly
                1065                1070                1075

GTG TGC TGG ACT GTC TAC CAC GGG GCC GGA ACG AGG ACC ATC GCG TCA      3617
Val Cys Trp Thr Val Tyr His Gly Ala Gly Thr Arg Thr Ile Ala Ser
            1080                1085                1090

CCC AAG GGT CCT GTC ATC CAG ATG TAT ACC AAT GTA GAC CAA GAC CTT      3665
Pro Lys Gly Pro Val Ile Gln Met Tyr Thr Asn Val Asp Gln Asp Leu
        1095                1100                1105

GTG GGC TGG CCC GCT CCG CAA GGT AGC CGC TCA TTG ACA CCC TGC ACT      3713
Val Gly Trp Pro Ala Pro Gln Gly Ser Arg Ser Leu Thr Pro Cys Thr
        1110                1115                1120

TGC GGC TCC TCG GAC CTT TAC CTG GTC ACG AGG CAC GCC GAT GTC ATT      3761
Cys Gly Ser Ser Asp Leu Tyr Leu Val Thr Arg His Ala Asp Val Ile
1125                1130                1135                1140

CCC GTG CGC CGG CGG GGT GAT AGC AGG GGC AGC CTG CTG TCG CCC CGG      3809
Pro Val Arg Arg Arg Gly Asp Ser Arg Gly Ser Leu Leu Ser Pro Arg
                1145                1150                1155

CCC ATT TCC TAC TTG AAA GGC TCC TCG GGG GGT CCG CTG TTG TGC CCC      3857
Pro Ile Ser Tyr Leu Lys Gly Ser Ser Gly Gly Pro Leu Leu Cys Pro
            1160                1165                1170

GCG GGG CAC GCC GTG GGC ATA TTT AGG GCC GCG GTG TGC ACC CGT GGA      3905
Ala Gly His Ala Val Gly Ile Phe Arg Ala Ala Val Cys Thr Arg Gly
        1175                1180                1185

GTG GCT AAG GCG GTG GAC TTT ATC CCT GTG GAG AAC CTA GAG ACA ACC      3953
Val Ala Lys Ala Val Asp Phe Ile Pro Val Glu Asn Leu Glu Thr Thr
        1190                1195                1200

ATG AGG TCC CCG GTG TTC ACG GAT AAC TCC TCT CCA CCA GTA GTG CCC      4001
Met Arg Ser Pro Val Phe Thr Asp Asn Ser Ser Pro Pro Val Val Pro
1205                1210                1215                1220

CAG AGC TTC CAG GTG GCT CAC CTC CAT GCT CCC ACA GGC AGC GGC AAA      4049
Gln Ser Phe Gln Val Ala His Leu His Ala Pro Thr Gly Ser Gly Lys
                1225                1230                1235

AGC ACC AAG GTC CCG GCT GCA TAT GCA GCT CAG GGC TAT AAG GTG CTA      4097
Ser Thr Lys Val Pro Ala Ala Tyr Ala Ala Gln Gly Tyr Lys Val Leu
            1240                1245                1250
```

```
GTA CTC AAC CCC TCT GTT GCT GCA ACA CTG GGC TTT GGT GCT TAC ATG    4145
Val Leu Asn Pro Ser Val Ala Ala Thr Leu Gly Phe Gly Ala Tyr Met
        1255            1260                1265

TCC AAG GCT CAT GGG ATC GAT CCT AAC ATC AGG ACC GGG GTG AGA ACA    4193
Ser Lys Ala His Gly Ile Asp Pro Asn Ile Arg Thr Gly Val Arg Thr
    1270            1275                1280

ATT ACC ACT GGC AGC CCC ATC ACG TAC TCC ACC TAC GGC AAG TTC CTT    4241
Ile Thr Thr Gly Ser Pro Ile Thr Tyr Ser Thr Tyr Gly Lys Phe Leu
1285            1290                1295                1300

GCC GAC GGC GGG TGC TCG GGG GGC GCT TAT GAC ATA ATA ATT TGT GAC    4289
Ala Asp Gly Gly Cys Ser Gly Gly Ala Tyr Asp Ile Ile Ile Cys Asp
                1305                1310                1315

GAG TGC CAC TCC ACG GAT GCC ACA TCC ATC TTG GGC ATC GGC ACT GTC    4337
Glu Cys His Ser Thr Asp Ala Thr Ser Ile Leu Gly Ile Gly Thr Val
            1320                1325                1330

CTT GAC CAA GCA GAG ACT GCG GGG GCG AGA CTG GTT GTG CTC GCC ACC    4385
Leu Asp Gln Ala Glu Thr Ala Gly Ala Arg Leu Val Val Leu Ala Thr
                1335                1340                1345

GCC ACC CCT CCG GGC TCC GTC ACT GTG CCC CAT CCC AAC ATC GAG GAG    4433
Ala Thr Pro Pro Gly Ser Val Thr Val Pro His Pro Asn Ile Glu Glu
1350                1355                1360

GTT GCT CTG TCC ACC ACC GGA GAG ATC CCT TTT TAC GGC AAG GCT ATC    4481
Val Ala Leu Ser Thr Thr Gly Glu Ile Pro Phe Tyr Gly Lys Ala Ile
1365                1370                1375                1380

CCC CTC GAA GTA ATC AAG GGG GGG AGA CAT CTC ATC TTC TGT CAT TCA    4529
Pro Leu Glu Val Ile Lys Gly Gly Arg His Leu Ile Phe Cys His Ser
                    1385                1390                1395

AAG AAG AAG TGC GAC GAA CTC GCC GCA AAG CTG GTC GCA TTG GGC ATC    4577
Lys Lys Lys Cys Asp Glu Leu Ala Ala Lys Leu Val Ala Leu Gly Ile
                1400                1405                1410

AAT GCC GTG GCC TAC TAC CGC GGT CTT GAC GTG TCC GTC ATC CCG ACC    4625
Asn Ala Val Ala Tyr Tyr Arg Gly Leu Asp Val Ser Val Ile Pro Thr
                1415                1420                1425

AGC GGC GAT GTT GTC GTC GTG GCA ACC GAT GCC CTC ATG ACC GGC TAT    4673
Ser Gly Asp Val Val Val Val Ala Thr Asp Ala Leu Met Thr Gly Tyr
    1430                1435                1440

ACC GGC GAC TTC GAC TCG GTG ATA GAC TGC AAT ACG TGT GTC ACC CAG    4721
Thr Gly Asp Phe Asp Ser Val Ile Asp Cys Asn Thr Cys Val Thr Gln
1445                1450                1455                1460

ACA GTC GAT TTC AGC CTT GAC CCT ACC TTC ACC ATT GAG ACA ATC ACG    4769
Thr Val Asp Phe Ser Leu Asp Pro Thr Phe Thr Ile Glu Thr Ile Thr
                1465                1470                1475

CTC CCC CAG GAT GCT GTC TCC CGC ACT CAA CGT CGG GGC AGG ACT GGC    4817
Leu Pro Gln Asp Ala Val Ser Arg Thr Gln Arg Arg Gly Arg Thr Gly
                1480                1485                1490

AGG GGG AAG CCA GGC ATC TAC AGA TTT GTG GCA CCG GGG GAG CGC CCC    4865
Arg Gly Lys Pro Gly Ile Tyr Arg Phe Val Ala Pro Gly Glu Arg Pro
                1495                1500                1505

TCC GGC ATG TTC GAC TCG TCC GTC CTC TGT GAG TGC TAT GAC GCA GGC    4913
Ser Gly Met Phe Asp Ser Ser Val Leu Cys Glu Cys Tyr Asp Ala Gly
    1510                1515                1520

TGT GCT TGG TAT GAG CTC ACG CCC GCC GAG ACT ACA GTT AGG CTA CGA    4961
Cys Ala Trp Tyr Glu Leu Thr Pro Ala Glu Thr Thr Val Arg Leu Arg
1525                1530                1535                1540

GCG TAC ATG AAC ACC CCG GGG CTT CCC GTG TGC CAG GAC CAT CTT GAA    5009
Ala Tyr Met Asn Thr Pro Gly Leu Pro Val Cys Gln Asp His Leu Glu
                1545                1550                1555

TTT TGG GAG GGC GTC TTT ACA GGC CTC ACT CAT ATA GAT GCC CAC TTT    5057
Phe Trp Glu Gly Val Phe Thr Gly Leu Thr His Ile Asp Ala His Phe
                1560                1565                1570
```

```
CTA TCC CAG ACA AAG CAG AGT GGG GAG AAC CTT CCT TAC CTG GTA GCG      5105
Leu Ser Gln Thr Lys Gln Ser Gly Glu Asn Leu Pro Tyr Leu Val Ala
        1575                1580                1585

TAC CAA GCC ACC GTG TGC GCT AGG GCT CAA GCC CCT CCC CCA TCG TGG      5153
Tyr Gln Ala Thr Val Cys Ala Arg Ala Gln Ala Pro Pro Pro Ser Trp
1590                1595                1600

GAC CAG ATG TGG AAG TGT TTG ATT CGC CTC AAG CCC ACC CTC CAT GGG      5201
Asp Gln Met Trp Lys Cys Leu Ile Arg Leu Lys Pro Thr Leu His Gly
1605                1610                1615                1620

CCA ACA CCC CTG CTA TAC AGA CTG GGC GCT GTT CAG AAT GAA ATC ACC      5249
Pro Thr Pro Leu Leu Tyr Arg Leu Gly Ala Val Gln Asn Glu Ile Thr
            1625                1630                1635

CTG ACG CAC CCA GTC ACC AAA TAC ATC ATG ACA TGC ATG TCG GCC GAC      5297
Leu Thr His Pro Val Thr Lys Tyr Ile Met Thr Cys Met Ser Ala Asp
        1640                1645                1650

CTG GAG GTC GTC ACG AGC ACC TGG GTG CTC GTT GGC GGC GTC CTG GCT      5345
Leu Glu Val Val Thr Ser Thr Trp Val Leu Val Gly Gly Val Leu Ala
    1655                1660                1665

GCT TTG GCC GCG TAT TGC CTG TCA ACA GGC TGC GTG GTC ATA GTG GGC      5393
Ala Leu Ala Ala Tyr Cys Leu Ser Thr Gly Cys Val Val Ile Val Gly
1670                1675                1680

AGG GTC GTC TTG TCC GGG AAG CCG GCA ATC ATA CCT GAC AGG GAA GTC      5441
Arg Val Val Leu Ser Gly Lys Pro Ala Ile Ile Pro Asp Arg Glu Val
1685                1690                1695                1700

CTC TAC CGA GAG TTC GAT GAG ATG GAA GAG TGC TCT CAG CAC TTA CCG      5489
Leu Tyr Arg Glu Phe Asp Glu Met Glu Glu Cys Ser Gln His Leu Pro
            1705                1710                1715

TAC ATC GAG CAA GGG ATG ATG CTC GCC GAG CAG TTC AAG CAG AAG GCC      5537
Tyr Ile Glu Gln Gly Met Met Leu Ala Glu Gln Phe Lys Gln Lys Ala
        1720                1725                1730

CTC GGC CTC CTG CAG ACC GCG TCC CGT CAG GCA GAG GTT ATC GCC CCT      5585
Leu Gly Leu Leu Gln Thr Ala Ser Arg Gln Ala Glu Val Ile Ala Pro
    1735                1740                1745

GCT GTC CAG ACC AAC TGG CAA AAA CTC GAG ACC TTC TGG GCG AAG CAT      5633
Ala Val Gln Thr Asn Trp Gln Lys Leu Glu Thr Phe Trp Ala Lys His
1750                1755                1760

ATG TGG AAC TTC ATC AGT GGG ATA CAA TAC TTG GCG GGC TTG TCA ACG      5681
Met Trp Asn Phe Ile Ser Gly Ile Gln Tyr Leu Ala Gly Leu Ser Thr
1765                1770                1775                1780

CTG CCT GGT AAC CCC GCC ATT GCT TCA TTG ATG GCT TTT ACA GCT GCT      5729
Leu Pro Gly Asn Pro Ala Ile Ala Ser Leu Met Ala Phe Thr Ala Ala
            1785                1790                1795

GTC ACC AGC CCA CTA ACC ACT AGC CAA ACC CTC CTC TTC AAC ATA TTG      5777
Val Thr Ser Pro Leu Thr Thr Ser Gln Thr Leu Leu Phe Asn Ile Leu
        1800                1805                1810

GGG GGG TGG GTG GCT GCC CAG CTC GCC GCC CCC GGT GCC GCT ACT GCC      5825
Gly Gly Trp Val Ala Ala Gln Leu Ala Ala Pro Gly Ala Ala Thr Ala
    1815                1820                1825

TTT GTG GGC GCT GGC TTA GCT GGC GCC GCC ATC GGC AGT GTT GGA CTG      5873
Phe Val Gly Ala Gly Leu Ala Gly Ala Ala Ile Gly Ser Val Gly Leu
1830                1835                1840

GGG AAG GTC CTC ATA GAC ATC CTT GCA GGG TAT GGC GCG GGC GTG GCG      5921
Gly Lys Val Leu Ile Asp Ile Leu Ala Gly Tyr Gly Ala Gly Val Ala
1845                1850                1855                1860

GGA GCT CTT GTG GCA TTC AAG ATC ATG AGC GGT GAG GTC CCC TCC ACG      5969
Gly Ala Leu Val Ala Phe Lys Ile Met Ser Gly Glu Val Pro Ser Thr
            1865                1870                1875

GAG GAC CTG GTC AAT CTA CTG CCC GCC ATC CTC TCG CCC GGA GCC CTC      6017
Glu Asp Leu Val Asn Leu Leu Pro Ala Ile Leu Ser Pro Gly Ala Leu
        1880                1885                1890
```

```
GTA GTC GGC GTG GTC TGT GCA GCA ATA CTG CGC CGG CAC GTT GGC CCG      6065
Val Val Gly Val Val Cys Ala Ala Ile Leu Arg Arg His Val Gly Pro
            1895                1900                1905

GGC GAG GGG GCA GTG CAG TGG ATG AAC CGG CTG ATA GCC TTC GCC TCC      6113
Gly Glu Gly Ala Val Gln Trp Met Asn Arg Leu Ile Ala Phe Ala Ser
1910                1915                1920

CGG GGG AAC CAT GTT TCC CCC ACG CAC TAC GTG CCG GAG AGC GAT GCA      6161
Arg Gly Asn His Val Ser Pro Thr His Tyr Val Pro Glu Ser Asp Ala
1925                1930                1935                1940

GCT GCC CGC GTC ACT GCC ATA CTC AGC AGC CTC ACT GTA ACC CAG CTC      6209
Ala Ala Arg Val Thr Ala Ile Leu Ser Ser Leu Thr Val Thr Gln Leu
                1945                1950                1955

CTG AGG CGA CTG CAC CAG TGG ATA AGC TCG GAG TGT ACC ACT CCA TGC      6257
Leu Arg Arg Leu His Gln Trp Ile Ser Ser Glu Cys Thr Thr Pro Cys
            1960                1965                1970

TCC GGT TCC TGG CTA AGG GAC ATC TGG GAC TGG ATA TGC GAG GTG TTG      6305
Ser Gly Ser Trp Leu Arg Asp Ile Trp Asp Trp Ile Cys Glu Val Leu
        1975                1980                1985

AGC GAC TTT AAG ACC TGG CTA AAA GCT AAG CTC ATG CCA CAG CTG CCT      6353
Ser Asp Phe Lys Thr Trp Leu Lys Ala Lys Leu Met Pro Gln Leu Pro
    1990                1995                2000

GGG ATC CCC TTT GTG TCC TGC CAG CGC GGG TAT AAG GGG GTC TGG CGA      6401
Gly Ile Pro Phe Val Ser Cys Gln Arg Gly Tyr Lys Gly Val Trp Arg
2005                2010                2015                2020

GTG GAC GGC ATC ATG CAC ACT CGC TGC CAC TGT GGA GCT GAG ATC ACT      6449
Val Asp Gly Ile Met His Thr Arg Cys His Cys Gly Ala Glu Ile Thr
                2025                2030                2035

GGA CAT GTC AAA AAC GGG ACG ATG AGG ATC GTC GGT CCT AGG ACC TGC      6497
Gly His Val Lys Asn Gly Thr Met Arg Ile Val Gly Pro Arg Thr Cys
            2040                2045                2050

AGG AAC ATG TGG AGT GGG ACC TTC CCC ATT AAT GCC TAC ACC ACG GGC      6545
Arg Asn Met Trp Ser Gly Thr Phe Pro Ile Asn Ala Tyr Thr Thr Gly
        2055                2060                2065

CCC TGT ACC CCC CTT CCT GCG CCG AAC TAC ACG TTC GCG CTA TGG AGG      6593
Pro Cys Thr Pro Leu Pro Ala Pro Asn Tyr Thr Phe Ala Leu Trp Arg
    2070                2075                2080

GTG TCT GCA GAG GAA TAT GTG GAG ATA AGG CAG GTG GGG GAC TTC CAC      6641
Val Ser Ala Glu Glu Tyr Val Glu Ile Arg Gln Val Gly Asp Phe His
2085                2090                2095                2100

TAC GTG ACG GGT ATG ACT ACT GAC AAT CTC AAA TGC CCG TGC CAG GTC      6689
Tyr Val Thr Gly Met Thr Thr Asp Asn Leu Lys Cys Pro Cys Gln Val
                2105                2110                2115

CCA TCG CCC GAA TTT TTC ACA GAA TTG GAC GGG GTG CGC CTA CAT AGG      6737
Pro Ser Pro Glu Phe Phe Thr Glu Leu Asp Gly Val Arg Leu His Arg
            2120                2125                2130

TTT GCG CCC CCC TGC AAG CCC TTG CTG CGG GAG GAG GTA TCA TTC AGA      6785
Phe Ala Pro Pro Cys Lys Pro Leu Leu Arg Glu Glu Val Ser Phe Arg
        2135                2140                2145

GTA GGA CTC CAC GAA TAC CCG GTA GGG TCG CAA TTA CCT TGC GAG CCC      6833
Val Gly Leu His Glu Tyr Pro Val Gly Ser Gln Leu Pro Cys Glu Pro
    2150                2155                2160

GAA CCG GAC GTG GCC GTG TTG ACG TCC ATG CTC ACT GAT CCC TCC CAT      6881
Glu Pro Asp Val Ala Val Leu Thr Ser Met Leu Thr Asp Pro Ser His
2165                2170                2175                2180

ATA ACA GCA GAG GCG GCC GGG CGA AGG TTG GCG AGG GGA TCA CCC CCC      6929
Ile Thr Ala Glu Ala Ala Gly Arg Arg Leu Ala Arg Gly Ser Pro Pro
                2185                2190                2195

TCT GTG GCC AGC TCC TCG GCT AGC CAG CTA TCC GCT CCA TCT CTC AAG      6977
Ser Val Ala Ser Ser Ser Ala Ser Gln Leu Ser Ala Pro Ser Leu Lys
            2200                2205                2210
```

```
GCA ACT TGC ACC GCT AAC CAT GAC TCC CCT GAT GCT GAG CTC ATA GAG    7025
Ala Thr Cys Thr Ala Asn His Asp Ser Pro Asp Ala Glu Leu Ile Glu
        2215                2220                2225

GCC AAC CTC CTA TGG AGG CAG GAG ATG GGC GGC AAC ATC ACC AGG GTT    7073
Ala Asn Leu Leu Trp Arg Gln Glu Met Gly Gly Asn Ile Thr Arg Val
2230                2235                2240

GAG TCA GAA AAC AAA GTG GTG ATT CTG GAC TCC TTC GAT CCG CTT GTG    7121
Glu Ser Glu Asn Lys Val Val Ile Leu Asp Ser Phe Asp Pro Leu Val
2245                2250                2255                2260

GCG GAG GAG GAC GAG CGG GAG ATC TCC GTA CCC GCA GAA ATC CTG CGG    7169
Ala Glu Glu Asp Glu Arg Glu Ile Ser Val Pro Ala Glu Ile Leu Arg
                2265                2270                2275

AAG TCT CGG AGA TTC GCC CAG GCC CTG CCC GTT TGG GCG CGG CCG GAC    7217
Lys Ser Arg Arg Phe Ala Gln Ala Leu Pro Val Trp Ala Arg Pro Asp
        2280                2285                2290

TAT AAC CCC CCG CTA GTG GAG ACG TGG AAA AAG CCC GAC TAC GAA CCA    7265
Tyr Asn Pro Pro Leu Val Glu Thr Trp Lys Lys Pro Asp Tyr Glu Pro
        2295                2300                2305

CCT GTG GTC CAT GGC TGT CCG CTT CCA CCT CCA AAG TCC CCT CCT GTG    7313
Pro Val Val His Gly Cys Pro Leu Pro Pro Pro Lys Ser Pro Pro Val
        2310                2315                2320

CCT CCG CCT CGG AAG AAG CGG ACG GTG GTC CTC ACT GAA TCA ACC CTA    7361
Pro Pro Pro Arg Lys Lys Arg Thr Val Val Leu Thr Glu Ser Thr Leu
2325                2330                2335                2340

TCT ACT GCC TTG GCC GAG CTC GCC ACC AGA AGC TTT GGC AGC TCC TCA    7409
Ser Thr Ala Leu Ala Glu Leu Ala Thr Arg Ser Phe Gly Ser Ser Ser
                2345                2350                2355

ACT TCC GGC ATT ACG GGC GAC AAT ACG ACA ACA TCC TCT GAG CCC GCC    7457
Thr Ser Gly Ile Thr Gly Asp Asn Thr Thr Thr Ser Ser Glu Pro Ala
        2360                2365                2370

CCT TCT GGC TGC CCC CCC GAC TCC GAC GCT GAG TCC TAT TCC TCC ATG    7505
Pro Ser Gly Cys Pro Pro Asp Ser Asp Ala Glu Ser Tyr Ser Ser Met
        2375                2380                2385

CCC CCC CTG GAG GGG GAG CCT GGG GAT CCG GAT CTT AGC GAC GGG TCA    7553
Pro Pro Leu Glu Gly Glu Pro Gly Asp Pro Asp Leu Ser Asp Gly Ser
        2390                2395                2400

TGG TCA ACG GTC AGT AGT GAG GCC AAC GCG GAG GAT GTC GTG TGC TGC    7601
Trp Ser Thr Val Ser Ser Glu Ala Asn Ala Glu Asp Val Val Cys Cys
2405                2410                2415                2420

TCA ATG TCT TAC TCT TGG ACA GGC GCA CTC GTC ACC CCG TGC GCC GCG    7649
Ser Met Ser Tyr Ser Trp Thr Gly Ala Leu Val Thr Pro Cys Ala Ala
                2425                2430                2435

GAA GAA CAG AAA CTG CCC ATC AAT GCA CTA AGC AAC TCG TTG CTA CGT    7697
Glu Glu Gln Lys Leu Pro Ile Asn Ala Leu Ser Asn Ser Leu Leu Arg
                2440                2445                2450

CAC CAC AAT TTG GTG TAT TCC ACC ACC TCA CGC AGT GCT TGC CAA AGG    7745
His His Asn Leu Val Tyr Ser Thr Thr Ser Arg Ser Ala Cys Gln Arg
        2455                2460                2465

CAG AAG AAA GTC ACA TTT GAC AGA CTG CAA GTT CTG GAC AGC CAT TAC    7793
Gln Lys Lys Val Thr Phe Asp Arg Leu Gln Val Leu Asp Ser His Tyr
        2470                2475                2480

CAG GAC GTA CTC AAG GAG GTT AAA GCA GCG GCG TCA AAA GTG AAG GCT    7841
Gln Asp Val Leu Lys Glu Val Lys Ala Ala Ala Ser Lys Val Lys Ala
2485                2490                2495                2500

AAC TTG CTA TCC GTA GAG GAA GCT TGC AGC CTG ACG CCC CCA CAC TCA    7889
Asn Leu Leu Ser Val Glu Glu Ala Cys Ser Leu Thr Pro Pro His Ser
                2505                2510                2515

GCC AAA TCC AAG TTT GGT TAT GGG GCA AAA GAC GTC CGT TGC CAT GCC    7937
Ala Lys Ser Lys Phe Gly Tyr Gly Ala Lys Asp Val Arg Cys His Ala
        2520                2525                2530
```

```
AGA AAG GCC GTA ACC CAC ATC AAC TCC GTG TGG AAA GAC CTT CTG GAA      7985
Arg Lys Ala Val Thr His Ile Asn Ser Val Trp Lys Asp Leu Leu Glu
        2535            2540                2545

GAC AAT GTA ACA CCA ATA GAC ACT ACC ATC ATG GCT AAG AAC GAG GTT      8033
Asp Asn Val Thr Pro Ile Asp Thr Thr Ile Met Ala Lys Asn Glu Val
        2550            2555                2560

TTC TGC GTT CAG CCT GAG AAG GGG GGT CGT AAG CCA GCT CGT CTC ATC      8081
Phe Cys Val Gln Pro Glu Lys Gly Gly Arg Lys Pro Ala Arg Leu Ile
2565            2570                2575                2580

GTG TTC CCC GAT CTG GGC GTG CGC GTG TGC GAA AAG ATG GCT TTG TAC      8129
Val Phe Pro Asp Leu Gly Val Arg Val Cys Glu Lys Met Ala Leu Tyr
                2585                2590                2595

GAC GTG GTT ACA AAG CTC CCC TTG GCC GTG ATG GGA AGC TCC TAC GGA      8177
Asp Val Val Thr Lys Leu Pro Leu Ala Val Met Gly Ser Ser Tyr Gly
        2600            2605                2610

TTC CAA TAC TCA CCA GGA CAG CGG GTT GAA TTC CTC GTG CAA GCG TGG      8225
Phe Gln Tyr Ser Pro Gly Gln Arg Val Glu Phe Leu Val Gln Ala Trp
        2615            2620                2625

AAG TCC AAG AAA ACC CCA ATG GGG TTC TCG TAT GAT ACC CGC TGC TTT      8273
Lys Ser Lys Lys Thr Pro Met Gly Phe Ser Tyr Asp Thr Arg Cys Phe
        2630            2635                2640

GAC TCC ACA GTC ACT GAG AGC GAC ATC CGT ACG GAG GAG GCA ATC TAC      8321
Asp Ser Thr Val Thr Glu Ser Asp Ile Arg Thr Glu Glu Ala Ile Tyr
2645            2650                2655                2660

CAA TGT TGT GAC CTC GAC CCC CAA GCC CGC GTG GCC ATC AAG TCC CTC      8369
Gln Cys Cys Asp Leu Asp Pro Gln Ala Arg Val Ala Ile Lys Ser Leu
                2665                2670                2675

ACC GAG AGG CTT TAT GTT GGG GGC CCT CTT ACC AAT TCA AGG GGG GAG      8417
Thr Glu Arg Leu Tyr Val Gly Gly Pro Leu Thr Asn Ser Arg Gly Glu
        2680            2685                2690

AAC TGC GGC TAT CGC AGG TGC CGC GCG AGC GGC GTA CTG ACA ACT AGC      8465
Asn Cys Gly Tyr Arg Arg Cys Arg Ala Ser Gly Val Leu Thr Thr Ser
        2695            2700                2705

TGT GGT AAC ACC CTC ACT TGC TAC ATC AAG GCC CGG GCA GCC TGT CGA      8513
Cys Gly Asn Thr Leu Thr Cys Tyr Ile Lys Ala Arg Ala Ala Cys Arg
        2710            2715                2720

GCC GCA GGG CTC CAG GAC TGC ACC ATG CTC GTG TGT GGC GAC GAC TTA      8561
Ala Ala Gly Leu Gln Asp Cys Thr Met Leu Val Cys Gly Asp Asp Leu
2725            2730                2735                2740

GTC GTT ATC TGT GAA AGC GCG GGG GTC CAG GAG GAC GCG GCG AGC CTG      8609
Val Val Ile Cys Glu Ser Ala Gly Val Gln Glu Asp Ala Ala Ser Leu
                2745                2750                2755

AGA GCC TTC ACG GAG GCT ATG ACC AGG TAC TCC GCC CCC CCT GGG GAC      8657
Arg Ala Phe Thr Glu Ala Met Thr Arg Tyr Ser Ala Pro Pro Gly Asp
        2760            2765                2770

CCC CCA CAA CCA GAA TAC GAC TTG GAG CTC ATA ACA TCA TGC TCC TCC      8705
Pro Pro Gln Pro Glu Tyr Asp Leu Glu Leu Ile Thr Ser Cys Ser Ser
        2775            2780                2785

AAC GTG TCA GTC GCC CAC GAC GGC GCT GGA AAG AGG GTC TAC TAC CTC      8753
Asn Val Ser Val Ala His Asp Gly Ala Gly Lys Arg Val Tyr Tyr Leu
        2790            2795                2800

ACC CGT GAC CCT ACA ACC CCC CTC GCG AGA GCT GCG TGG GAG ACA GCA      8801
Thr Arg Asp Pro Thr Thr Pro Leu Ala Arg Ala Ala Trp Glu Thr Ala
2805            2810                2815                2820

AGA CAC ACT CCA GTC AAT TCC TGG CTA GGC AAC ATA ATC ATG TTT GCC      8849
Arg His Thr Pro Val Asn Ser Trp Leu Gly Asn Ile Ile Met Phe Ala
                2825                2830                2835

CCC ACA CTG TGG GCG AGG ATG ATA CTG ATG ACC CAT TTC TTT AGC GTC      8897
Pro Thr Leu Trp Ala Arg Met Ile Leu Met Thr His Phe Phe Ser Val
        2840            2845                2850
```

| | | | | | | | | | | | | | | | | |
|---|---|---|---|---|---|---|---|---|---|---|---|---|---|---|---|---|
| CTT | ATA | GCC | AGG | GAC | CAG | CTT | GAA | CAG | GCC | CTC | GAT | TGC | GAG | ATC | TAC | 8945 |
| Leu | Ile | Ala | Arg | Asp | Gln | Leu | Glu | Gln | Ala | Leu | Asp | Cys | Glu | Ile | Tyr | |
| | | 2855 | | | 2860 | | | | | 2865 | | | | | | |
| GGG | GCC | TGC | TAC | TCC | ATA | GAA | CCA | CTT | GAT | CTA | CCT | CCA | ATC | ATT | CAA | 8993 |
| Gly | Ala | Cys | Tyr | Ser | Ile | Glu | Pro | Leu | Asp | Leu | Pro | Pro | Ile | Ile | Gln | |
| | | 2870 | | | 2875 | | | | | 2880 | | | | | | |
| AGA | CTC | CAT | GGC | CTC | AGC | GCA | TTT | TCA | CTC | CAC | AGT | TAC | TCT | CCA | GGT | 9041 |
| Arg | Leu | His | Gly | Leu | Ser | Ala | Phe | Ser | Leu | His | Ser | Tyr | Ser | Pro | Gly | |
| 2885 | | | | 2890 | | | | | 2895 | | | | | | 2900 | |
| GAA | ATT | AAT | AGG | GTG | GCC | GCA | TGC | CTC | AGA | AAA | CTT | GGG | GTA | CCG | CCC | 9089 |
| Glu | Ile | Asn | Arg | Val | Ala | Ala | Cys | Leu | Arg | Lys | Leu | Gly | Val | Pro | Pro | |
| | | 2905 | | | | | 2910 | | | | | 2915 | | | | |
| TTG | CGA | GCT | TGG | AGA | CAC | CGG | GCC | CGG | AGC | GTC | CGC | GCT | AGG | CTT | CTG | 9137 |
| Leu | Arg | Ala | Trp | Arg | His | Arg | Ala | Arg | Ser | Val | Arg | Ala | Arg | Leu | Leu | |
| | | 2920 | | | | | 2925 | | | | | 2930 | | | | |
| GCC | AGA | GGA | GGC | AGG | GCT | GCC | ATA | TGT | GGC | AAG | TAC | CTC | TTC | AAC | TGG | 9185 |
| Ala | Arg | Gly | Gly | Arg | Ala | Ala | Ile | Cys | Gly | Lys | Tyr | Leu | Phe | Asn | Trp | |
| | | 2935 | | | | | 2940 | | | | | 2945 | | | | |
| GCA | GTA | AGA | ACA | AAG | CTC | AAA | CTC | ACT | CCA | ATA | GCG | GCC | GCT | GGC | CAG | 9233 |
| Ala | Val | Arg | Thr | Lys | Leu | Lys | Leu | Thr | Pro | Ile | Ala | Ala | Ala | Gly | Gln | |
| | | 2950 | | | | | 2955 | | | | | 2960 | | | | |
| CTG | GAC | TTG | TCC | GGC | TGG | TTC | ACG | GCT | GGC | TAC | AGC | GGG | GGA | GAC | ATT | 9281 |
| Leu | Asp | Leu | Ser | Gly | Trp | Phe | Thr | Ala | Gly | Tyr | Ser | Gly | Gly | Asp | Ile | |
| 2965 | | | | 2970 | | | | | 2975 | | | | | | 2980 | |
| TAT | CAC | AGC | GTG | TCT | CAT | GCC | CGG | CCC | CGC | TGG | ATC | TGG | TTT | TGC | CTA | 9329 |
| Tyr | His | Ser | Val | Ser | His | Ala | Arg | Pro | Arg | Trp | Ile | Trp | Phe | Cys | Leu | |
| | | | | 2985 | | | | | 2990 | | | | | 2995 | | |
| CTC | CTG | CTT | GCT | GCA | GGG | GTA | GGC | ATC | TAC | CTC | CTC | CCC | AAC | CGA | | 9374 |
| Leu | Leu | Leu | Ala | Ala | Gly | Val | Gly | Ile | Tyr | Leu | Leu | Pro | Asn | Arg | | |
| | | | 3000 | | | | | 3005 | | | | | 3010 | | | |
| TGAAGGTTGG GGTAAACACT CCGGCCT | | | | | | | | | | | | | | | | 9401 |

(2) INFORMATION FOR SEQ ID NO:10:

(i) SEQUENCE CHARACTERISTICS:
      (A) LENGTH: 3011 amino acids
      (B) TYPE: amino acid
      (D) TOPOLOGY: linear (ii) MOLECULE TYPE: protein (xi) SEQUENCE DESCRIPTION: SEQ ID NO:10:

```
Met Ser Thr Asn Pro Lys Pro Gln Lys Lys Asn Lys Arg Asn Thr Asn
 1           5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140
```

-continued

| | | | | | | | | | | | | | | | |
|---|---|---|---|---|---|---|---|---|---|---|---|---|---|---|---|
| Gly | Gly | Ala | Ala | Arg | Ala | Leu | Ala | His | Gly | Val | Arg | Val | Leu | Glu | Asp |
| 145 | | | | 150 | | | | 155 | | | | | | | 160 |
| Gly | Val | Asn | Tyr | Ala | Thr | Gly | Asn | Leu | Pro | Gly | Cys | Ser | Phe | Ser | Ile |
| | | | | 165 | | | | 170 | | | | | 175 | | |
| Phe | Leu | Leu | Ala | Leu | Leu | Ser | Cys | Leu | Thr | Val | Pro | Ala | Ser | Ala | Tyr |
| | | | 180 | | | | | 185 | | | | | 190 | | |
| Gln | Val | Arg | Asn | Ser | Thr | Gly | Leu | Tyr | His | Val | Thr | Asn | Asp | Cys | Pro |
| | | | 195 | | | | | 200 | | | | 205 | | | |
| Asn | Ser | Ser | Ile | Val | Tyr | Glu | Ala | Ala | Asp | Ala | Ile | Leu | His | Thr | Pro |
| | | 210 | | | | 215 | | | | | 220 | | | | |
| Gly | Cys | Val | Pro | Cys | Val | Arg | Glu | Gly | Asn | Ala | Ser | Arg | Cys | Trp | Val |
| 225 | | | | | 230 | | | | | 235 | | | | | 240 |
| Ala | Met | Thr | Pro | Thr | Val | Ala | Thr | Arg | Asp | Gly | Lys | Leu | Pro | Ala | Thr |
| | | | | 245 | | | | | 250 | | | | | 255 | |
| Gln | Leu | Arg | Arg | His | Ile | Asp | Leu | Leu | Val | Gly | Ser | Ala | Thr | Leu | Cys |
| | | | 260 | | | | | 265 | | | | | 270 | | |
| Ser | Ala | Leu | Tyr | Val | Gly | Asp | Leu | Cys | Gly | Ser | Val | Phe | Leu | Val | Gly |
| | | 275 | | | | 280 | | | | | 285 | | | | |
| Gln | Leu | Phe | Thr | Phe | Ser | Pro | Arg | Arg | His | Trp | Thr | Thr | Gln | Gly | Cys |
| | 290 | | | | | 295 | | | | | 300 | | | | |
| Asn | Cys | Ser | Ile | Tyr | Pro | Gly | His | Ile | Thr | Gly | His | Arg | Met | Ala | Trp |
| 305 | | | | | 310 | | | | | 315 | | | | | 320 |
| Asp | Met | Met | Met | Asn | Trp | Ser | Pro | Thr | Thr | Ala | Leu | Val | Met | Ala | Gln |
| | | | | 325 | | | | | 330 | | | | | 335 | |
| Leu | Leu | Arg | Ile | Pro | Gln | Ala | Ile | Leu | Asp | Met | Ile | Ala | Gly | Ala | His |
| | | | 340 | | | | | 345 | | | | | 350 | | |
| Trp | Gly | Val | Leu | Ala | Gly | Ile | Ala | Tyr | Phe | Ser | Met | Val | Gly | Asn | Trp |
| | | 355 | | | | 360 | | | | | 365 | | | | |
| Ala | Lys | Val | Leu | Val | Val | Leu | Leu | Leu | Phe | Ala | Gly | Val | Asp | Ala | Glu |
| | 370 | | | | | 375 | | | | | 380 | | | | |
| Thr | His | Val | Thr | Gly | Gly | Ser | Ala | Gly | His | Thr | Val | Ser | Gly | Phe | Val |
| 385 | | | | | 390 | | | | | 395 | | | | | 400 |
| Ser | Leu | Leu | Ala | Pro | Gly | Ala | Lys | Gln | Asn | Val | Gln | Leu | Ile | Asn | Thr |
| | | | | 405 | | | | | 410 | | | | | 415 | |
| Asn | Gly | Ser | Trp | His | Leu | Asn | Ser | Thr | Ala | Leu | Asn | Cys | Asn | Asp | Ser |
| | | | 420 | | | | | 425 | | | | | 430 | | |
| Leu | Asn | Thr | Gly | Trp | Leu | Ala | Gly | Leu | Phe | Tyr | His | His | Lys | Phe | Asn |
| | | | 435 | | | | | 440 | | | | | 445 | | |
| Ser | Ser | Gly | Cys | Pro | Glu | Arg | Leu | Ala | Ser | Cys | Arg | Pro | Leu | Thr | Asp |
| | | 450 | | | | 455 | | | | | 460 | | | | |
| Phe | Asp | Gln | Gly | Trp | Gly | Pro | Ile | Ser | Tyr | Ala | Asn | Gly | Ser | Gly | Pro |
| 465 | | | | | 470 | | | | | 475 | | | | | 480 |
| Asp | Gln | Arg | Pro | Tyr | Cys | Trp | His | Tyr | Pro | Pro | Lys | Pro | Cys | Gly | Ile |
| | | | | 485 | | | | | 490 | | | | | 495 | |
| Val | Pro | Ala | Lys | Ser | Val | Cys | Gly | Pro | Val | Tyr | Cys | Phe | Thr | Pro | Ser |
| | | | 500 | | | | | 505 | | | | | 510 | | |
| Pro | Val | Val | Val | Gly | Thr | Thr | Asp | Arg | Ser | Gly | Ala | Pro | Thr | Tyr | Ser |
| | | | 515 | | | | | 520 | | | | | 525 | | |
| Trp | Gly | Glu | Asn | Asp | Thr | Asp | Val | Phe | Val | Leu | Asn | Asn | Thr | Arg | Pro |
| | 530 | | | | | 535 | | | | | 540 | | | | |
| Pro | Leu | Gly | Asn | Trp | Phe | Gly | Cys | Thr | Trp | Met | Asn | Ser | Thr | Gly | Phe |
| 545 | | | | | 550 | | | | | 555 | | | | | 560 |
| Thr | Lys | Val | Cys | Gly | Ala | Pro | Pro | Cys | Val | Ile | Gly | Gly | Ala | Gly | Asn |

-continued

|     |     |     |     | 565 |     |     |     | 570 |     |     |     | 575 |     |     |
|-----|-----|-----|-----|-----|-----|-----|-----|-----|-----|-----|-----|-----|-----|-----|
| Asn | Thr | Leu | His<br>580 | Cys | Pro | Thr | Asp | Cys<br>585 | Phe | Arg | Lys | His | Pro<br>590 | Asp | Ala |
| Thr | Tyr | Ser | Arg<br>595 | Cys | Gly | Ser | Gly<br>600 | Pro | Trp | Ile | Thr | Pro<br>605 | Arg | Cys | Leu |
| Val | Asp<br>610 | Tyr | Pro | Tyr | Arg | Leu<br>615 | Trp | His | Tyr | Pro | Cys<br>620 | Thr | Ile | Asn | Tyr |
| Thr<br>625 | Ile | Phe | Lys | Ile | Arg<br>630 | Met | Tyr | Val | Gly | Gly<br>635 | Val | Glu | His | Arg | Leu<br>640 |
| Glu | Ala | Ala | Cys | Asn<br>645 | Trp | Thr | Arg | Gly | Glu<br>650 | Arg | Cys | Asp | Leu | Glu<br>655 | Asp |
| Arg | Asp | Arg | Ser<br>660 | Glu | Leu | Ser | Pro<br>665 | Leu | Leu | Thr | Thr | Thr<br>670 | Gln | Trp |
| Gln | Val | Leu<br>675 | Pro | Cys | Ser | Phe | Thr<br>680 | Thr | Leu | Pro | Ala | Leu<br>685 | Ser | Thr | Gly |
| Leu | Ile<br>690 | His | Leu | His | Gln | Asn<br>695 | Ile | Val | Asp | Val | Gln<br>700 | Tyr | Leu | Tyr | Gly |
| Val<br>705 | Gly | Ser | Ser | Ile | Ala<br>710 | Ser | Trp | Ala | Ile | Lys<br>715 | Trp | Glu | Tyr | Val<br>720 | Val |
| Leu | Leu | Phe | Leu | Leu<br>725 | Leu | Ala | Asp | Ala | Arg<br>730 | Val | Cys | Ser | Cys | Leu<br>735 | Trp |
| Met | Met | Leu | Leu<br>740 | Ile | Ser | Gln | Ala | Glu<br>745 | Ala | Ala | Leu | Glu | Asn<br>750 | Leu | Val |
| Ile | Leu | Asn<br>755 | Ala | Ala | Ser | Leu | Ala<br>760 | Gly | Thr | His | Gly | Leu<br>765 | Val | Ser | Phe |
| Leu | Val<br>770 | Phe | Phe | Cys | Phe | Ala<br>775 | Trp | Tyr | Leu | Lys | Gly<br>780 | Lys | Trp | Val | Pro |
| Gly<br>785 | Ala | Val | Tyr | Thr | Phe<br>790 | Tyr | Gly | Met | Trp | Pro<br>795 | Leu | Leu | Leu | Leu<br>800 |
| Leu | Ala | Leu | Pro | Gln<br>805 | Arg | Ala | Tyr | Ala | Leu<br>810 | Asp | Thr | Glu | Val | Ala<br>815 | Ala |
| Ser | Cys | Gly | Gly<br>820 | Val | Val | Leu | Val | Gly<br>825 | Leu | Met | Ala | Leu | Thr<br>830 | Leu | Ser |
| Pro | Tyr | Tyr | Lys<br>835 | Arg | Tyr | Ile | Ser | Trp<br>840 | Cys | Leu | Trp | Trp | Leu<br>845 | Gln | Tyr |
| Phe | Leu<br>850 | Thr | Arg | Val | Glu | Ala<br>855 | Gln | Leu | His | Val | Trp<br>860 | Ile | Pro | Pro | Leu |
| Asn<br>865 | Val | Arg | Gly | Gly | Arg<br>870 | Asp | Ala | Val | Ile | Leu<br>875 | Leu | Met | Cys | Ala | Val<br>880 |
| His | Pro | Thr | Leu | Val<br>885 | Phe | Asp | Ile | Thr | Lys<br>890 | Leu | Leu | Leu | Ala | Val<br>895 | Phe |
| Gly | Pro | Leu | Trp<br>900 | Ile | Leu | Gln | Ala | Ser<br>905 | Leu | Leu | Lys | Val | Pro<br>910 | Tyr | Phe |
| Val | Arg | Val<br>915 | Gln | Gly | Leu | Leu | Arg<br>920 | Phe | Cys | Ala | Leu | Ala<br>925 | Arg | Lys | Met |
| Ile | Gly | Gly<br>930 | His | Tyr | Val | Gln | Met<br>935 | Val | Ile | Ile | Lys | Leu<br>940 | Gly | Ala | Leu |
| Thr<br>945 | Gly | Thr | Tyr | Val | Tyr<br>950 | Asn | His | Leu | Thr | Pro<br>955 | Leu | Arg | Asp | Trp | Ala<br>960 |
| His | Asn | Gly | Leu | Arg<br>965 | Asp | Leu | Ala | Val | Ala<br>970 | Val | Glu | Pro | Val | Val<br>975 | Phe |
| Ser | Gln | Met | Glu<br>980 | Thr | Lys | Leu | Ile | Thr<br>985 | Trp | Gly | Ala | Asp | Thr<br>990 | Ala | Ala |

```
Cys Gly Asp Ile Ile Asn Gly Leu Pro Val Ser Ala Arg Arg Gly Arg
        995                 1000                1005
Glu Ile Leu Leu Gly Pro Ala Asp Gly Met Val Ser Lys Gly Trp Arg
    1010                1015                1020
Leu Leu Ala Pro Ile Thr Ala Tyr Ala Gln Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Ile Val Ser Thr Ala Ala Gln Thr Phe Leu Ala Thr
            1060                1065                1070
Cys Ile Asn Gly Val Cys Trp Thr Val Tyr His Gly Ala Gly Thr Arg
        1075                1080                1085
Thr Ile Ala Ser Pro Lys Gly Pro Val Ile Gln Met Tyr Thr Asn Val
    1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
                1125                1130                1135
Ala Asp Val Ile Pro Val Arg Arg Arg Gly Asp Ser Arg Gly Ser Leu
            1140                1145                1150
Leu Ser Pro Arg Pro Ile Ser Tyr Leu Lys Gly Ser Ser Gly Gly Pro
        1155                1160                1165
Leu Leu Cys Pro Ala Gly His Ala Val Gly Ile Phe Arg Ala Ala Val
    1170                1175                1180
Cys Thr Arg Gly Val Ala Lys Ala Val Asp Phe Ile Pro Val Glu Asn
1185                1190                1195                1200
Leu Glu Thr Thr Met Arg Ser Pro Val Phe Thr Asp Asn Ser Ser Pro
                1205                1210                1215
Pro Val Val Pro Gln Ser Phe Gln Val Ala His Leu His Ala Pro Thr
            1220                1225                1230
Gly Ser Gly Lys Ser Thr Lys Val Pro Ala Ala Tyr Ala Ala Gln Gly
        1235                1240                1245
Tyr Lys Val Leu Val Leu Asn Pro Ser Val Ala Ala Thr Leu Gly Phe
    1250                1255                1260
Gly Ala Tyr Met Ser Lys Ala His Gly Ile Asp Pro Asn Ile Arg Thr
1265                1270                1275                1280
Gly Val Arg Thr Ile Thr Thr Gly Ser Pro Ile Thr Tyr Ser Thr Tyr
                1285                1290                1295
Gly Lys Phe Leu Ala Asp Gly Gly Cys Ser Gly Gly Ala Tyr Asp Ile
            1300                1305                1310
Ile Ile Cys Asp Glu Cys His Ser Thr Asp Ala Thr Ser Ile Leu Gly
        1315                1320                1325
Ile Gly Thr Val Leu Asp Gln Ala Glu Thr Ala Gly Ala Arg Leu Val
    1330                1335                1340
Val Leu Ala Thr Ala Thr Pro Pro Gly Ser Val Thr Val Pro His Pro
1345                1350                1355                1360
Asn Ile Glu Glu Val Ala Leu Ser Thr Thr Gly Glu Ile Pro Phe Tyr
                1365                1370                1375
Gly Lys Ala Ile Pro Leu Glu Val Ile Lys Gly Gly Arg His Leu Ile
            1380                1385                1390
Phe Cys His Ser Lys Lys Lys Cys Asp Glu Leu Ala Ala Lys Leu Val
        1395                1400                1405
Ala Leu Gly Ile Asn Ala Val Ala Tyr Tyr Arg Gly Leu Asp Val Ser
    1410                1415                1420
```

```
Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Cys Asn Thr
                    1445                1450                1455

Cys Val Thr Gln Thr Val Asp Phe Ser Leu Asp Pro Thr Phe Thr Ile
                1460                1465                1470

Glu Thr Ile Thr Leu Pro Gln Asp Ala Val Ser Arg Thr Gln Arg Arg
            1475                1480                1485

Gly Arg Thr Gly Arg Gly Lys Pro Gly Ile Tyr Arg Phe Val Ala Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
                1525                1530                1535

Val Arg Leu Arg Ala Tyr Met Asn Thr Pro Gly Leu Pro Val Cys Gln
                1540                1545                1550

Asp His Leu Glu Phe Trp Glu Gly Val Phe Thr Gly Leu Thr His Ile
                1555                1560                1565

Asp Ala His Phe Leu Ser Gln Thr Lys Gln Ser Gly Glu Asn Leu Pro
                1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
                1620                1625                1630

Asn Glu Ile Thr Leu Thr His Pro Val Thr Lys Tyr Ile Met Thr Cys
                1635                1640                1645

Met Ser Ala Asp Leu Glu Val Val Thr Ser Thr Trp Val Leu Val Gly
1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
                1685                1690                1695

Asp Arg Glu Val Leu Tyr Arg Glu Phe Asp Glu Met Glu Glu Cys Ser
                1700                1705                1710

Gln His Leu Pro Tyr Ile Glu Gln Gly Met Met Leu Ala Glu Gln Phe
                1715                1720                1725

Lys Gln Lys Ala Leu Gly Leu Leu Gln Thr Ala Ser Arg Gln Ala Glu
                1730                1735                1740

Val Ile Ala Pro Ala Val Gln Thr Asn Trp Gln Lys Leu Glu Thr Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
                1780                1785                1790

Phe Thr Ala Ala Val Thr Ser Pro Leu Thr Thr Ser Gln Thr Leu Leu
                1795                1800                1805

Phe Asn Ile Leu Gly Gly Trp Val Ala Ala Gln Leu Ala Ala Pro Gly
                1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Ile Asp Ile Leu Ala Gly Tyr Gly
```

-continued

```
                    1845                          1850                         1855
Ala  Gly  Val  Ala  Gly  Ala  Leu  Val  Ala  Phe  Lys  Ile  Met  Ser  Gly  Glu
                         1860                         1865                    1870
Val  Pro  Ser  Thr  Glu  Asp  Leu  Val  Asn  Leu  Leu  Pro  Ala  Ile  Leu  Ser
               1875                         1880                    1885
Pro  Gly  Ala  Leu  Val  Val  Gly  Val  Val  Cys  Ala  Ala  Ile  Leu  Arg  Arg
               1890                    1895                    1900
His  Val  Gly  Pro  Gly  Glu  Gly  Ala  Val  Gln  Trp  Met  Asn  Arg  Leu  Ile
1905                     1910                    1915                         1920
Ala  Phe  Ala  Ser  Arg  Gly  Asn  His  Val  Ser  Pro  Thr  His  Tyr  Val  Pro
                    1925                    1930                    1935
Glu  Ser  Asp  Ala  Ala  Ala  Arg  Val  Thr  Ala  Ile  Leu  Ser  Ser  Leu  Thr
                    1940                    1945                    1950
Val  Thr  Gln  Leu  Leu  Arg  Arg  Leu  His  Gln  Trp  Ile  Ser  Ser  Glu  Cys
                    1955                    1960                    1965
Thr  Thr  Pro  Cys  Ser  Gly  Ser  Trp  Leu  Arg  Asp  Ile  Trp  Asp  Trp  Ile
                    1970                    1975                    1980
Cys  Glu  Val  Leu  Ser  Asp  Phe  Lys  Thr  Trp  Leu  Lys  Ala  Lys  Leu  Met
1985                    1990                    1995                         2000
Pro  Gln  Leu  Pro  Gly  Ile  Pro  Phe  Val  Ser  Cys  Gln  Arg  Gly  Tyr  Lys
                         2005                    2010                    2015
Gly  Val  Trp  Arg  Val  Asp  Gly  Ile  Met  His  Thr  Arg  Cys  His  Cys  Gly
                    2020                    2025                    2030
Ala  Glu  Ile  Thr  Gly  His  Val  Lys  Asn  Gly  Thr  Met  Arg  Ile  Val  Gly
                    2035                    2040                    2045
Pro  Arg  Thr  Cys  Arg  Asn  Met  Trp  Ser  Gly  Thr  Phe  Pro  Ile  Asn  Ala
                    2050                    2055                    2060
Tyr  Thr  Thr  Gly  Pro  Cys  Thr  Pro  Leu  Pro  Ala  Pro  Asn  Tyr  Thr  Phe
2065                    2070                    2075                         2080
Ala  Leu  Trp  Arg  Val  Ser  Ala  Glu  Glu  Tyr  Val  Glu  Ile  Arg  Gln  Val
                         2085                    2090                    2095
Gly  Asp  Phe  His  Tyr  Val  Thr  Gly  Met  Thr  Thr  Asp  Asn  Leu  Lys  Cys
                    2100                    2105                    2110
Pro  Cys  Gln  Val  Pro  Ser  Pro  Glu  Phe  Phe  Thr  Glu  Leu  Asp  Gly  Val
                    2115                    2120                    2125
Arg  Leu  His  Arg  Phe  Ala  Pro  Pro  Cys  Lys  Pro  Leu  Leu  Arg  Glu  Glu
                    2130                    2135                    2140
Val  Ser  Phe  Arg  Val  Gly  Leu  His  Glu  Tyr  Pro  Val  Gly  Ser  Gln  Leu
2145                    2150                    2155                         2160
Pro  Cys  Glu  Pro  Glu  Pro  Asp  Val  Ala  Val  Leu  Thr  Ser  Met  Leu  Thr
                    2165                    2170                    2175
Asp  Pro  Ser  His  Ile  Thr  Ala  Glu  Ala  Ala  Gly  Arg  Arg  Leu  Ala  Arg
                    2180                    2185                    2190
Gly  Ser  Pro  Pro  Ser  Val  Ala  Ser  Ser  Ser  Ala  Ser  Gln  Leu  Ser  Ala
                    2195                    2200                    2205
Pro  Ser  Leu  Lys  Ala  Thr  Cys  Thr  Ala  Asn  His  Asp  Ser  Pro  Asp  Ala
                    2210                    2215                    2220
Glu  Leu  Ile  Glu  Ala  Asn  Leu  Leu  Trp  Arg  Gln  Glu  Met  Gly  Gly  Asn
2225                    2230                    2235                         2240
Ile  Thr  Arg  Val  Glu  Ser  Glu  Asn  Lys  Val  Val  Ile  Leu  Asp  Ser  Phe
                    2245                    2250                    2255
Asp  Pro  Leu  Val  Ala  Glu  Glu  Asp  Glu  Arg  Glu  Ile  Ser  Val  Pro  Ala
                    2260                    2265                    2270
```

```
Glu Ile Leu Arg Lys Ser Arg Arg Phe Ala Gln Ala Leu Pro Val Trp
    2275            2280                2285
Ala Arg Pro Asp Tyr Asn Pro Leu Val Glu Thr Trp Lys Lys Pro
    2290            2295                2300
Asp Tyr Glu Pro Pro Val Val His Gly Cys Pro Leu Pro Pro Lys
2305            2310            2315                2320
Ser Pro Pro Val Pro Pro Pro Arg Lys Lys Arg Thr Val Val Leu Thr
            2325            2330            2335
Glu Ser Thr Leu Ser Thr Ala Leu Ala Glu Leu Ala Thr Arg Ser Phe
            2340            2345            2350
Gly Ser Ser Ser Thr Ser Gly Ile Thr Gly Asp Asn Thr Thr Thr Ser
        2355            2360            2365
Ser Glu Pro Ala Pro Ser Gly Cys Pro Pro Asp Ser Asp Ala Glu Ser
    2370            2375            2380
Tyr Ser Ser Met Pro Pro Leu Glu Gly Glu Pro Gly Asp Pro Asp Leu
2385            2390            2395                2400
Ser Asp Gly Ser Trp Ser Thr Val Ser Ser Glu Ala Asn Ala Glu Asp
            2405            2410            2415
Val Val Cys Cys Ser Met Ser Tyr Ser Trp Thr Gly Ala Leu Val Thr
            2420            2425            2430
Pro Cys Ala Ala Glu Glu Gln Lys Leu Pro Ile Asn Ala Leu Ser Asn
        2435            2440            2445
Ser Leu Leu Arg His His Asn Leu Val Tyr Ser Thr Thr Ser Arg Ser
    2450            2455            2460
Ala Cys Gln Arg Gln Lys Lys Val Thr Phe Asp Arg Leu Gln Val Leu
2465            2470            2475                2480
Asp Ser His Tyr Gln Asp Val Leu Lys Glu Val Lys Ala Ala Ala Ser
            2485            2490            2495
Lys Val Lys Ala Asn Leu Leu Ser Val Glu Glu Ala Cys Ser Leu Thr
            2500            2505            2510
Pro Pro His Ser Ala Lys Ser Lys Phe Gly Tyr Gly Ala Lys Asp Val
        2515            2520            2525
Arg Cys His Ala Arg Lys Ala Val Thr His Ile Asn Ser Val Trp Lys
    2530            2535            2540
Asp Leu Leu Glu Asp Asn Val Thr Pro Ile Asp Thr Thr Ile Met Ala
2545            2550            2555                2560
Lys Asn Glu Val Phe Cys Val Gln Pro Glu Lys Gly Gly Arg Lys Pro
            2565            2570            2575
Ala Arg Leu Ile Val Phe Pro Asp Leu Gly Val Arg Val Cys Glu Lys
        2580            2585            2590
Met Ala Leu Tyr Asp Val Val Thr Lys Leu Pro Leu Ala Val Met Gly
        2595            2600            2605
Ser Ser Tyr Gly Phe Gln Tyr Ser Pro Gly Gln Arg Val Glu Phe Leu
    2610            2615            2620
Val Gln Ala Trp Lys Ser Lys Lys Thr Pro Met Gly Phe Ser Tyr Asp
2625            2630            2635                2640
Thr Arg Cys Phe Asp Ser Thr Val Thr Glu Ser Asp Ile Arg Thr Glu
            2645            2650            2655
Glu Ala Ile Tyr Gln Cys Cys Asp Leu Asp Pro Gln Ala Arg Val Ala
            2660            2665            2670
Ile Lys Ser Leu Thr Glu Arg Leu Tyr Val Gly Gly Pro Leu Thr Asn
        2675            2680            2685
Ser Arg Gly Glu Asn Cys Gly Tyr Arg Arg Cys Arg Ala Ser Gly Val
    2690            2695            2700
```

```
Leu  Thr  Thr  Ser  Cys  Gly  Asn  Thr  Leu  Thr  Cys  Tyr  Ile  Lys  Ala  Arg
2705                2710                2715                2720

Ala  Ala  Cys  Arg  Ala  Ala  Gly  Leu  Gln  Asp  Cys  Thr  Met  Leu  Val  Cys
               2725                2730                2735

Gly  Asp  Asp  Leu  Val  Val  Ile  Cys  Glu  Ser  Ala  Gly  Val  Gln  Glu  Asp
          2740                2745                2750

Ala  Ala  Ser  Leu  Arg  Ala  Phe  Thr  Glu  Ala  Met  Thr  Arg  Tyr  Ser  Ala
     2755                2760                2765

Pro  Pro  Gly  Asp  Pro  Pro  Gln  Pro  Glu  Tyr  Asp  Leu  Glu  Leu  Ile  Thr
2770                2775                2780

Ser  Cys  Ser  Ser  Asn  Val  Ser  Val  Ala  His  Asp  Gly  Ala  Gly  Lys  Arg
2785                2790                2795                2800

Val  Tyr  Tyr  Leu  Thr  Arg  Asp  Pro  Thr  Thr  Pro  Leu  Ala  Arg  Ala  Ala
               2805                2810                2815

Trp  Glu  Thr  Ala  Arg  His  Thr  Pro  Val  Asn  Ser  Trp  Leu  Gly  Asn  Ile
          2820                2825                2830

Ile  Met  Phe  Ala  Pro  Thr  Leu  Trp  Ala  Arg  Met  Ile  Leu  Met  Thr  His
     2835                2840                2845

Phe  Phe  Ser  Val  Leu  Ile  Ala  Arg  Asp  Gln  Leu  Glu  Gln  Ala  Leu  Asp
2850                2855                2860

Cys  Glu  Ile  Tyr  Gly  Ala  Cys  Tyr  Ser  Ile  Glu  Pro  Leu  Asp  Leu  Pro
2865                2870                2875                2880

Pro  Ile  Ile  Gln  Arg  Leu  His  Gly  Leu  Ser  Ala  Phe  Ser  Leu  His  Ser
               2885                2890                2895

Tyr  Ser  Pro  Gly  Glu  Ile  Asn  Arg  Val  Ala  Ala  Cys  Leu  Arg  Lys  Leu
          2900                2905                2910

Gly  Val  Pro  Pro  Leu  Arg  Ala  Trp  Arg  His  Arg  Ala  Arg  Ser  Val  Arg
     2915                2920                2925

Ala  Arg  Leu  Leu  Ala  Arg  Gly  Gly  Arg  Ala  Ala  Ile  Cys  Gly  Lys  Tyr
2930                2935                2940

Leu  Phe  Asn  Trp  Ala  Val  Arg  Thr  Lys  Leu  Lys  Leu  Thr  Pro  Ile  Ala
2945                2950                2955                2960

Ala  Ala  Gly  Gln  Leu  Asp  Leu  Ser  Gly  Trp  Phe  Thr  Ala  Gly  Tyr  Ser
               2965                2970                2975

Gly  Gly  Asp  Ile  Tyr  His  Ser  Val  Ser  His  Ala  Arg  Pro  Arg  Trp  Ile
          2980                2985                2990

Trp  Phe  Cys  Leu  Leu  Leu  Leu  Ala  Ala  Gly  Val  Gly  Ile  Tyr  Leu  Leu
     2995                3000                3005

Pro  Asn  Arg
3010
```

( 2 ) INFORMATION FOR SEQ ID NO:11:

( i ) SEQUENCE CHARACTERISTICS:
        ( A ) LENGTH: 3075 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..3063

( x i ) SEQUENCE DESCRIPTION: SEQ ID NO:11:

```
ATG  GCT  ACA  AAG  GCT  GTT  TGT  GTT  TTG  AAG  GGT  GAC  GGC  CCA  GTT  CAA    48
Met  Ala  Thr  Lys  Ala  Val  Cys  Val  Leu  Lys  Gly  Asp  Gly  Pro  Val  Gln
```

|  |  |  |  |  |  |  |  |  |  |  |  |  |  |  |  |
|---|---|---|---|---|---|---|---|---|---|---|---|---|---|---|---|
| 1 |  |  |  | 5 |  |  |  |  |  | 10 |  |  |  |  | 15 |

```
GGT  ATT  ATT  AAC  TTC  GAG  CAG  AAG  GAA  AGT  AAT  GGA  CCA  GTG  AAG  GTG         96
Gly  Ile  Ile  Asn  Phe  Glu  Gln  Lys  Glu  Ser  Asn  Gly  Pro  Val  Lys  Val
               20                  25                  30

TGG  GGA  AGC  ATT  AAA  GGA  CTG  ACT  GAA  GGC  CTG  CAT  GGA  TTC  CAT  GTT        144
Trp  Gly  Ser  Ile  Lys  Gly  Leu  Thr  Glu  Gly  Leu  His  Gly  Phe  His  Val
          35                  40                  45

CAT  GAG  TTT  GGA  GAT  AAT  ACA  GCA  GGC  TGT  ACC  AGT  GCA  GGT  CCT  CAC        192
His  Glu  Phe  Gly  Asp  Asn  Thr  Ala  Gly  Cys  Thr  Ser  Ala  Gly  Pro  His
     50                  55                  60

TTT  AAT  CCT  CTA  TCC  AGA  AAA  CAC  GGT  GGG  CCA  AAG  GAT  GAA  GAG  AGG        240
Phe  Asn  Pro  Leu  Ser  Arg  Lys  His  Gly  Gly  Pro  Lys  Asp  Glu  Glu  Arg
65                  70                  75                              80

CAT  GTT  GGA  GAC  TTG  GGC  AAT  GTG  ACT  GCT  GAC  AAA  GAT  GGT  GTG  GCC        288
His  Val  Gly  Asp  Leu  Gly  Asn  Val  Thr  Ala  Asp  Lys  Asp  Gly  Val  Ala
                    85                  90                  95

GAT  GTG  TCT  ATT  GAA  GAT  TCT  GTG  ATC  TCA  CTC  TCA  GGA  GAC  CAT  TGC        336
Asp  Val  Ser  Ile  Glu  Asp  Ser  Val  Ile  Ser  Leu  Ser  Gly  Asp  His  Cys
                    100                 105                 110

ATC  ATT  GGC  CGC  ACA  CTG  GTG  GTC  CAT  GAA  AAA  GCA  GAT  GAC  TTG  GGC        384
Ile  Ile  Gly  Arg  Thr  Leu  Val  Val  His  Glu  Lys  Ala  Asp  Asp  Leu  Gly
               115                 120                 125

AAA  GGT  GGA  AAT  GAA  GAA  AGT  ACA  AAG  ACA  GGA  AAC  GCT  GGA  AGT  CGT        432
Lys  Gly  Gly  Asn  Glu  Glu  Ser  Thr  Lys  Thr  Gly  Asn  Ala  Gly  Ser  Arg
130                 135                 140

TTG  GCT  TGT  GGT  GTA  ATT  GGG  ATC  GCC  CAG  AAT  TTG  GAA  TTC  GGG  GCG        480
Leu  Ala  Cys  Gly  Val  Ile  Gly  Ile  Ala  Gln  Asn  Leu  Glu  Phe  Gly  Ala
145                 150                 155                 160

GTG  GAC  TTT  ATC  CCT  GTG  GAG  AAC  CTA  GAG  ACA  ACC  ATG  AGG  TCC  CCG        528
Val  Asp  Phe  Ile  Pro  Val  Glu  Asn  Leu  Glu  Thr  Thr  Met  Arg  Ser  Pro
                    165                 170                 175

GTG  TTC  ACG  GAT  AAC  TCC  TCT  CCA  CCA  GTA  GTG  CCC  CAG  AGC  TTC  CAG        576
Val  Phe  Thr  Asp  Asn  Ser  Ser  Pro  Pro  Val  Val  Pro  Gln  Ser  Phe  Gln
               180                 185                 190

GTG  GCT  CAC  CTC  CAT  GCT  CCC  ACA  GGC  AGC  GGC  AAA  AGC  ACC  AAG  GTC        624
Val  Ala  His  Leu  His  Ala  Pro  Thr  Gly  Ser  Gly  Lys  Ser  Thr  Lys  Val
          195                 200                 205

CCG  GCT  GCA  TAT  GCA  GCT  CAG  GGC  TAT  AAG  GTG  CTA  GTA  CTC  AAC  CCC        672
Pro  Ala  Ala  Tyr  Ala  Ala  Gln  Gly  Tyr  Lys  Val  Leu  Val  Leu  Asn  Pro
210                 215                 220

TCT  GTT  GCT  GCA  ACA  CTG  GGC  TTT  GGT  GCT  TAC  ATG  TCC  AAG  GCT  CAT        720
Ser  Val  Ala  Ala  Thr  Leu  Gly  Phe  Gly  Ala  Tyr  Met  Ser  Lys  Ala  His
225                 230                 235                 240

GGG  ATC  GAT  CCT  AAC  ATC  AGG  ACC  GGG  GTG  AGA  ACA  ATT  ACC  ACT  GGC        768
Gly  Ile  Asp  Pro  Asn  Ile  Arg  Thr  Gly  Val  Arg  Thr  Ile  Thr  Thr  Gly
                    245                 250                 255

AGC  CCC  ATC  ACG  TAC  TCC  ACC  TAC  GGC  AAG  TTC  CTT  GCC  GAC  GGC  GGG        816
Ser  Pro  Ile  Thr  Tyr  Ser  Thr  Tyr  Gly  Lys  Phe  Leu  Ala  Asp  Gly  Gly
               260                 265                 270

TGC  TCG  GGG  GGC  GCT  TAT  GAC  ATA  ATA  ATT  TGT  GAC  GAG  TGC  CAC  TCC        864
Cys  Ser  Gly  Gly  Ala  Tyr  Asp  Ile  Ile  Ile  Cys  Asp  Glu  Cys  His  Ser
          275                 280                 285

ACG  GAT  GCC  ACA  TCC  ATC  TTG  GGC  ATC  GGC  ACT  GTC  CTT  GAC  CAA  GCA        912
Thr  Asp  Ala  Thr  Ser  Ile  Leu  Gly  Ile  Gly  Thr  Val  Leu  Asp  Gln  Ala
     290                 295                 300

GAG  ACT  GCG  GGG  GCG  AGA  CTG  GTT  GTG  CTC  GCC  ACC  GCC  ACC  CCT  CCG        960
Glu  Thr  Ala  Gly  Ala  Arg  Leu  Val  Val  Leu  Ala  Thr  Ala  Thr  Pro  Pro
305                 310                 315                 320

GGC  TCC  GTC  ACT  GTG  CCC  CAT  CCC  AAC  ATC  GAG  GAG  GTT  GCT  CTG  TCC       1008
Gly  Ser  Val  Thr  Val  Pro  His  Pro  Asn  Ile  Glu  Glu  Val  Ala  Leu  Ser
```

-continued

| | | | | | | | | | | | | | | | | |
|---|---|---|---|---|---|---|---|---|---|---|---|---|---|---|---|---|
| | | | | 325 | | | | | 330 | | | | | 335 | | |
| ACC | ACC | GGA | GAG | ATC | CCT | TTT | TAC | GGC | AAG | GCT | ATC | CCC | CTC | GAA | GTA | 1056 |
| Thr | Thr | Gly | Glu 340 | Ile | Pro | Phe | Tyr | Gly | Lys 345 | Ala | Ile | Pro | Leu 350 | Glu | Val | |
| ATC | AAG | GGG | GGG | AGA | CAT | CTC | ATC | TTC | TGT | CAT | TCA | AAG | AAG | AAG | TGC | 1104 |
| Ile | Lys | Gly | Gly 355 | Arg | His | Leu | Ile | Phe 360 | Cys | His | Ser | Lys | Lys 365 | Lys | Cys | |
| GAC | GAA | CTC | GCC | GCA | AAG | CTG | GTC | GCA | TTG | GGC | ATC | AAT | GCC | GTG | GCC | 1152 |
| Asp | Glu 370 | Leu | Ala | Ala | Lys | Leu 375 | Val | Ala | Leu | Gly | Ile 380 | Asn | Ala | Val | Ala | |
| TAC | TAC | CGC | GGT | CTT | GAC | GTG | TCC | GTC | ATC | CCG | ACC | AGC | GGC | GAT | GTT | 1200 |
| Tyr 385 | Tyr | Arg | Gly | Leu | Asp 390 | Val | Ser | Val | Ile | Pro 395 | Thr | Ser | Gly | Asp | Val 400 | |
| GTC | GTC | GTG | GCA | ACC | GAT | GCC | CTC | ATG | ACC | GGC | TAT | ACC | GGC | GAC | TTC | 1248 |
| Val | Val | Val | Ala | Thr 405 | Asp | Ala | Leu | Met | Thr 410 | Gly | Tyr | Thr | Gly | Asp 415 | Phe | |
| GAC | TCG | GTG | ATA | GAC | TGC | AAT | ACG | TGT | GTC | ACC | CAG | ACA | GTC | GAT | TTC | 1296 |
| Asp | Ser | Val | Ile 420 | Asp | Cys | Asn | Thr | Cys 425 | Val | Thr | Gln | Thr | Val 430 | Asp | Phe | |
| AGC | CTT | GAC | CCT | ACC | TTC | ACC | ATT | GAG | ACA | ATC | ACG | CTC | CCC | CAG | GAT | 1344 |
| Ser | Leu | Asp | Pro 435 | Thr | Phe | Thr | Ile | Glu 440 | Thr | Ile | Thr | Leu | Pro 445 | Gln | Asp | |
| GCT | GTC | TCC | CGC | ACT | CAA | CGT | CGG | GGC | AGG | ACT | GGC | AGG | GGG | AAG | CCA | 1392 |
| Ala | Val | Ser | Arg 450 | Thr | Gln | Arg | Arg | Gly 455 | Arg | Thr | Gly | Arg | Gly 460 | Lys | Pro | |
| GGC | ATC | TAC | AGA | TTT | GTG | GCA | CCG | GGG | GAG | CGC | CCC | TCC | GGC | ATG | TTC | 1440 |
| Gly 465 | Ile | Tyr | Arg | Phe | Val 470 | Ala | Pro | Gly | Glu | Arg 475 | Pro | Ser | Gly | Met | Phe 480 | |
| GAC | TCG | TCC | GTC | CTC | TGT | GAG | TGC | TAT | GAC | GCA | GGC | TGT | GCT | TGG | TAT | 1488 |
| Asp | Ser | Ser | Val | Leu 485 | Cys | Glu | Cys | Tyr | Asp 490 | Ala | Gly | Cys | Ala | Trp 495 | Tyr | |
| GAG | CTC | ACG | CCC | GCC | GAG | ACT | ACA | GTT | AGG | CTA | CGA | GCG | TAC | ATG | AAC | 1536 |
| Glu | Leu | Thr | Pro 500 | Ala | Glu | Thr | Thr | Val 505 | Arg | Leu | Arg | Ala | Tyr 510 | Met | Asn | |
| ACC | CCG | GGG | CTT | CCC | GTG | TGC | CAG | GAC | CAT | CTT | GAA | TTT | TGG | GAG | GGC | 1584 |
| Thr | Pro | Gly | Leu 515 | Pro | Val | Cys | Gln | Asp 520 | His | Leu | Glu | Phe | Trp 525 | Glu | Gly | |
| GTC | TTT | ACA | GGC | CTC | ACT | CAT | ATA | GAT | GCC | CAC | TTT | CTA | TCC | CAG | ACA | 1632 |
| Val | Phe | Thr | Gly 530 | Leu | Thr | His | Ile | Asp 535 | Ala | His | Phe | Leu | Ser 540 | Gln | Thr | |
| AAG | CAG | AGT | GGG | GAG | AAC | CTT | CCT | TAC | CTG | GTA | GCG | TAC | CAA | GCC | ACC | 1680 |
| Lys 545 | Gln | Ser | Gly | Glu | Asn 550 | Leu | Pro | Tyr | Leu | Val 555 | Ala | Tyr | Gln | Ala | Thr 560 | |
| GTG | TGC | GCT | AGG | GCT | CAA | GCC | CCT | CCC | CCA | TCG | TGG | GAC | CAG | ATG | TGG | 1728 |
| Val | Cys | Ala | Arg | Ala 565 | Gln | Ala | Pro | Pro | Pro 570 | Ser | Trp | Asp | Gln | Met 575 | Trp | |
| AAG | TGT | TTG | ATT | CGC | CTC | AAG | CCC | ACC | CTC | CAT | GGG | CCA | ACA | CCC | CTG | 1776 |
| Lys | Cys | Leu | Ile 580 | Arg | Leu | Lys | Pro | Thr 585 | Leu | His | Gly | Pro | Thr 590 | Pro | Leu | |
| CTA | TAC | AGA | CTG | GGC | GCT | GTT | CAG | AAT | GAA | ATC | ACC | CTG | ACG | CAC | CCA | 1824 |
| Leu | Tyr | Arg 595 | Leu | Gly | Ala | Val | Gln 600 | Asn | Glu | Ile | Thr | Leu 605 | Thr | His | Pro | |
| GTC | ACC | AAA | TAC | ATC | ATG | ACA | TGC | ATG | TCG | GCC | GAC | CTG | GAG | GTC | GTC | 1872 |
| Val | Thr | Lys 610 | Tyr | Ile | Met | Thr | Cys 615 | Met | Ser | Ala | Asp | Leu 620 | Glu | Val | Val | |
| ACG | AGC | ACC | TGG | GTG | CTC | GTT | GGC | GGC | GTC | CTG | GCT | GCT | TTG | GCC | GCG | 1920 |
| Thr | Ser | Thr 625 | Trp | Val | Leu | Val 630 | Gly | Gly | Val | Leu | Ala 635 | Ala | Leu | Ala | Ala 640 | |
| TAT | TGC | CTG | TCA | ACA | GGC | TGC | GTG | GTC | ATA | GTG | GGC | AGG | GTC | GTC | TTG | 1968 |
| Tyr | Cys | Leu | Ser | Thr | Gly | Cys | Val | Val | Ile | Val | Gly | Arg | Val | Val | Leu | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 645 |     |     |     |     | 650 |     |     |     |     | 655 |     |     |      |
| TCC | GGG | AAG | CCG | GCA | ATC | ATA | CCT | GAC | AGG | GAA | GTC | CTC | TAC | CGA | GAG | 2016 |
| Ser | Gly | Lys | Pro | Ala | Ile | Ile | Pro | Asp | Arg | Glu | Val | Leu | Tyr | Arg | Glu |      |
|     |     |     | 660 |     |     |     |     | 665 |     |     |     |     | 670 |     |     |      |
| TTC | GAT | GAG | ATG | GAA | GAG | TGC | TCT | CAG | CAC | TTA | CCG | TAC | ATC | GAG | CAA | 2064 |
| Phe | Asp | Glu | Met | Glu | Glu | Cys | Ser | Gln | His | Leu | Pro | Tyr | Ile | Glu | Gln |      |
|     |     |     | 675 |     |     |     |     | 680 |     |     |     |     | 685 |     |     |      |
| GGG | ATG | ATG | CTC | GCC | GAG | CAG | TTC | AAG | CAG | AAG | GCC | CTC | GGC | CTC | CTG | 2112 |
| Gly | Met | Met | Leu | Ala | Glu | Gln | Phe | Lys | Gln | Lys | Ala | Leu | Gly | Leu | Leu |      |
|     |     |     | 690 |     |     |     |     | 695 |     |     |     |     | 700 |     |     |      |
| CAG | ACC | GCG | TCC | CGT | CAG | GCA | GAG | GTT | ATC | GCC | CCT | GCT | GTC | CAG | ACC | 2160 |
| Gln | Thr | Ala | Ser | Arg | Gln | Ala | Glu | Val | Ile | Ala | Pro | Ala | Val | Gln | Thr |      |
| 705 |     |     |     |     | 710 |     |     |     |     | 715 |     |     |     |     | 720 |      |
| AAC | TGG | CAA | AAA | CTC | GAG | ACC | TTC | TGG | GCG | AAG | CAT | ATG | TGG | AAC | TTC | 2208 |
| Asn | Trp | Gln | Lys | Leu | Glu | Thr | Phe | Trp | Ala | Lys | His | Met | Trp | Asn | Phe |      |
|     |     |     |     | 725 |     |     |     |     | 730 |     |     |     |     | 735 |     |      |
| ATC | AGT | GGG | ATA | CAA | TAC | TTG | GCG | GGC | TTG | TCA | ACG | CTG | CCT | GGT | AAC | 2256 |
| Ile | Ser | Gly | Ile | Gln | Tyr | Leu | Ala | Gly | Leu | Ser | Thr | Leu | Pro | Gly | Asn |      |
|     |     |     | 740 |     |     |     |     | 745 |     |     |     |     | 750 |     |     |      |
| CCC | GCC | ATT | GCT | TCA | TTG | ATG | GCT | TTT | ACA | GCT | GCT | GTC | ACC | AGC | CCA | 2304 |
| Pro | Ala | Ile | Ala | Ser | Leu | Met | Ala | Phe | Thr | Ala | Ala | Val | Thr | Ser | Pro |      |
|     |     |     | 755 |     |     |     |     | 760 |     |     |     |     | 765 |     |     |      |
| CTA | ACC | ACT | AGC | CAA | ACC | CTC | CTC | TTC | AAC | ATA | TTG | GGG | GGG | TGG | GTG | 2352 |
| Leu | Thr | Thr | Ser | Gln | Thr | Leu | Leu | Phe | Asn | Ile | Leu | Gly | Gly | Trp | Val |      |
|     | 770 |     |     |     |     | 775 |     |     |     |     | 780 |     |     |     |     |      |
| GCT | GCC | CAG | CTC | GCC | GCC | CCC | GGT | GCC | GCT | ACT | GCC | TTT | GTG | GGC | GCT | 2400 |
| Ala | Ala | Gln | Leu | Ala | Ala | Pro | Gly | Ala | Ala | Thr | Ala | Phe | Val | Gly | Ala |      |
| 785 |     |     |     |     | 790 |     |     |     |     | 795 |     |     |     |     | 800 |      |
| GGC | TTA | GCT | GGC | GCC | GCC | ATC | GGC | AGT | GTT | GGA | CTG | GGG | AAG | GTC | CTC | 2448 |
| Gly | Leu | Ala | Gly | Ala | Ala | Ile | Gly | Ser | Val | Gly | Leu | Gly | Lys | Val | Leu |      |
|     |     |     |     | 805 |     |     |     |     | 810 |     |     |     |     | 815 |     |      |
| ATA | GAC | ATC | CTT | GCA | GGG | TAT | GGC | GCG | GGC | GTG | GCG | GGA | GCT | CTT | GTG | 2496 |
| Ile | Asp | Ile | Leu | Ala | Gly | Tyr | Gly | Ala | Gly | Val | Ala | Gly | Ala | Leu | Val |      |
|     |     |     | 820 |     |     |     |     | 825 |     |     |     |     | 830 |     |     |      |
| GCA | TTC | AAG | ATC | ATG | AGC | GGT | GAG | GTC | CCC | TCC | ACG | GAG | GAC | CTG | GTC | 2544 |
| Ala | Phe | Lys | Ile | Met | Ser | Gly | Glu | Val | Pro | Ser | Thr | Glu | Asp | Leu | Val |      |
|     |     | 835 |     |     |     |     | 840 |     |     |     |     | 845 |     |     |     |      |
| AAT | CTA | CTG | CCC | GCC | ATC | CTC | TCG | CCC | GGA | GCC | CTC | GTA | GTC | GGC | GTG | 2592 |
| Asn | Leu | Leu | Pro | Ala | Ile | Leu | Ser | Pro | Gly | Ala | Leu | Val | Val | Gly | Val |      |
| 850 |     |     |     |     | 855 |     |     |     |     | 860 |     |     |     |     |     |      |
| GTC | TGT | GCA | GCA | ATA | CTG | CGC | CGG | CAC | GTT | GGC | CCA | GGC | GAG | GGG | GCA | 2640 |
| Val | Cys | Ala | Ala | Ile | Leu | Arg | Arg | His | Val | Gly | Pro | Gly | Glu | Gly | Ala |      |
| 865 |     |     |     |     | 870 |     |     |     |     | 875 |     |     |     |     | 880 |      |
| GTG | CAG | TGG | ATG | AAC | CGG | CTG | ATA | GCC | TTC | GCC | TCA | CGG | GGG | AAC | CAT | 2688 |
| Val | Gln | Trp | Met | Asn | Arg | Leu | Ile | Ala | Phe | Ala | Ser | Arg | Gly | Asn | His |      |
|     |     |     |     | 885 |     |     |     |     | 890 |     |     |     |     | 895 |     |      |
| GTT | TCA | CCC | GGG | AAT | TCC | AGC | ACG | AAT | CCT | AAA | CCT | CAA | AAA | AAA | AAC | 2736 |
| Val | Ser | Pro | Gly | Asn | Ser | Ser | Thr | Asn | Pro | Lys | Pro | Gln | Lys | Lys | Asn |      |
|     |     |     | 900 |     |     |     |     | 905 |     |     |     |     | 910 |     |     |      |
| AAA | CGT | AAC | ACC | AAC | CGT | CGC | CCA | CAG | GAC | GTC | AAG | TTC | CCG | GGT | GGC | 2784 |
| Lys | Arg | Asn | Thr | Asn | Arg | Arg | Pro | Gln | Asp | Val | Lys | Phe | Pro | Gly | Gly |      |
|     |     | 915 |     |     |     |     | 920 |     |     |     |     | 925 |     |     |     |      |
| GGT | CAG | ATC | GTT | GGT | GGA | GTT | TAC | TTG | TTG | CCG | CGC | AGG | GGC | CCT | AGA | 2832 |
| Gly | Gln | Ile | Val | Gly | Gly | Val | Tyr | Leu | Leu | Pro | Arg | Arg | Gly | Pro | Arg |      |
|     | 930 |     |     |     |     | 935 |     |     |     |     | 940 |     |     |     |     |      |
| TTG | GGT | GTG | CGC | GCG | ACG | AGA | AAG | ACT | TCC | GAG | CGG | TCG | CAA | CCT | CGA | 2880 |
| Leu | Gly | Val | Arg | Ala | Thr | Arg | Lys | Thr | Ser | Glu | Arg | Ser | Gln | Pro | Arg |      |
| 945 |     |     |     |     | 950 |     |     |     |     | 955 |     |     |     |     | 960 |      |
| GGT | AGA | CGT | CAG | CCT | ATC | CCC | AAG | GCT | CGT | CGG | CCC | GAG | GGC | AGG | ACC | 2928 |
| Gly | Arg | Arg | Gln | Pro | Ile | Pro | Lys | Ala | Arg | Arg | Pro | Glu | Gly | Arg | Thr |      |

-continued

```
                        965                              970                              975
TGG  GCT  CAG  CCC  GGG  TAC  CCT  TGG  CCC  CTC  TAT  GGC  AAT  GAG  GGC  TGC        2976
Trp  Ala  Gln  Pro  Gly  Tyr  Pro  Trp  Pro  Leu  Tyr  Gly  Asn  Glu  Gly  Cys
          980                              985                              990

GGG  TGG  GCG  GGA  TGG  CTC  CTG  TCT  CCC  CGT  GGC  TCT  CGG  CCT  AGC  TGG        3024
Gly  Trp  Ala  Gly  Trp  Leu  Leu  Ser  Pro  Arg  Gly  Ser  Arg  Pro  Ser  Trp
          995                              1000                             1005

GGC  CCC  ACA  GAC  CCC  CGG  CGT  AGG  TCG  CGC  AAT  TTG  GGT  TAATGAGTCG           3073
Gly  Pro  Thr  Asp  Pro  Arg  Arg  Arg  Ser  Arg  Asn  Leu  Gly
     1010                         1015                    1020

AC                                                                                     3075
```

( 2 ) INFORMATION FOR SEQ ID NO:12:

( i ) SEQUENCE CHARACTERISTICS:
        ( A ) LENGTH: 1021 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met  Ala  Thr  Lys  Ala  Val  Cys  Val  Leu  Lys  Gly  Asp  Gly  Pro  Val  Gln
 1                    5                        10                       15

Gly  Ile  Ile  Asn  Phe  Glu  Gln  Lys  Glu  Ser  Asn  Gly  Pro  Val  Lys  Val
               20                       25                       30

Trp  Gly  Ser  Ile  Lys  Gly  Leu  Thr  Glu  Gly  Leu  His  Gly  Phe  His  Val
          35                       40                       45

His  Glu  Phe  Gly  Asp  Asn  Thr  Ala  Gly  Cys  Thr  Ser  Ala  Gly  Pro  His
     50                       55                       60

Phe  Asn  Pro  Leu  Ser  Arg  Lys  His  Gly  Gly  Pro  Lys  Asp  Glu  Glu  Arg
 65                       70                       75                       80

His  Val  Gly  Asp  Leu  Gly  Asn  Val  Thr  Ala  Asp  Lys  Asp  Gly  Val  Ala
                    85                       90                       95

Asp  Val  Ser  Ile  Glu  Asp  Ser  Val  Ile  Ser  Leu  Ser  Gly  Asp  His  Cys
               100                      105                      110

Ile  Ile  Gly  Arg  Thr  Leu  Val  Val  His  Glu  Lys  Ala  Asp  Asp  Leu  Gly
          115                      120                      125

Lys  Gly  Gly  Asn  Glu  Glu  Ser  Thr  Lys  Thr  Gly  Asn  Ala  Gly  Ser  Arg
     130                      135                      140

Leu  Ala  Cys  Gly  Val  Ile  Gly  Ile  Ala  Gln  Asn  Leu  Glu  Phe  Gly  Ala
145                      150                      155                      160

Val  Asp  Phe  Ile  Pro  Val  Glu  Asn  Leu  Glu  Thr  Thr  Met  Arg  Ser  Pro
                    165                      170                      175

Val  Phe  Thr  Asp  Asn  Ser  Ser  Pro  Pro  Val  Val  Pro  Gln  Ser  Phe  Gln
               180                      185                      190

Val  Ala  His  Leu  His  Ala  Pro  Thr  Gly  Ser  Gly  Lys  Ser  Thr  Lys  Val
          195                      200                      205

Pro  Ala  Ala  Tyr  Ala  Ala  Gln  Gly  Tyr  Lys  Val  Leu  Val  Leu  Asn  Pro
     210                      215                      220

Ser  Val  Ala  Ala  Thr  Leu  Gly  Phe  Gly  Ala  Tyr  Met  Ser  Lys  Ala  His
225                      230                      235                      240

Gly  Ile  Asp  Pro  Asn  Ile  Arg  Thr  Gly  Val  Arg  Thr  Ile  Thr  Thr  Gly
                    245                      250                      255

Ser  Pro  Ile  Thr  Tyr  Ser  Thr  Tyr  Gly  Lys  Phe  Leu  Ala  Asp  Gly  Gly
               260                      265                      270

Cys  Ser  Gly  Gly  Ala  Tyr  Asp  Ile  Ile  Ile  Cys  Asp  Glu  Cys  His  Ser
```

|         |         |         |         |         | 275     |         |         |         | 280     |         |         |         | 285     |         |
|---------|---------|---------|---------|---------|---------|---------|---------|---------|---------|---------|---------|---------|---------|---------|
| Thr     | Asp     | Ala     | Thr     | Ser     | Ile     | Leu     | Gly     | Ile     | Gly     | Thr     | Val     | Leu     | Asp     | Gln     | Ala     |
|         | 290     |         |         |         |         | 295     |         |         |         | 300     |         |         |         |         |         |
| Glu     | Thr     | Ala     | Gly     | Ala     | Arg     | Leu     | Val     | Val     | Leu     | Ala     | Thr     | Ala     | Thr     | Pro     | Pro     |
| 305     |         |         |         |         | 310     |         |         |         |         | 315     |         |         |         |         | 320     |
| Gly     | Ser     | Val     | Thr     | Val     | Pro     | His     | Pro     | Asn     | Ile     | Glu     | Glu     | Val     | Ala     | Leu     | Ser     |
|         |         |         |         | 325     |         |         |         |         | 330     |         |         |         |         | 335     |         |
| Thr     | Thr     | Gly     | Glu     | Ile     | Pro     | Phe     | Tyr     | Gly     | Lys     | Ala     | Ile     | Pro     | Leu     | Glu     | Val     |
|         |         |         | 340     |         |         |         |         | 345     |         |         |         |         | 350     |         |         |
| Ile     | Lys     | Gly     | Gly     | Arg     | His     | Leu     | Ile     | Phe     | Cys     | His     | Ser     | Lys     | Lys     | Lys     | Cys     |
|         |         | 355     |         |         |         |         | 360     |         |         |         |         | 365     |         |         |         |
| Asp     | Glu     | Leu     | Ala     | Ala     | Lys     | Leu     | Val     | Ala     | Leu     | Gly     | Ile     | Asn     | Ala     | Val     | Ala     |
|         | 370     |         |         |         |         | 375     |         |         |         |         | 380     |         |         |         |         |
| Tyr     | Tyr     | Arg     | Gly     | Leu     | Asp     | Val     | Ser     | Val     | Ile     | Pro     | Thr     | Ser     | Gly     | Asp     | Val     |
| 385     |         |         |         |         | 390     |         |         |         |         | 395     |         |         |         |         | 400     |
| Val     | Val     | Val     | Ala     | Thr     | Asp     | Ala     | Leu     | Met     | Thr     | Gly     | Tyr     | Thr     | Gly     | Asp     | Phe     |
|         |         |         |         | 405     |         |         |         |         | 410     |         |         |         |         | 415     |         |
| Asp     | Ser     | Val     | Ile     | Asp     | Cys     | Asn     | Thr     | Cys     | Val     | Thr     | Gln     | Thr     | Val     | Asp     | Phe     |
|         |         |         | 420     |         |         |         |         | 425     |         |         |         |         | 430     |         |         |
| Ser     | Leu     | Asp     | Pro     | Thr     | Phe     | Thr     | Ile     | Glu     | Thr     | Ile     | Thr     | Leu     | Pro     | Gln     | Asp     |
|         |         | 435     |         |         |         |         | 440     |         |         |         |         | 445     |         |         |         |
| Ala     | Val     | Ser     | Arg     | Thr     | Gln     | Arg     | Arg     | Gly     | Arg     | Thr     | Gly     | Arg     | Gly     | Lys     | Pro     |
|         | 450     |         |         |         |         | 455     |         |         |         |         | 460     |         |         |         |         |
| Gly     | Ile     | Tyr     | Arg     | Phe     | Val     | Ala     | Pro     | Gly     | Glu     | Arg     | Pro     | Ser     | Gly     | Met     | Phe     |
| 465     |         |         |         |         | 470     |         |         |         |         | 475     |         |         |         |         | 480     |
| Asp     | Ser     | Ser     | Val     | Leu     | Cys     | Glu     | Cys     | Tyr     | Asp     | Ala     | Gly     | Cys     | Ala     | Trp     | Tyr     |
|         |         |         |         | 485     |         |         |         |         | 490     |         |         |         |         | 495     |         |
| Glu     | Leu     | Thr     | Pro     | Ala     | Glu     | Thr     | Thr     | Val     | Arg     | Leu     | Arg     | Ala     | Tyr     | Met     | Asn     |
|         |         |         | 500     |         |         |         |         | 505     |         |         |         |         | 510     |         |         |
| Thr     | Pro     | Gly     | Leu     | Pro     | Val     | Cys     | Gln     | Asp     | His     | Leu     | Glu     | Phe     | Trp     | Glu     | Gly     |
|         |         | 515     |         |         |         |         | 520     |         |         |         |         | 525     |         |         |         |
| Val     | Phe     | Thr     | Gly     | Leu     | Thr     | His     | Ile     | Asp     | Ala     | His     | Phe     | Leu     | Ser     | Gln     | Thr     |
|         | 530     |         |         |         |         | 535     |         |         |         |         | 540     |         |         |         |         |
| Lys     | Gln     | Ser     | Gly     | Glu     | Asn     | Leu     | Pro     | Tyr     | Leu     | Val     | Ala     | Tyr     | Gln     | Ala     | Thr     |
| 545     |         |         |         |         | 550     |         |         |         |         | 555     |         |         |         |         | 560     |
| Val     | Cys     | Ala     | Arg     | Ala     | Gln     | Ala     | Pro     | Pro     | Pro     | Ser     | Trp     | Asp     | Gln     | Met     | Trp     |
|         |         |         |         | 565     |         |         |         |         | 570     |         |         |         |         | 575     |         |
| Lys     | Cys     | Leu     | Ile     | Arg     | Leu     | Lys     | Pro     | Thr     | Leu     | His     | Gly     | Pro     | Thr     | Pro     | Leu     |
|         |         |         | 580     |         |         |         |         | 585     |         |         |         |         | 590     |         |         |
| Leu     | Tyr     | Arg     | Leu     | Gly     | Ala     | Val     | Gln     | Asn     | Glu     | Ile     | Thr     | Leu     | Thr     | His     | Pro     |
|         |         | 595     |         |         |         |         | 600     |         |         |         |         | 605     |         |         |         |
| Val     | Thr     | Lys     | Tyr     | Ile     | Met     | Thr     | Cys     | Met     | Ser     | Ala     | Asp     | Leu     | Glu     | Val     | Val     |
|         |         | 610     |         |         |         |         | 615     |         |         |         |         | 620     |         |         |         |
| Thr     | Ser     | Thr     | Trp     | Val     | Leu     | Val     | Gly     | Gly     | Val     | Leu     | Ala     | Ala     | Leu     | Ala     | Ala     |
| 625     |         |         |         |         | 630     |         |         |         |         | 635     |         |         |         |         | 640     |
| Tyr     | Cys     | Leu     | Ser     | Thr     | Gly     | Cys     | Val     | Val     | Ile     | Val     | Gly     | Arg     | Val     | Val     | Leu     |
|         |         |         |         | 645     |         |         |         |         | 650     |         |         |         |         | 655     |         |
| Ser     | Gly     | Lys     | Pro     | Ala     | Ile     | Ile     | Pro     | Asp     | Arg     | Glu     | Val     | Leu     | Tyr     | Arg     | Glu     |
|         |         |         | 660     |         |         |         |         | 665     |         |         |         |         | 670     |         |         |
| Phe     | Asp     | Glu     | Met     | Glu     | Glu     | Cys     | Ser     | Gln     | His     | Leu     | Pro     | Tyr     | Ile     | Glu     | Gln     |
|         |         | 675     |         |         |         |         | 680     |         |         |         |         | 685     |         |         |         |
| Gly     | Met     | Met     | Leu     | Ala     | Glu     | Gln     | Phe     | Lys     | Gln     | Lys     | Ala     | Leu     | Gly     | Leu     | Leu     |
|         | 690     |         |         |         |         | 695     |         |         |         |         | 700     |         |         |         |         |

-continued

```
Gln Thr Ala Ser Arg Gln Ala Glu Val Ile Ala Pro Ala Val Gln Thr
705                 710                 715                 720

Asn Trp Gln Lys Leu Glu Thr Phe Trp Ala Lys His Met Trp Asn Phe
                725                 730                 735

Ile Ser Gly Ile Gln Tyr Leu Ala Gly Leu Ser Thr Leu Pro Gly Asn
            740                 745                 750

Pro Ala Ile Ala Ser Leu Met Ala Phe Thr Ala Ala Val Thr Ser Pro
        755                 760                 765

Leu Thr Thr Ser Gln Thr Leu Leu Phe Asn Ile Leu Gly Gly Trp Val
    770                 775                 780

Ala Ala Gln Leu Ala Ala Pro Gly Ala Ala Thr Ala Phe Val Gly Ala
785                 790                 795                 800

Gly Leu Ala Gly Ala Ala Ile Gly Ser Val Gly Leu Gly Lys Val Leu
                805                 810                 815

Ile Asp Ile Leu Ala Gly Tyr Gly Ala Gly Val Ala Gly Ala Leu Val
            820                 825                 830

Ala Phe Lys Ile Met Ser Gly Glu Val Pro Ser Thr Glu Asp Leu Val
        835                 840                 845

Asn Leu Leu Pro Ala Ile Leu Ser Pro Gly Ala Leu Val Val Gly Val
    850                 855                 860

Val Cys Ala Ala Ile Leu Arg Arg His Val Gly Pro Gly Glu Gly Ala
865                 870                 875                 880

Val Gln Trp Met Asn Arg Leu Ile Ala Phe Ala Ser Arg Gly Asn His
                885                 890                 895

Val Ser Pro Gly Asn Ser Ser Thr Asn Pro Lys Pro Gln Lys Lys Asn
            900                 905                 910

Lys Arg Asn Thr Asn Arg Arg Pro Gln Asp Val Lys Phe Pro Gly Gly
        915                 920                 925

Gly Gln Ile Val Gly Gly Val Tyr Leu Leu Pro Arg Arg Gly Pro Arg
    930                 935                 940

Leu Gly Val Arg Ala Thr Arg Lys Thr Ser Glu Arg Ser Gln Pro Arg
945                 950                 955                 960

Gly Arg Arg Gln Pro Ile Pro Lys Ala Arg Arg Pro Glu Gly Arg Thr
                965                 970                 975

Trp Ala Gln Pro Gly Tyr Pro Trp Pro Leu Tyr Gly Asn Glu Gly Cys
            980                 985                 990

Gly Trp Ala Gly Trp Leu Leu Ser Pro Arg Gly Ser Arg Pro Ser Trp
        995                 1000                1005

Gly Pro Thr Asp Pro Arg Arg Arg Ser Arg Asn Leu Gly
    1010                1015                1020
```